United States Patent
Cauthen, III et al.

(10) Patent No.: US 7,922,768 B2
(45) Date of Patent: *Apr. 12, 2011

(54) SPINAL DISC ANNULUS RECONSTRUCTION METHOD AND DEFORMABLE SPINAL DISC ANNULUS STENT

(75) Inventors: Joseph C. Cauthen, III, Gainesville, FL (US); Matthew M. Burns, Orono, MN (US); Thomas R. Hektner, Hamel, MN (US); Paul Burmeister, Maple Grove, MN (US); Lawrence W. Wales, Maplewood, MN (US); Daniel O. Adams, Orono, MN (US); Rodney L. Houfburg, Prior Lake, MN (US)

(73) Assignee: Anulex Technologies, Inc., Minnetonka, MN (US)

( * ) Notice: Subject to any disclaimer, the term of this patent is extended or adjusted under 35 U.S.C. 154(b) by 782 days.

This patent is subject to a terminal disclaimer.

(21) Appl. No.: 11/559,457

(22) Filed: Nov. 14, 2006

(65) Prior Publication Data

US 2007/0088438 A1    Apr. 19, 2007

Related U.S. Application Data

(63) Continuation of application No. 11/386,642, filed on Mar. 23, 2006, which is a continuation of application No. 10/133,339, filed on Apr. 29, 2002, now Pat. No. 7,052,516, said application No. 11/386,642 is a continuation-in-part of application No. 10/075,615, filed on Feb. 15, 2002, now abandoned, which is a continuation-in-part of application No. 09/947,078, filed on Sep. 5, 2001, now Pat. No. 6,592,625, which is a continuation of application No. 09/484,706, filed on Jan. 18, 2000, now abandoned.

(60) Provisional application No. 60/309,105, filed on Jul. 31, 2001, provisional application No. 60/160,710, filed on Oct. 20, 1999.

(51) Int. Cl.
*A61F 2/44* (2006.01)
*A61F 2/46* (2006.01)
(52) U.S. Cl. .................................. 623/17.16; 606/86 R
(58) Field of Classification Search .... 623/17.11–17.16, 623/1.11, 1.12, 1.2, 1.22, 1.23; 606/151–157
See application file for complete search history.

(56) References Cited

U.S. PATENT DOCUMENTS 1,995,970 A    3/1935    Dorough
(Continued)

FOREIGN PATENT DOCUMENTS

DE    43 23 959501    7/1994
(Continued)

OTHER PUBLICATIONS

Ahlgren, B.D., MD., et al., "Anular Incision Technique on the Strength and Multidirectional Flexibility of the Healing Intervertebral Disc," *Spine* 19(8):948-954 (1994).

(Continued)

*Primary Examiner* — Anu Ramana
(74) *Attorney, Agent, or Firm* — Faegre & Benson LLP

(57) ABSTRACT

A spinal disc annulus repair device for repair and reconstruction of the spinal disc wall (annulus) after surgical invasion or pathologic rupture, which may incorporate suture closure or other means of stent insertion and fixation, designed to reduce the failure rate of conventional surgical procedures on the spinal discs.

16 Claims, 63 Drawing Sheets

U.S. PATENT DOCUMENTS

| | | |
|---|---|---|
| 2,609,347 A | 9/1952 | Wilson |
| 2,653,917 A | 9/1953 | Hammon |
| 2,659,935 A | 11/1953 | Hammon |
| 2,664,366 A | 12/1953 | Wilson |
| 2,664,367 A | 12/1953 | Wilson |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,846,407 A | 8/1958 | Wilson |
| 2,951,828 A | 9/1960 | Zeile |
| 3,531,561 A | 9/1970 | Trehu |
| 3,580,256 A | 5/1971 | Wilkinson |
| 3,867,728 A | 2/1975 | Stubstad et al. |
| 3,874,388 A | 4/1975 | King et al. |
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Field |
| 4,059,115 A | 11/1977 | Jamushev |
| 4,224,413 A | 9/1980 | Burbidge |
| 4,349,921 A | 9/1982 | Kuntz |
| 4,369,788 A | 1/1983 | Goald |
| 4,413,359 A | 11/1983 | Akiyama et al. |
| 4,502,161 A | 3/1985 | Wall |
| 4,512,338 A | 4/1985 | Balko et al. |
| 4,520,821 A | 6/1985 | Schmidt |
| 4,532,926 A | 8/1985 | O'Holla |
| 4,545,374 A | 10/1985 | Jacobson |
| 4,602,635 A | 7/1986 | Mulhollan et al. |
| 4,663,358 A | 5/1987 | Hyon et al. |
| 4,669,473 A | 6/1987 | Richards et al. |
| 4,678,459 A | 7/1987 | Onik et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,863,477 A | 9/1989 | Monson |
| 4,873,976 A | 10/1989 | Schreiber |
| 4,884,572 A | 12/1989 | Bays et al. |
| 4,890,612 A | 1/1990 | Kensey |
| 4,895,148 A | 1/1990 | Bays et al. |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 4,976,715 A | 12/1990 | Bays et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kuslich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,204,106 A | 4/1993 | Schepers et al. |
| 5,207,695 A | 5/1993 | Trout |
| 5,222,962 A | 6/1993 | Burkhart |
| 5,222,974 A | 6/1993 | Kensey et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,350,399 A | 9/1994 | Erlebacher |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,697 A | 12/1994 | Baumgartner |
| 5,374,268 A | 12/1994 | Sander |
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,360 A | 4/1995 | Tovey |
| 5,411,520 A | 5/1995 | Nash |
| 5,417,699 A | 5/1995 | Klein et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,439,464 A | 8/1995 | Shapiro |
| 5,456,720 A | 10/1995 | Schultz et al. |
| 5,464,407 A | 11/1995 | McGuire |
| 5,470,337 A | 11/1995 | Moss |
| 5,489,307 A | 2/1996 | Kuslich et al. |
| 5,492,697 A | 2/1996 | Boyan et al. |
| 5,496,348 A | 3/1996 | Bonutti |
| 5,500,000 A | 3/1996 | Feagin et al. |
| 5,507,754 A | 4/1996 | Green et al. |
| 5,507,755 A | 4/1996 | Gresl et al. |
| 5,514,180 A | 5/1996 | Heggeness et al. |
| 5,520,700 A | 5/1996 | Beyar et al. |
| 5,531,678 A | 7/1996 | Tomba et al. |
| 5,531,759 A | 7/1996 | Kensey et al. |
| 5,534,028 A | 7/1996 | Bao et al. |
| 5,534,030 A | 7/1996 | Navarro et al. |

| | | | | | | |
|---|---|---|---|---|---|---|
| 5,540,704 A | 7/1996 | Gordon et al. | | 5,782,860 A | 7/1998 | Epstein et al. |
| 5,540,715 A | 7/1996 | Katsaros et al. | | 5,785,705 A | 7/1998 | Baker |
| 5,545,178 A | 8/1996 | Kensey et al. | | 5,786,217 A | 7/1998 | Tubo et al. |
| 5,545,229 A | 8/1996 | Parsons et al. | | 5,788,625 A | 8/1998 | Plouhar et al. |
| 5,549,617 A | 8/1996 | Green et al. | | 5,792,152 A | 8/1998 | Klein et al. |
| 5,549,679 A | 8/1996 | Kuslich | | 5,797,929 A | 8/1998 | Andreas et al. |
| 5,556,428 A | 9/1996 | Shah | | 5,800,549 A | 9/1998 | Bao et al. |
| 5,556,429 A | 9/1996 | Felt | | 5,800,550 A | 9/1998 | Sertich |
| 5,562,684 A | 10/1996 | Kammerer | | 5,810,848 A | 9/1998 | Hayhurst |
| 5,562,689 A | 10/1996 | Green et al. | | 5,810,851 A | 9/1998 | Yoon |
| 5,562,736 A | 10/1996 | Ray et al. | | 5,823,994 A | 10/1998 | Sharkey et al. |
| 5,562,738 A | 10/1996 | Boyd et al. | | 5,824,008 A | 10/1998 | Bolduc et al. |
| 5,569,242 A | 10/1996 | Lax et al. | | 5,824,082 A | 10/1998 | Brown |
| 5,569,252 A | 10/1996 | Justin et al. | | 5,824,093 A | 10/1998 | Ray et al. |
| 5,571,189 A | 11/1996 | Kuslich | | 5,824,094 A | 10/1998 | Serhan et al. |
| 5,573,286 A | 11/1996 | Rogozinski | | 5,827,298 A | 10/1998 | Hart et al. |
| 5,582,616 A | 12/1996 | Bolduc et al. | | 5,827,325 A | 10/1998 | Landgrebe et al. |
| 5,584,862 A | 12/1996 | Bonutti | | 5,827,328 A | 10/1998 | Butterman |
| 5,591,177 A | 1/1997 | Lehrer | | 5,836,315 A | 11/1998 | Benderev et al. |
| 5,591,223 A | 1/1997 | Lock et al. | | 5,842,477 A | 12/1998 | Naughton et al. |
| 5,593,425 A | 1/1997 | Bonutti et al. | | 5,843,084 A | 12/1998 | Hart et al. |
| 5,599,279 A | 2/1997 | Slotman et al. | | 5,846,261 A | 12/1998 | Kotula et al. |
| 5,613,974 A | 3/1997 | Andreas et al. | | 5,849,331 A | 12/1998 | Ducheyne et al. |
| 5,620,012 A | 4/1997 | Benderev et al. | | 5,853,422 A | 12/1998 | Huebsch et al. |
| 5,624,463 A | 4/1997 | Stone et al. | | 5,855,614 A | 1/1999 | Stevens et al. |
| 5,626,612 A | 5/1997 | Bartlett et al. | | 5,860,425 A | 1/1999 | Benderev et al. |
| 5,626,613 A | 5/1997 | Schmieding | | 5,860,977 A | 1/1999 | Zucherman et al. |
| 5,626,614 A | 5/1997 | Hart | | 5,861,004 A | 1/1999 | Kensey |
| 5,634,931 A | 6/1997 | Kugel | | 5,865,845 A | 2/1999 | Thalgott |
| 5,634,944 A | 6/1997 | Magram | | 5,865,846 A | 2/1999 | Bryan et al. |
| 5,643,319 A | 7/1997 | Green et al. | | 5,868,762 A | 2/1999 | Cragg et al. |
| 5,645,084 A | 7/1997 | McKay | | 5,879,366 A | 3/1999 | Shaw et al. |
| 5,645,597 A | 7/1997 | Krapiva | | 5,888,220 A | 3/1999 | Felt et al. |
| 5,649,945 A | 7/1997 | Ray et al. | | 5,888,222 A | 3/1999 | Coates |
| 5,658,343 A | 8/1997 | Hauselmann et al. | | 5,888,226 A | 3/1999 | Rogozinski |
| 5,662,681 A | 9/1997 | Nash et al. | | 5,893,592 A | 4/1999 | Schulze et al. |
| 5,662,683 A | 9/1997 | Kay | | 5,893,889 A | 4/1999 | Harrington |
| 5,669,935 A | 9/1997 | Rosenman et al. | | 5,895,426 A | 4/1999 | Scarborough et al. |
| 5,674,294 A | 10/1997 | Bainville et al. | | 5,904,703 A | 5/1999 | Gilson et al. |
| 5,674,296 A | 10/1997 | Bryan et al. | | 5,916,225 A | 6/1999 | Kugel |
| 5,676,698 A | 10/1997 | Janzen et al. | | 5,919,235 A | 7/1999 | Husson et al. |
| 5,676,701 A | 10/1997 | Yuan et al. | | 5,922,026 A | 7/1999 | Chin |
| 5,681,310 A | 10/1997 | Yuan et al. | | 5,922,028 A | 7/1999 | Plouhar et al. |
| 5,681,351 A | 10/1997 | Jamiolkowski et al. | | 5,928,284 A | 7/1999 | Mehdizadeh |
| 5,683,417 A | 11/1997 | Cooper | | 5,935,147 A | 8/1999 | Kensey et al. |
| 5,683,465 A | 11/1997 | Shinn et al. | | 5,941,439 A | 8/1999 | Kammerer et al. |
| 5,695,525 A | 12/1997 | Mulhauser et al. | | 5,944,738 A | 8/1999 | Amplatz et al. |
| 5,697,950 A | 12/1997 | Fucci et al. | | 5,948,001 A | 9/1999 | Larsen |
| 5,702,449 A | 12/1997 | McKay | | 5,948,002 A | 9/1999 | Bonutti |
| 5,702,450 A | 12/1997 | Bisserie | | 5,954,716 A | 9/1999 | Sharkey et al. |
| 5,702,451 A | 12/1997 | Biedermann et al. | | 5,954,767 A | 9/1999 | Pajotin et al. |
| 5,702,454 A | 12/1997 | Baumgartner | | 5,957,939 A | 9/1999 | Heaven et al. |
| 5,702,462 A | 12/1997 | Oberlander | | 5,964,783 A | 10/1999 | Grafton et al. |
| 5,704,943 A | 1/1998 | Yoon et al. | | 5,964,807 A | 10/1999 | Gan et al. |
| 5,716,404 A | 2/1998 | Vacanti et al. | | 5,972,000 A | 10/1999 | Beyar et al. |
| 5,716,408 A | 2/1998 | Eldridge et al. | | 5,972,007 A | 10/1999 | Sheffield et al. |
| 5,716,409 A | 2/1998 | Debbas | | 5,972,022 A | 10/1999 | Huxel |
| 5,716,413 A | 2/1998 | Walter et al. | | 5,976,174 A | 11/1999 | Ruiz |
| 5,716,416 A | 2/1998 | Lin | | 5,976,186 A | 11/1999 | Bao et al. |
| 5,725,552 A | 3/1998 | Kotula et al. | | 5,980,504 A | 11/1999 | Sharkey et al. |
| 5,725,577 A | 3/1998 | Saxon | | 5,984,948 A | 11/1999 | Hasson |
| 5,728,109 A | 3/1998 | Schulze et al. | | 6,001,130 A | 12/1999 | Bryan et al. |
| 5,728,150 A | 3/1998 | McDonald et al. | | 6,007,567 A | 12/1999 | Bonutti |
| 5,730,744 A | 3/1998 | Justin et al. | | 6,007,570 A | 12/1999 | Sharkey et al. |
| 5,733,337 A | 3/1998 | Carr, Jr. et al. | | 6,007,575 A | 12/1999 | Samuels |
| 5,735,875 A | 4/1998 | Bonutti | | 6,019,792 A | 2/2000 | Cauthen |
| 5,736,746 A | 4/1998 | Furutoh | | 6,019,793 A | 2/2000 | Perren et al. |
| 5,741,277 A * | 4/1998 | Gordon et al. ............ 606/144 | | 6,024,096 A | 2/2000 | Buckberg |
| 5,743,917 A | 4/1998 | Saxon | | 6,024,754 A | 2/2000 | Engelson |
| 5,746,755 A | 5/1998 | Wood et al. | | 6,024,758 A | 2/2000 | Thal |
| 5,752,964 A | 5/1998 | Mericle | | 6,027,527 A | 2/2000 | Asano et al. |
| 5,755,797 A | 5/1998 | Baumgartner | | 6,036,699 A | 3/2000 | Andreas et al. |
| 5,759,189 A | 6/1998 | Ferragamo et al. | | 6,039,761 A | 3/2000 | Li et al. |
| 5,766,246 A | 6/1998 | Mulhauser et al. | | 6,039,762 A | 3/2000 | McKay |
| 5,769,864 A | 6/1998 | Kugel | | 6,045,561 A | 4/2000 | Marshall et al. |
| 5,769,893 A | 6/1998 | Shah | | 6,053,909 A | 4/2000 | Shadduck |
| 5,772,661 A | 6/1998 | Michelson | | 6,063,378 A | 5/2000 | Nohara et al. |
| 5,776,183 A | 7/1998 | Kanesaka et al. | | 6,066,146 A | 5/2000 | Carroll et al. |
| 5,782,844 A | 7/1998 | Yoon et al. | | 6,066,776 A | 5/2000 | Goodwin et al. |

| | | | |
|---|---|---|---|
| 6,073,051 A | 6/2000 | Sharkey et al. |
| 6,080,182 A | 6/2000 | Shaw et al. |
| 6,093,205 A | 7/2000 | McLeod et al. |
| 6,095,149 A | 8/2000 | Sharkey et al. |
| 6,099,514 A | 8/2000 | Sharkey et al. |
| 6,106,545 A | 8/2000 | Egan |
| 6,113,609 A | 9/2000 | Adams |
| 6,113,623 A | 9/2000 | Sgro |
| 6,113,639 A | 9/2000 | Ray et al. |
| 6,123,715 A | 9/2000 | Amplatz |
| 6,126,682 A | 10/2000 | Sharkey et al. |
| 6,140,452 A | 10/2000 | Felt et al. |
| 6,143,006 A | 11/2000 | Chan et al. |
| 6,146,380 A | 11/2000 | Racz et al. |
| 6,146,422 A | 11/2000 | Lawson |
| 6,162,203 A | 12/2000 | Haago |
| 6,171,317 B1 | 1/2001 | Jackson et al. |
| 6,171,318 B1 | 1/2001 | Kugel et al. |
| 6,171,329 B1 | 1/2001 | Shaw et al. |
| 6,174,322 B1 | 1/2001 | Schneidt |
| 6,176,863 B1 | 1/2001 | Kugel et al. |
| 6,179,874 B1 | 1/2001 | Cauthen |
| 6,179,879 B1 | 1/2001 | Robinson et al. |
| 6,183,518 B1 | 2/2001 | Ross et al. |
| 6,187,048 B1 | 2/2001 | Milner et al. |
| 6,190,401 B1 | 2/2001 | Green et al. |
| 6,200,329 B1 | 3/2001 | Fung et al. |
| 6,203,554 B1 | 3/2001 | Roberts |
| 6,203,565 B1 | 3/2001 | Bonutti |
| 6,206,895 B1 | 3/2001 | Levinson |
| 6,206,921 B1 | 3/2001 | Guagliano et al. |
| 6,221,092 B1 | 4/2001 | Koike et al. |
| 6,221,109 B1 | 4/2001 | Geistlich et al. |
| 6,224,630 B1 | 5/2001 | Bao et al. |
| 6,231,615 B1 | 5/2001 | Preissman |
| 6,241,768 B1 | 6/2001 | Agarwal et al. |
| 6,245,080 B1 | 6/2001 | Levinson |
| 6,245,107 B1 | 6/2001 | Ferree |
| 6,248,106 B1 | 6/2001 | Ferree |
| 6,248,131 B1 | 6/2001 | Felt et al. |
| 6,267,772 B1 | 7/2001 | Mulhauser et al. |
| 6,280,453 B1 | 8/2001 | Kugel et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,306,177 B1 | 10/2001 | Felt et al. |
| 6,312,448 B1 | 11/2001 | Bonutti |
| 6,319,263 B1 | 11/2001 | Levinson |
| 6,332,894 B1 | 12/2001 | Stalcup |
| 6,340,369 B1 | 1/2002 | Ferree |
| 6,342,064 B1 | 1/2002 | Koike et al. |
| 6,344,057 B1 | 2/2002 | Rabbe et al. |
| 6,344,058 B1 | 2/2002 | Ferree |
| 6,352,557 B1 | 3/2002 | Ferree |
| 6,355,052 B1 | 3/2002 | Neuss |
| 6,364,897 B1 | 4/2002 | Bonutti |
| 6,371,984 B1 | 4/2002 | Van Dyke et al. |
| 6,371,990 B1 | 4/2002 | Ferree |
| 6,391,060 B1 | 5/2002 | Ory et al. |
| 6,402,750 B1 | 6/2002 | Atkinson et al. |
| 6,402,784 B1 | 6/2002 | Wardlaw |
| 6,402,785 B1 | 6/2002 | Zdeblick |
| 6,409,739 B1 | 6/2002 | Nobles et al. |
| 6,419,676 B1 | 7/2002 | Zucherman et al. |
| 6,419,702 B1 | 7/2002 | Ferree |
| 6,419,703 B1 | 7/2002 | Fallin et al. |
| 6,419,704 B1 | 7/2002 | Ferree |
| 6,419,706 B1 | 7/2002 | Graf |
| 6,423,065 B2 | 7/2002 | Ferree |
| 6,425,919 B1 | 7/2002 | Lambrecht |
| 6,425,924 B1 | 7/2002 | Rousseau |
| 6,428,562 B2 | 8/2002 | Bonutti |
| 6,428,576 B1 | 8/2002 | Haldimann |
| 6,432,107 B1 | 8/2002 | Ferree |
| 6,432,123 B2 | 8/2002 | Schwartz et al. |
| 6,436,098 B1 | 8/2002 | Michelson |
| 6,436,143 B1 | 8/2002 | Ross et al. |
| 6,443,988 B2 | 9/2002 | Felt et al. |
| 6,447,531 B1 | 9/2002 | Amplatz |
| 6,452,924 B1 | 9/2002 | Golden et al. |
| 6,454,804 B1 | 9/2002 | Ferree |
| 6,464,712 B1 | 10/2002 | Epstein |
| 6,482,235 B1 | 11/2002 | Lambrecht et al. |
| 6,488,691 B1 | 12/2002 | Carroll et al. |
| 6,491,724 B1 | 12/2002 | Ferree |
| 6,494,883 B1 | 12/2002 | Ferree |
| 6,500,132 B1 | 12/2002 | Li |
| 6,500,184 B1 | 12/2002 | Chan et al. |
| 6,506,204 B2 | 1/2003 | Mazzocchi |
| 6,508,828 B1 | 1/2003 | Akerfeldt et al. |
| 6,508,839 B1 | 1/2003 | Lambrecht et al. |
| 6,511,488 B1 | 1/2003 | Marshall et al. |
| 6,511,498 B1 | 1/2003 | Fumex |
| 6,511,958 B1 | 1/2003 | Atkinson et al. |
| 6,514,255 B1 | 2/2003 | Ferree |
| 6,514,514 B1 | 2/2003 | Atkinson et al. |
| 6,530,933 B1 | 3/2003 | Yeung et al. |
| 6,533,799 B1 | 3/2003 | Bouchier |
| 6,533,817 B1 | 3/2003 | Norton et al. |
| 6,547,806 B1 | 4/2003 | Ding |
| 6,558,386 B1 | 5/2003 | Cragg |
| 6,558,390 B2 | 5/2003 | Cragg |
| 6,562,052 B2 | 5/2003 | Nobles et al. |
| 6,569,187 B1 | 5/2003 | Bonutti et al. |
| 6,569,442 B2 | 5/2003 | Gan et al. |
| 6,572,635 B1 | 6/2003 | Bonutti |
| 6,572,653 B1 | 6/2003 | Simonson |
| 6,575,979 B1 | 6/2003 | Cragg |
| 6,576,017 B2 | 6/2003 | Foley et al. |
| 6,579,291 B1 | 6/2003 | Keith et al. |
| 6,592,608 B2 | 7/2003 | Fisher et al. |
| 6,592,609 B1 | 7/2003 | Bonutti |
| 6,592,625 B2 | 7/2003 | Cauthen |
| 6,596,012 B2 | 7/2003 | Akerfeldt et al. |
| 6,602,291 B1 | 8/2003 | Ray et al. |
| 6,605,096 B1 | 8/2003 | Ritchart |
| 6,607,541 B1 | 8/2003 | Gardiner et al. |
| 6,610,006 B1 | 8/2003 | Amid et al. |
| 6,610,071 B1 | 8/2003 | Cohn et al. |
| 6,610,079 B1 | 8/2003 | Li et al. |
| 6,610,091 B1 | 8/2003 | Reiley |
| 6,610,666 B1 | 8/2003 | Akerblom |
| 6,613,044 B2 | 9/2003 | Carl |
| 6,620,185 B1 | 9/2003 | Harvie et al. |
| 6,620,196 B1 | 9/2003 | Trieu |
| 6,623,492 B1 | 9/2003 | Berube et al. |
| 6,623,508 B2 | 9/2003 | Shaw et al. |
| 6,626,899 B2 | 9/2003 | Houser et al. |
| 6,626,916 B1 | 9/2003 | Yeung et al. |
| 6,635,073 B2 | 10/2003 | Bonutti et al. |
| 6,645,247 B2 | 11/2003 | Ferree |
| 6,648,918 B2 | 11/2003 | Ferree |
| 6,648,919 B2 | 11/2003 | Ferree |
| 6,648,920 B2 | 11/2003 | Ferree |
| 6,652,585 B2 | 11/2003 | Lange |
| 6,656,182 B1 | 12/2003 | Hayhurst |
| 6,669,687 B1 | 12/2003 | Saadat |
| 6,669,707 B1 | 12/2003 | Swanstrom et al. |
| 6,669,729 B2 | 12/2003 | Chin |
| 6,673,088 B1 | 1/2004 | Vargas et al. |
| 6,676,665 B2 | 1/2004 | Foley et al. |
| 6,679,914 B1 | 1/2004 | Gabbay |
| 6,684,886 B1 | 2/2004 | Alleyne |
| 6,685,695 B2 | 2/2004 | Ferree |
| 6,689,125 B1 | 2/2004 | Keith et al. |
| 6,692,506 B1 | 2/2004 | Ory et al. |
| 6,695,858 B1 | 2/2004 | Dubrul et al. |
| 6,696,073 B2 | 2/2004 | Boyce |
| 6,699,263 B2 | 3/2004 | Cope |
| 6,706,068 B2 | 3/2004 | Ferree |
| 6,712,836 B1 | 3/2004 | Berg et al. |
| 6,712,837 B2 | 3/2004 | Akerfeldt et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,719,797 B1 | 4/2004 | Ferree |
| 6,723,058 B2 | 4/2004 | Li |

| | | |
|---|---|---|
| 6,723,095 B2 | 4/2004 | Hammerslag |
| 6,723,097 B2 | 4/2004 | Fraser et al. |
| 6,723,107 B1 | 4/2004 | Skiba et al. |
| 6,723,133 B1 | 4/2004 | Pajotin |
| 6,723,335 B1 | 4/2004 | Moehlenbruck et al. |
| 6,726,696 B1 | 4/2004 | Houser |
| 6,726,721 B2 | 4/2004 | Stoy et al. |
| 6,730,112 B2 | 5/2004 | Levinson |
| 6,733,531 B1 | 5/2004 | Trieu |
| 6,733,534 B2 | 5/2004 | Sherman |
| 6,736,815 B2 | 5/2004 | Ginn |
| 6,740,093 B2 | 5/2004 | Hochschuler et al. |
| 6,743,255 B2 | 6/2004 | Ferree |
| 6,752,831 B2 | 6/2004 | Sybert et al. |
| 6,758,863 B2 | 7/2004 | Estes |
| 6,761,720 B1 | 7/2004 | Senegas |
| 6,764,514 B1 | 7/2004 | Li et al. |
| 6,767,037 B2 | 7/2004 | Wenstrom |
| 6,773,699 B1 | 8/2004 | Soltz et al. |
| 6,783,546 B2 | 8/2004 | Zucherman et al. |
| 6,805,695 B2 | 10/2004 | Keith |
| 6,805,697 B1 | 10/2004 | Helm et al. |
| 6,805,715 B2 | 10/2004 | Reuter et al. |
| 6,812,211 B2 | 11/2004 | Slivka et al. |
| 6,821,276 B2 | 11/2004 | Lambrecht et al. |
| 6,824,562 B2 | 11/2004 | Mathis et al. |
| 6,827,716 B2 | 12/2004 | Ryan et al. |
| 6,827,743 B2 | 12/2004 | Eisermann et al. |
| 6,830,570 B1 | 12/2004 | Frey et al. |
| 6,833,006 B2 | 12/2004 | Foley et al. |
| 6,835,205 B2 | 12/2004 | Atkinson et al. |
| 6,835,207 B2 | 12/2004 | Zacouto et al. |
| 6,835,208 B2 | 12/2004 | Marchosky |
| 6,841,150 B2 | 1/2005 | Halvorsen et al. |
| 6,852,128 B2 | 2/2005 | Lange |
| 6,860,895 B1 | 3/2005 | Akerfeldt et al. |
| 6,878,155 B2 | 4/2005 | Sharkey et al. |
| 6,878,167 B2 | 4/2005 | Ferree |
| 6,883,520 B2 | 4/2005 | Lambrecht et al. |
| 6,893,462 B2 | 5/2005 | Buskirk et al. |
| 6,896,675 B2 | 5/2005 | Leung et al. |
| 6,913,622 B2 | 7/2005 | Gjunter |
| 6,923,823 B1 | 8/2005 | Bartlett et al. |
| 6,932,833 B1 | 8/2005 | Sandoval et al. |
| 6,936,070 B1 | 8/2005 | Muhanna |
| 6,936,072 B2 | 8/2005 | Lambrecht et al. |
| 6,960,215 B2 | 11/2005 | Olson, Jr. et al. |
| 6,964,674 B1 | 11/2005 | Matsuura et al. |
| 6,966,910 B2 | 11/2005 | Ritland |
| 6,966,931 B2 | 11/2005 | Huang |
| 6,969,404 B2 | 11/2005 | Ferree |
| 6,972,027 B2 | 12/2005 | Fallin et al. |
| 6,974,479 B2 | 12/2005 | Trieu |
| 6,980,862 B2 | 12/2005 | Fredricks et al. |
| 7,004,970 B2 | 2/2006 | Cauthen |
| 7,033,393 B2 | 4/2006 | Gainor et al. |
| 7,037,334 B1 | 5/2006 | Hlavka et al. |
| 7,128,073 B1 | 10/2006 | Van Der Burg |
| 2002/0077701 A1 | 6/2002 | Kuslich |
| 2002/0082698 A1 | 6/2002 | Parenteau et al. |
| 2002/0147461 A1 | 10/2002 | Aldrich |
| 2003/0040796 A1 | 2/2003 | Ferree |
| 2003/0074075 A1 | 4/2003 | Thomas |
| 2003/0195514 A1 | 10/2003 | Trieu |
| 2004/0039392 A1 | 2/2004 | Trieu |
| 2004/0054414 A1 | 3/2004 | Trieu |
| 2004/0092969 A1 | 5/2004 | Kumar |
| 2004/0097980 A1 | 5/2004 | Ferree |
| 2004/0138703 A1 | 7/2004 | Alleyne |
| 2004/0210310 A1 | 10/2004 | Trieu |
| 2004/0260397 A1 | 12/2004 | Lambrecht et al. |
| 2005/0033440 A1 | 2/2005 | Lambrecht et al. |
| 2005/0038519 A1 | 2/2005 | Lambrecht et al. |
| 2005/0060038 A1 | 3/2005 | Lambrecht et al. |
| 2006/0129156 A1 | 6/2006 | Cauthen |
| 2006/0161258 A1 | 7/2006 | Cauthen |
| 2006/0167553 A1 | 7/2006 | Cauthen |
| 2006/0173545 A1 | 8/2006 | Cauthen |
| 2006/0195193 A1 | 8/2006 | Bloemer |
| 2006/0247776 A1 | 11/2006 | Kim |
| 2006/0282167 A1 | 12/2006 | Lambrecht |
| 2007/0067040 A1 | 3/2007 | Ferree |
| 2007/0100349 A1 | 5/2007 | O'Neil |

FOREIGN PATENT DOCUMENTS

| | | |
|---|---|---|
| DE | 4323595 C | 7/1994 |
| GB | 2054383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 8/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |

OTHER PUBLICATIONS

Ahlgren, B.D., MD., et al., "Effect of Anular Repair on the Healing Strength of the Intervertebral Disc," *Spine* 25(17):2165-2170 (2000).

Cauthen, Joseph, Draft Abstract entitled "Microsurgical Annular Reconstruction (Annuloplasty) Following Lumbar Microdiscectomy: Preliminary Report of a New Technique" from abstracts@neurosurgery.org. Sep. 4, 1998.

Cauthen, Joseph C., MD., "Microsurgical Annular Reconstruction (Annuloplasty) Following Lumbar Microdiscectomy: Preliminary Report of a New Technique," Abstract for Poster Presentation, AANS/CNS Section on Disorders of the Spine and Peripheral Nerves Annual Meeting (1999).

Cauthen, Joseph C., "Annulotomy Study, Preliminary Results: Updated Feb. 1999 for all procedures with at least one-year follow-up" (Table), Feb. 8, 1999.

Lehmann, Thomas R., M.D., et al., "Refinements in Technique for Open Lumbar Discectomy," International Society for the Study of the Lumbar Spine (1997).

Mineiro, J., et al., "Dynamic Neutralization With Dynesys Review of 113 Cases with More than 1 Year Follow-Up," *Spineweek 2004*, Porto, Portugal May 30 to Jun. 5, 2004, Abstract B19, p. 181.

Ordway, N.R., et al., "Failure Properties of a Hydrogel Nucleus in the Intervertebral Disc," *North American Spine Society*, pp. 168-169 (1997).

Osti, O.L., et al., "Annular Tears and Disc Degeneration in the Lumbar Spine," *The Journal of Bone and Joint Surgery* 74-B(5):678-82 (1992).

Panjabi, Manohar, PhD., et al., "Intrinsic Disc Pressure as a Measure of Integrity of the Lumbar Spine," *Spine* 13(8):913-17 (1988).

Patent Cooperation Treaty. "International Search Report,".

Ray, Charles D., "Prosthetic Disc Nucleus Implants: Update," *North American Spine Society 13th Annual Meeting*, p. 252.

Yasargil, M.G., "Microsurgical Operation of Herniated Lumbar Disc," *Lumbar Disc Adult Hydrocephalus*, p. 81 (1977).
International Search Report for PCT/US06/16292 (PCT counterpart of related application) dated Apr. 28, 2006, Blaine R. Copenheaver.
Copending U.S. Appl. No. 10/075,615, filed Feb. 15, 2002 by Cauthen.
Copending U.S. Appl. No. 10/085,040, filed Mar. 1, 2002 by Cauthen.
Copending U.S. Appl. No. 10/352,981, filed Jan. 29, 2003 by Cauthen.
Copending U.S. Appl. No. 10/394,061, filed Mar. 24, 2003 by Cauthen.
Copending U.S. Appl. No. 10/394,266, filed Mar. 24, 2003 by Cauthen.
Copending U.S. Appl. No. 10/394,008, filed Mar. 24, 2003 by Cauthen.
Copending U.S. Appl. No. 10/392,733, filed Mar. 19, 2003 by Cauthen.
Copending U.S. Appl. No. 10/985,735, filed Nov. 10, 2004 by Cauthen.
Copending U.S. Appl. No. 11/120,750, filed May 3, 2005 by Cauthen et al.
Copending U.S. Appl. No. 11/235,764, filed Sep. 26, 2005 by Wales.
Copending U.S. Appl. No. 11/386,642, filed Mar. 23, 2006 by Cauthen et al.
Copending U.S. Appl. No. 11/398,583, filed Apr. 6, 2006 by Cauthen.
Copending U.S. Appl. No. 11/410,420, filed Apr. 25, 2006 by Cauthen.
Copending U.S. Appl. No. 11/313,738, filed Dec. 22, 2005 by Cauthen.
Copending U.S. Appl. No. 11/351,657, filed Feb. 10, 2006 by Cauthen.
Copending U.S. Appl. No. 11/355,426, filed Feb. 16, 2006 by Cauthen.
Copending U.S. Appl. No. 11/376,301, filed Mar. 16, 2006 by Cauthen.
Copending U.S. Appl. No. 11/350,843, filed Feb. 10, 2006 by Cauthen et al.
Copending U.S. Appl. No. 11/386,616, filed Mar. 23, 2006 by Cauthen et al.
Copending U.S. Appl. No. 11/512,251, filed Aug. 30, 2006 by Cauthen et al.
Copending U.S. Appl. No. 11/558,034, filed Nov. 9, 2006 by Cauthen.
Copending U.S. Appl. No. 11/841,513, filed Aug. 20, 2007 by Cauthen.
Copending U.S. Appl. No. 11/521,473, filed Sep. 15, 2006 by Cauthen.
Copending U.S. Appl. No. 11/556,878, filed Nov. 6, 2006 by Cauthen et al.
Copending U.S. Appl. No. 11/557,997, filed Nov. 9, 2006 by Cauthen et al.
Copending U.S. Appl. No. 11/608,480, filed Dec. 8, 2006 by Cauthen et al.
Copending U.S. Appl. No. 11/622,631, filed Jan. 12, 2007 by Cauthen et al.
Copending U.S. Appl. No. 11/686,599, filed Mar. 15, 2007 by Cauthen et al.
Copending U.S. Appl. No. 11/527,903, filed Sep. 26, 2006 by Cauthen et al.
US 6,447,535, 09/2002, Jacobs et al. (withdrawn)

\* cited by examiner

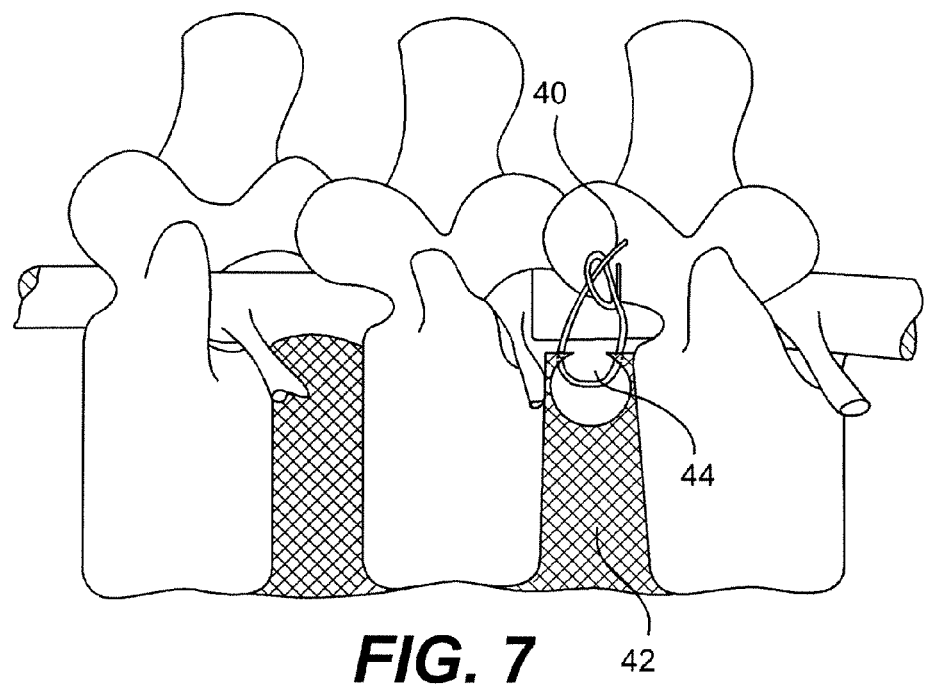
FIG. 7
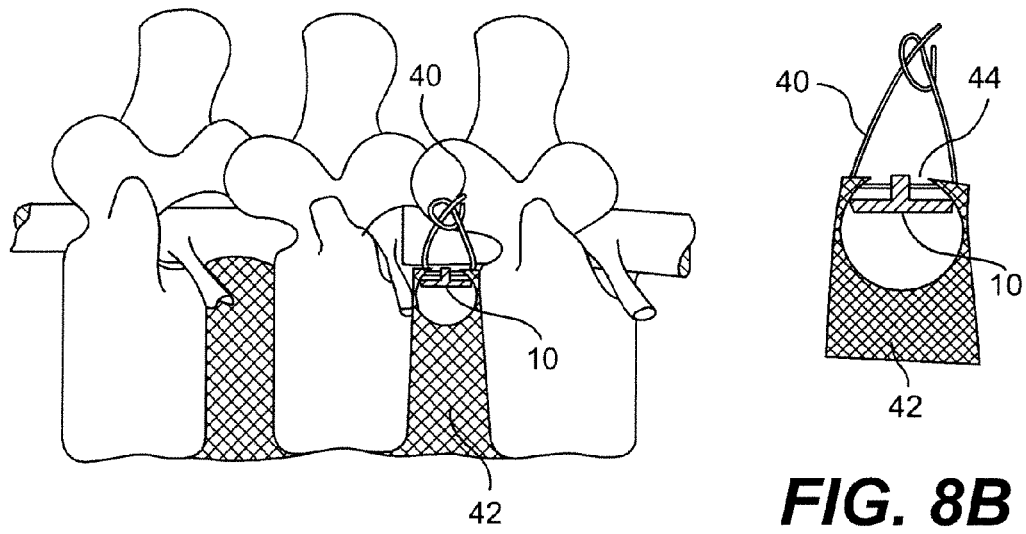
FIG. 8A
FIG. 8B

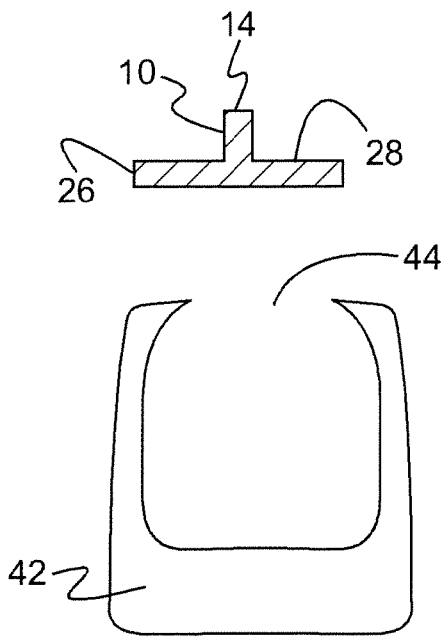
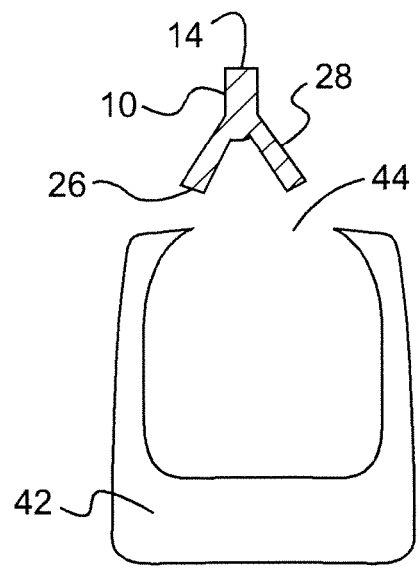
FIG. 11A          FIG. 11B
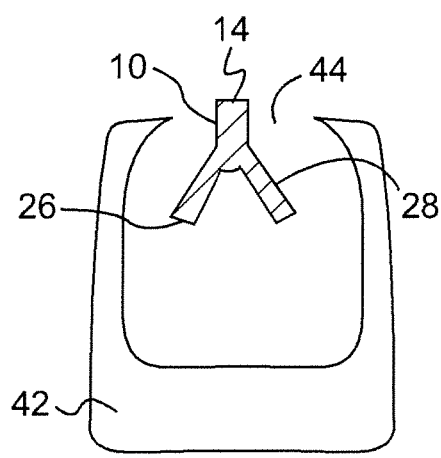
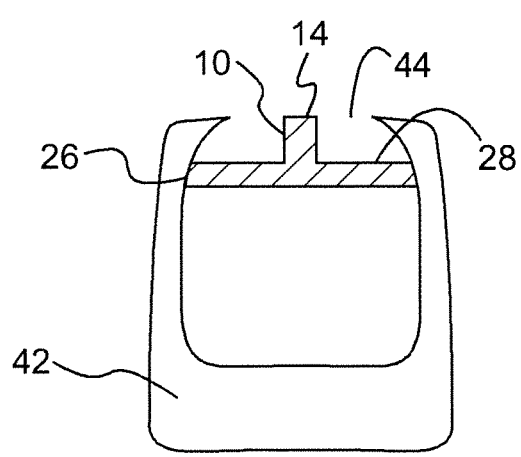
FIG. 11C          FIG. 11D

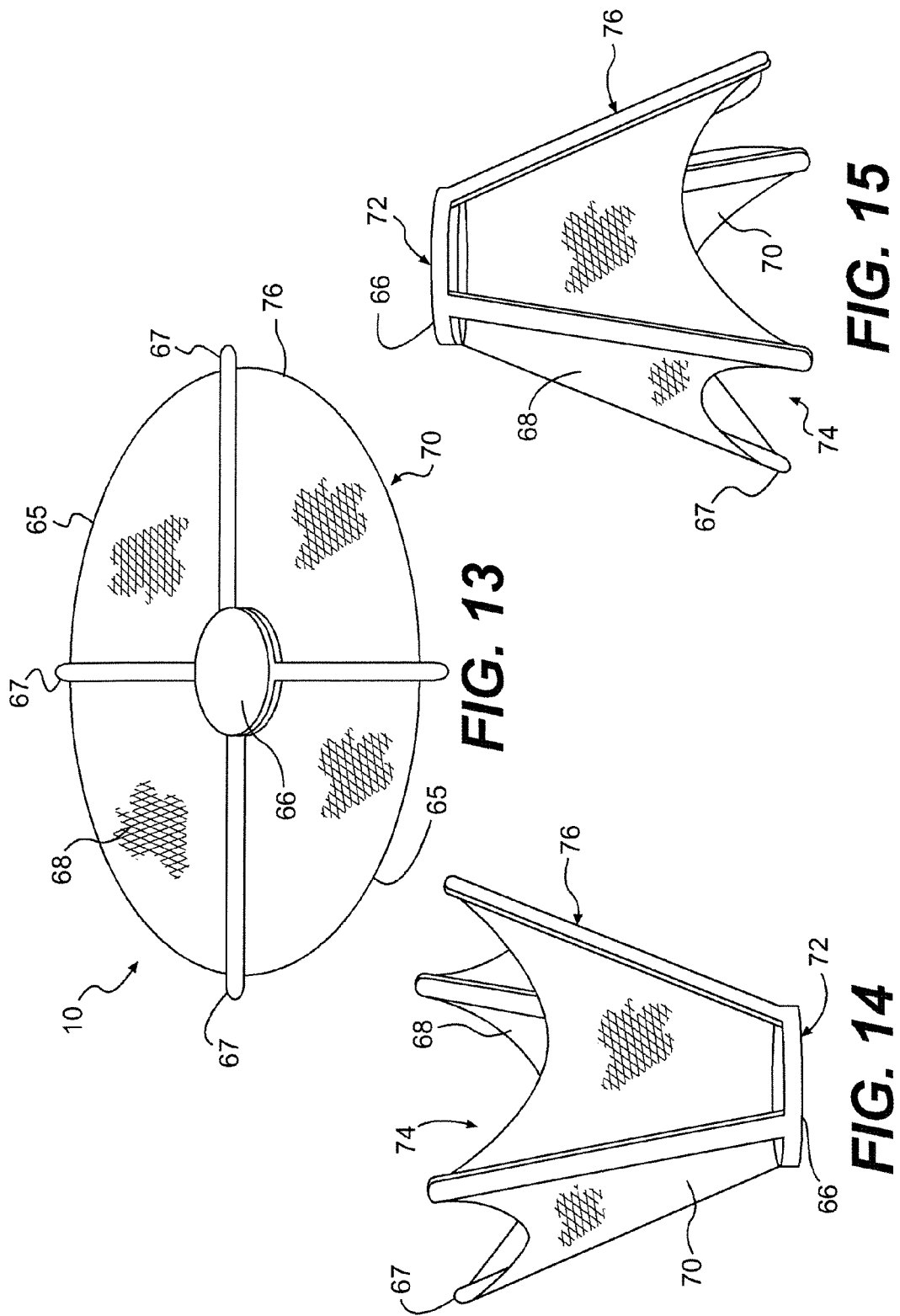

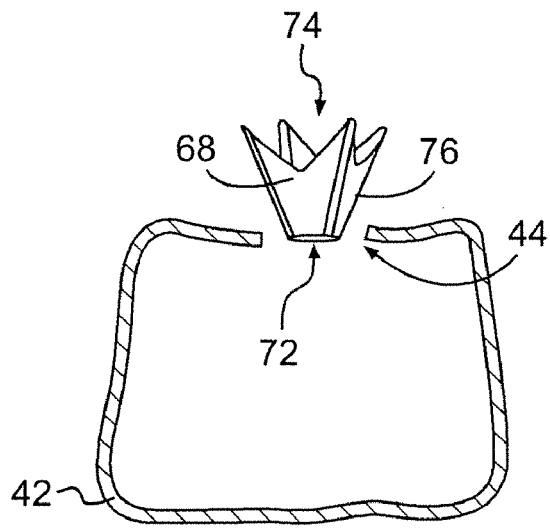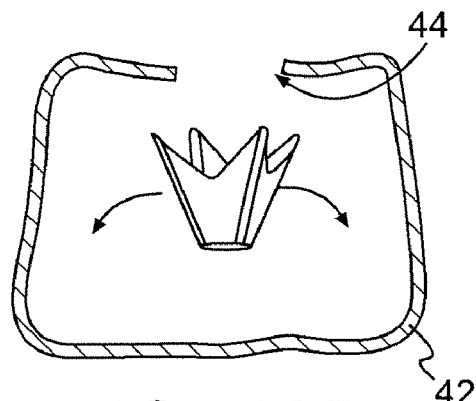
FIG. 16A  FIG. 16B
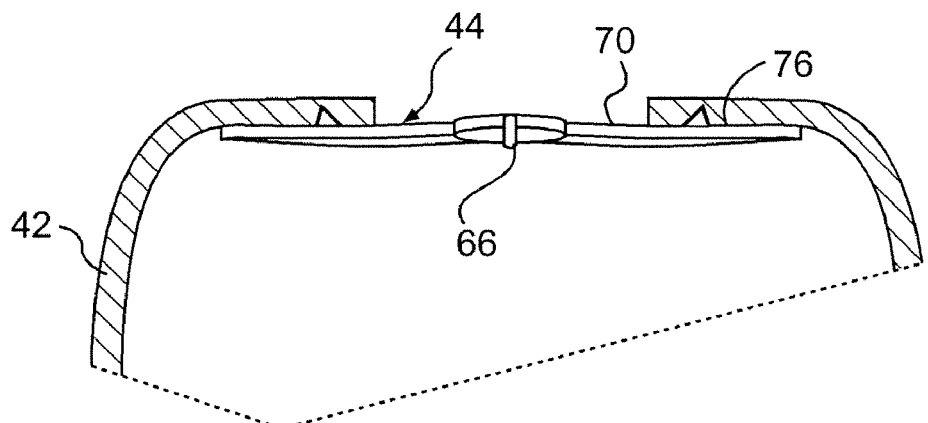
FIG. 16C

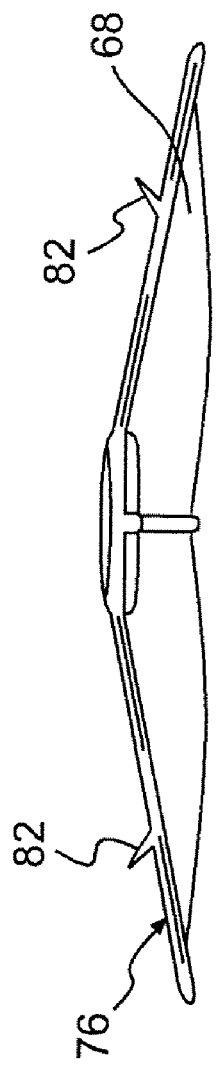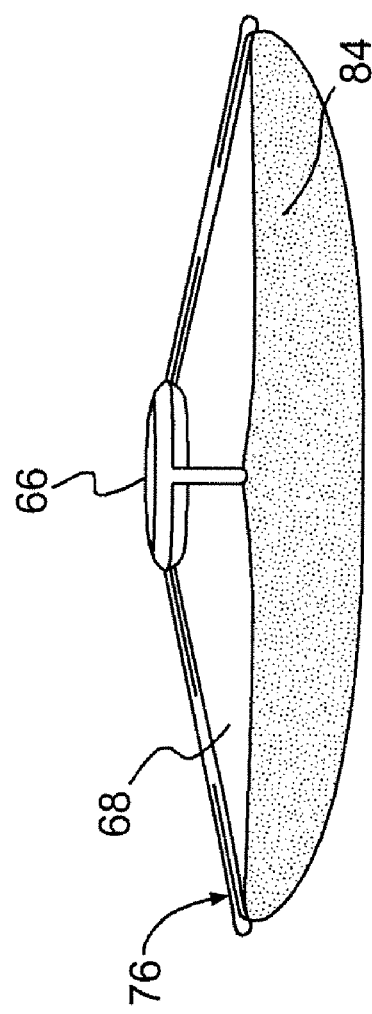

HERNIATED DISC

DISC, POST-DISCECTOMY

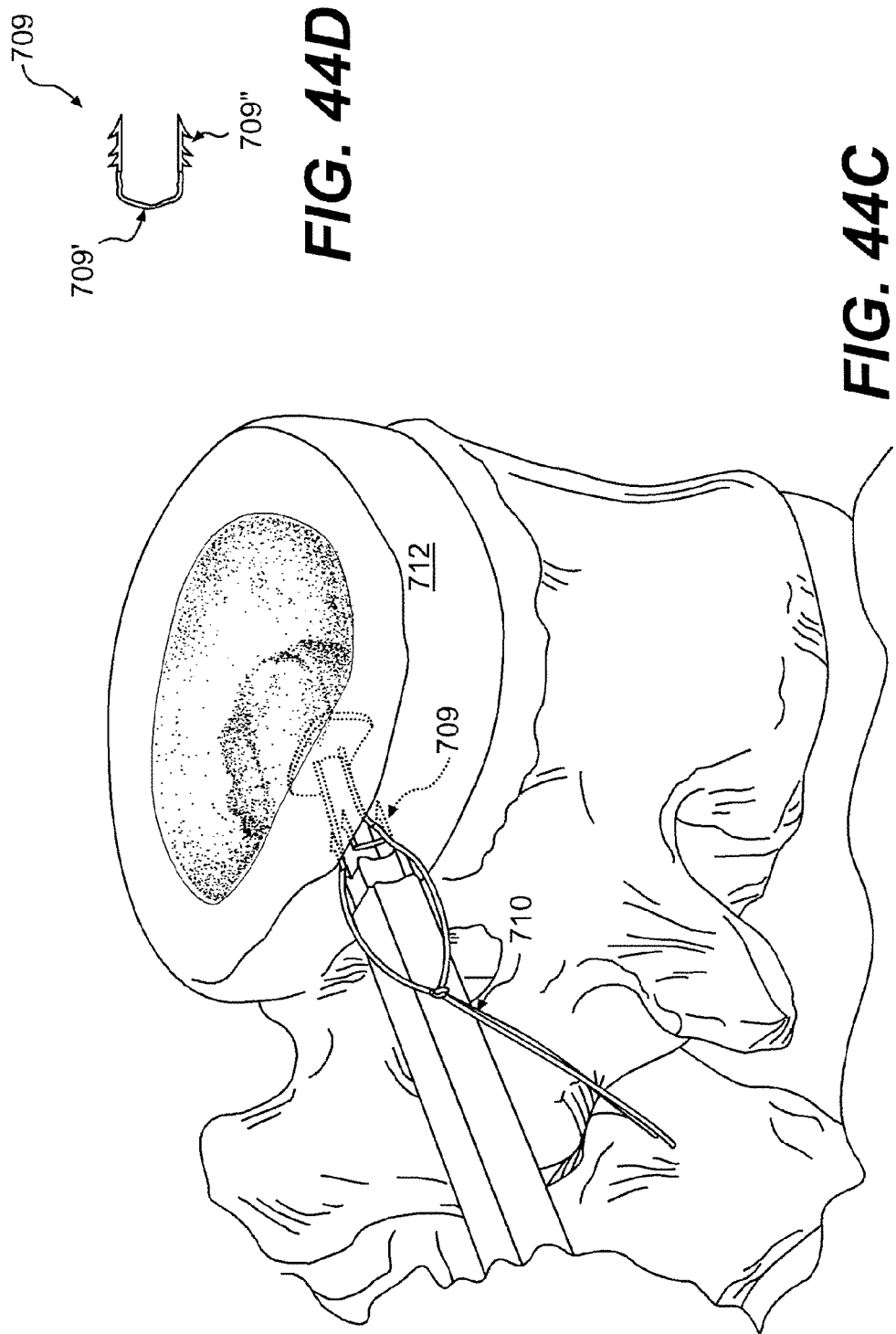

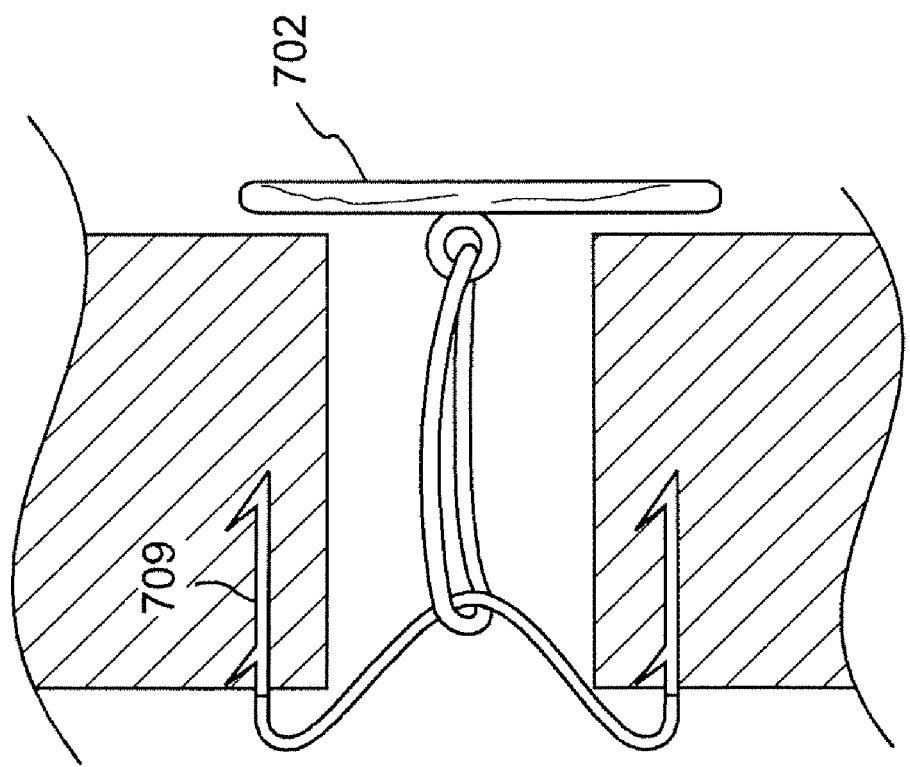
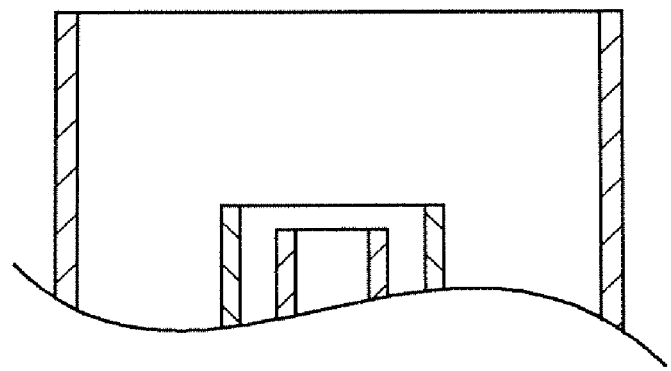
FIG. 46C

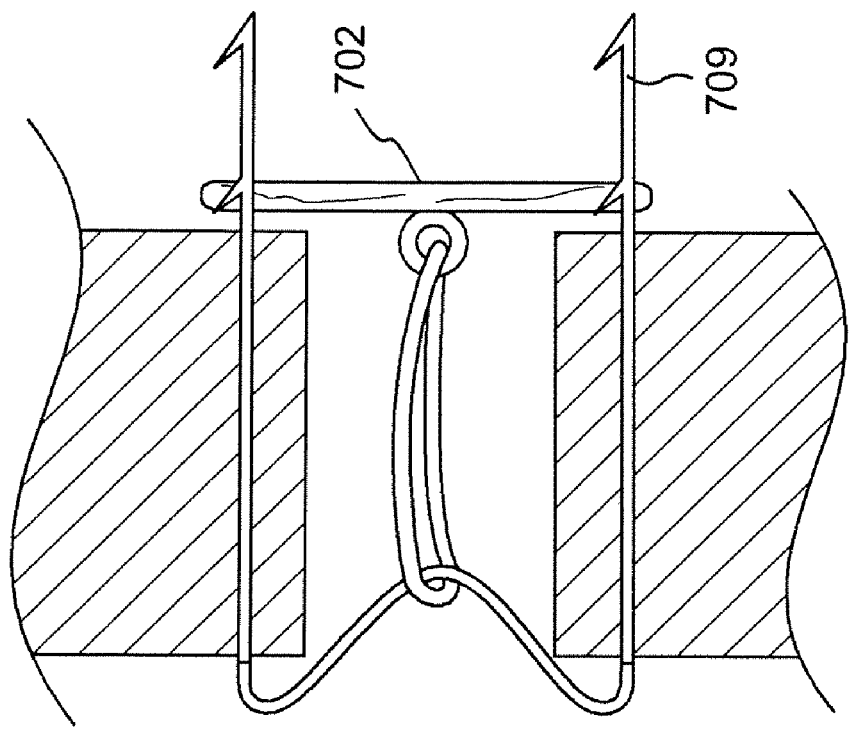
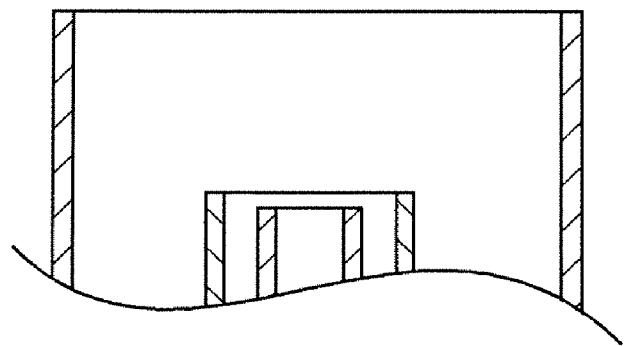
FIG. 50C

SPINAL DISC ANNULUS RECONSTRUCTION METHOD AND DEFORMABLE SPINAL DISC ANNULUS STENT

CROSS-REFERENCE TO A RELATED APPLICATION

This application is a continuation of U.S. application Ser. No. 11/386,642, filed Mar. 23, 2006, now pending, which is continuation of U.S. application Ser. No. 10/133,339, filed Apr. 29, 2002, now U.S. Pat. No. 7,052,516 issued on May 30, 2006, which claims the benefit of U.S. Provisional Application No. 60/309,105, filed Jul. 31, 2001; and which is a continuation-in-part of U.S. patent application Ser. No. 10/075,615, filed on Feb. 15, 2002, now abandoned which is a continuation-in-part of Ser. No. 09/947,078, filed Sep. 5, 2001, now U.S. Pat. No. 6,592,625 which is a continuation of U.S. patent application Ser. No. 09/484,706, filed Jan. 18, 2000, now abandoned, which claims the benefit of U.S. Provisional Application No. 60/160,710, filed Oct. 20, 1999. The entire contents of each of the above are incorporated herein by reference.

FIELD OF THE INVENTION

The invention generally relates to methods and implantable medical devices for the closure, sealing and/or repair of an aperture in the intervertebral disc annulus. The term "aperture" refers to a hole in the annulus that is a result of a surgical incision into the intervertebral disc annulus, or the consequence of a naturally occurring tear (rent). The invention generally relates to surgical devices and methods for intervertebral disc wall repair or reconstruction. The invention further relates to an annular repair device, or stent, for annular disc repair. These stents can be of natural or synthetic materials. The effects of said reconstruction are restoration of disc wall integrity and reduction of the failure rate (3-21%) of a common surgical procedure (disc fragment removal or discectomy). This surgical procedure is performed about 390,000 times annually in the United States.

BACKGROUND OF THE INVENTION

The spinal column is formed from a number of bony vertebrae, which in their normal state are separated from each other by intervertebral discs. These discs are comprised of the annulus fibrosus, and the nucleus pulposus, both of which are soft tissue. The intervertebral disc acts in the spine as a crucial stabilizer, and as a mechanism for force distribution between adjacent vertebral bodies. Without the disc, collapse of the intervertebral space occurs in conjunction with abnormal joint mechanics and premature development of arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of loose tissue, having about 85% water content, which moves about during bending from front to back and from side to side, The aging process contributes to gradual changes in the intervertebral discs. The annulus loses much of its flexibility and resilience, becoming more dense and solid in composition. The aging annulus may also be marked by the appearance or propagation of cracks or fissures in the annular wall. Similarly, the nucleus desiccates, increasing viscosity and thus losing its fluidity. In combination, these features of the aged intervertebral discs result in less dynamic stress distribution because of the more viscous nucleus pulposus, and less ability to withstand localized stresses by the annulus fibrosus due to its desiccation, loss of flexibility and the presence of fissures. Fissures can also occur due to disease or other pathological conditions. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

The surgical standard of care for treatment of herniated, displaced or ruptured intervertebral discs is fragment removal and nerve decompression without a requirement to reconstruct the annular wall. While results are currently acceptable, they are not optimal. Various authors report 3.1-21% recurrent disc herniation, representing a failure of the primary procedure and requiring re-operation for the same condition. An estimated 10% recurrence rate results in 39,000 re-operations in the United States each year.

An additional method of relieving the symptoms is thermal annuloplasty, involving the heating of sub-annular zones in the non-herniated painful disc, seeking pain relief, but making no claim of reconstruction of the ruptured, discontinuous annulus wall.

Some have also suggested that the repair of a damaged intervertebral disc might include the augmentation of the nucleus pulposus, and various efforts at nucleus pulposus replacement have been reported. The present invention is directed at the repair of the annulus, whether or not a nuclear augmentation is also warranted.

In addition, there has been experimentation in animals to assess various surgical incisions with and without the direct surgical repair of the annulus. These studies were performed on otherwise healthy animals and involved no removal or augmentation of nucleus pulposus. The authors of these experiments conclude that direct repair of the annulus does not influence the healing of the disc.

There is currently no known method of annulus reconstruction, either primarily or augmented with an annulus stent.

BRIEF SUMMARY OF THE INVENTION

The present invention provides methods and related materials for reconstruction of the disc wall in cases of displaced, herniated, ruptured, or otherwise damaged intervertebral discs. In accordance with the invention, a method is disclosed for intervertebral disc reconstruction for treating a disc having an aperture in the wall of the annulus fibrosis, wherein the aperture provides a path for the migration of nucleus pulposus from the subannular space, the method including the steps of providing an expandable patch having a first configuration dimensioned to pass through the aperture and a second expanded configuration having at least one dimension at least as large as the aperture and having at least one dimension larger than a corresponding dimension in said first configuration; inserting the patch through the aperture into the subannular space when the device is in the first collapsed configuration; and causing or allowing the patch to expand in the subannular space into the second expanded configuration to bridge the aperture, thereby occluding the aperture and preventing the migration of nucleus pulposus therethrough.

The objects and various advantages of the invention will be apparent in consideration of the description which follows. In general, the implantable medical device is placed, positioned, and affixed to the annulus to reduce re-extrusion of the nucleus through the aperture by: acting as a mechanical barrier; restoring the natural integrity of the wall of the annulus; and, promoting the healing of the annulus through the reapproximation of disc wall tissue. Increased integrity and faster and/or more thorough healing of the aperture is intended to reduce future recurrence of herniation of the disc nucleus from the intervertebral disc, and the recurrence of resulting back pain. In addition, it is believed that the repair of the aperture could promote enhanced biomechanics and reduce the possibility of intervertebral disc height collapse and segmental instability, thus resulting in a decrease in the recurrence of back pain after a surgical procedure.

Moreover, the repair of the aperture with the reduction of the re-extrusion of the nucleus may also advantageously reduce adhesion formation surrounding the nerve roots. The nuclear material of the disc is toxic to the nerves and is believed to cause increased inflammation surrounding the nerves, which in turn can cause increased scar formation (adhesions or epidural fibrosis) upon healing. Adhesions created around the nerve roots can cause continued back pain. Any reduction in adhesion formation is believed to reduce future recurrence of pain.

One of the objects of the present inventions is to act as a mechanical barrier to the extrusion of the nucleus from the disc space, add mechanical integrity to the annulus and the tissue surrounding the aperture, and to promote faster and a more complete healing of the aperture.

Although much of the discussion is directed toward the repair of the intervertebral disc after a surgical procedure, such as discectomy (a surgical procedure performed to remove herniated fragments of the disc nucleus), it is contemplated that the device could be used in other procedures that involve incisions into the annulus of the intervertebral disc. An example of another procedure that could require a repair technique involves the replacement of the nucleus—nucleus replacement—with an implantable nucleus to replace the functioning of the natural nucleus when it is degenerated. The object of the invention in this case would be similar in that the repair would maintain the replacement nucleus within the disc space.

According to the invention, a sub-annular patch/stent can be employed to repair an intervertebral disc annulus. In its simplest form, the repair of the annulus involves the placement and fixation of a fascial autograft patch to the subannular space which can additionally employ two or more sutures, while re-approximating the tissues surrounding the aperture. The invention, through involvement of the sub-annular space and wall for the repair of the aperture has several advantages over the prior art, for example, sealing the aperture only on the outer surface or sealing the aperture only within the aperture. The first advantage of a repair that involves the sub-annular surface derives itself from the physical nature of a circular (or an elliptical) compressed chamber with a radius, like an intervertebral disc. Sealing the inside wall has the inherent advantage of being at a smaller radius of curvature versus the outer wall and thus, according to LaPlace's Law, the patch would be subjected to lower stresses at any given pressure, all else held equal.

Another advantage of utilizing the inner surface to accomplish sealing is that the natural pressure within the disc can enhance the sealing of the device against the inner wall of the disc space. Conversely, if the repair is performed on the outer surface of the annulus there is an inherent risk of leakage around the periphery of the device, with the constant exposure to the pressure of the disc.

Another advantage of the present invention over the prior art in utilizing the inner surface of the annulus is the reduction of the risk of having a portion of the device protruding from the exterior surface of the annulus. Device materials protruding from the exterior of the annulus pose a risk of damaging the nerve root and/or spinal canal which are in close proximity. Damage to these structures can result in continued pain, incontinence, bowel dysfunction and paralysis.

The present invention also incorporates the concept of pulling the tissues together that surround the aperture, the inner surface, and the outer surface of the annulus to help increase the integrity of the repair.

An example of the technique and placement of the device according to the invention is as follows:

1. An aperture is created measuring approximately, for example, 6 mm×2 mm in the wall of the annulus after performing a discectomy procedure in which a portion of the nucleus is also removed from the disc space, as shown in FIGS. 32*a*, 32*b*, 33*a* and 33*b*.

2. Two or more sutures are passed through the upper and lower surfaces of the aperture and they are pushed within the intervertebral disc space to create a "sling" to receive the fascial autograft as shown for example in FIG. 34

3. A piece of para-spinal fascial tissue is removed from the patient measuring approximately, for example, 10 mm×5 mm.

4. The autograft is folded and compressed to pass through the aperture in the annulus, as shown for example in FIG. 35

5. The autograft takes a second shape, within the annulus that is uncompressed and oriented to be in proximity of the subannular wall of the annulus, within the sling, as shown for example in FIG. 36. The autograft may be inserted entirely into the subannular space, or a portion may extend into the rent as depicted in FIG. 36.

6. The sutures are tightened, as shown for example in FIG. 37, thus tightening the sling surrounding the autograft, to bring the autograft in close proximity with the subannular wall, while providing tension to bring the patch at the subannular surface together with the outer surface of the annular wall, thus creating increased integrity of the annulus surrounding the aperture, as well as causing the autograft to take a second shape that is larger than the aperture. Furthermore, the tightening, and eventual tying of the sutures also promotes the re-approximation of the tissue at the outer surface of the annulus and within the aperture.

7. The sutures are tied and the ends of the sutures are cut.

8. A piece of autograft fat tissue may be placed over the discectomy site for the prevention of adhesion formation, a typical surgical technique.

9. Standard surgical techniques are utilized to close the access site of the surgical procedures.

Several devices according to the present invention can be used to practice the above illustrative inventive steps to accomplish the sealing and/or repair of the intervertebral disc. In each of the representative devices described herein, there is: an expandable patch/stent (note: patch, stent and device are used interchangeably) that has, in use, at least a portion of the device in proximity to the sub-annular space of the intervertebral disc annulus; a means to affix the patch to stay in proximity with the annulus; a means to draw the patch and the annular tissue together and fasten in tension; and a means to help reduce the relative motion of the surfaces of the aperture after fixation, and thus promote healing. According to one feature and object of the present invention, close approximation of tissue, while reducing the motion of the surfaces, provides the optimal environment for healing.

The concepts disclosed hereinbelow accomplish these objectives, as well as advantageously additionally incorporating design elements to reduce the number of steps (and time), and/or simplify the surgical technique, and/or reduce the risk of causing complications during the repair of the intervertebral disc annulus. In addition, it is an objective of the following devices to become incorporated by the surrounding tissues, or to act as a scaffold in the short-term (3-6 months) for tissue incorporation.

In an exemplary embodiment, one or more mild biodegradable surgical sutures can be placed at about equal distances along the sides of a pathologic aperture in the ruptured disc wall (annulus) or along the sides of a surgical incision in the annular wall, which may be weakened or thinned.

Sutures are then tied in such fashion as to draw together the sides of the aperture, effecting reapproximation or closure of the opening, to enhance natural healing and subsequent reconstruction by natural tissue (fibroblasts) crossing the now surgically narrowed gap in the disc annulus.

A 25-30% reduction in the rate of recurrence of disc nucleus herniation through this aperture has been achieved using this method.

In another exemplary embodiment, the method can be augmented by creating a subannular barrier in and across the aperture by placement of a patch of human muscle fascia (muscle connective tissue) or any other autograft, allograft, or xenograft acting as a bridge or a scaffold, providing a platform for traverse of fibroblasts or other normal cells of repair existing in and around the various layers of the disc annulus, prior to closure of the aperture.

A 30-50% reduction in the rate of recurrence of disc herniation has been achieved using the aforementioned fascial augmentation with this embodiment.

Having demonstrated that human muscle fascia is adaptable for annular reconstruction, other biocompatible membranes can be employed as a bridge, stent, patch or barrier to subsequent migration of the disc nucleus through the aperture. Such biocompatible materials may be, for example, medical grade biocompatible fabrics, biodegradable polymeric sheets, or form fitting or non-form fitting fillers for the cavity created by removal of a portion of the disc nucleus pulposus in the course of the disc fragment removal or discectomy. The prosthetic material can be placed in and around the intervertebral space, created by removal of the degenerated disc fragments.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

FIG. 7 shows a primary closure of an opening in the disc annulus.

FIGS. 8A-8B show a primary closure with a stent.

FIGS. 11A-11D show an annulus stent being inserted into and expanded within the disc annulus.

FIG. 13 shows a perspective view of a further illustrative embodiment of an annulus stent.

FIG. 14 shows a first collapsed view of the annulus stent of FIG. 13.

FIG. 15 shows a second collapsed view of the annulus stent of FIG. 13.

FIGS. 16A-16C show the annulus stent of FIG. 13 being inserted into the disc annulus.

FIG. 20 shows an expanded annulus stent with barbs on the radial extension.

FIG. 21 shows a still further illustrative embodiment of an annulus stent with a compressible core.

FIGS. 44A-G show a still further illustrative embodiment of an introduced and expanded annulus stent/patch being fixated and the aperture reapproximated.

FIGS. 46A-C schematically depict the cinch line of FIG. 45 being fixated through use of a surgical staple device.

FIGS. 50A-C schematically depict the cinch line of FIG. 49 being fixated through use of a barbed surgical staple device that penetrates the patch/stent.

DETAILED DESCRIPTION OF THE INVENTION

Reference will now be made in detail to an illustrative embodiment of the invention, which appears in the accompanying drawings. Wherever possible, the same reference numbers will be used throughout the drawings to refer to the same or like parts.

In one embodiment of the present invention, as shown in FIG. 7, a damaged annulus 42 is repaired by use of surgical sutures 40. One or more surgical sutures 40 are placed at about equal distances along the sides of a pathologic aperture 44 in the annulus 42. Reapproximation or closure of the aperture 44 is accomplished by tying the sutures 40 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 40 are biodegradable, but permanent non-biodegradable may be utilized.

Additionally, to repair a weakened or thinned wall of a disc annulus 42, a surgical incision can be made along the weakened or thinned region of the annulus 42 and one or more surgical sutures 40 can be placed at about equal distances laterally from the incision. Reapproximation or closure of the incision is accomplished by tying the sutures 40 so that the sides of the incision are drawn together. The reapproximation or closure of the incision enhances the natural healing and subsequent reconstruction by the natural tissue crossing the now surgically narrowed gap in the annulus 42. Preferably, the surgical sutures 40 are biodegradable, but permanent non-biodegradable materials may be utilized.

In an alternative embodiment, the method can be augmented by the placement of a patch of human muscle fascia or any other autograft, allograft or xenograft in and across the aperture 44. The patch acts as a bridge in and across the aperture 44, providing a platform for traverse of fibroblasts or other normal cells of repair existing in and around the various layers of the disc annulus 42, prior to closure of the aperture 44.

In a further embodiment, as shown in FIGS. 8A-B a biocompatible membrane can be employed as an annulus stent 10, being placed in and across the aperture 44. The annulus stent 10 acts as a bridge in and across the aperture 44, providing a platform for a traverse of fibroblasts or other normal cells of repair existing in and around the various layers of the disc annulus 42, prior to closure of the aperture 44. In some embodiments the device, stent or patch can act as a scaffold to assist in tissue growth that healingly scars the annulus.

Figure 1:
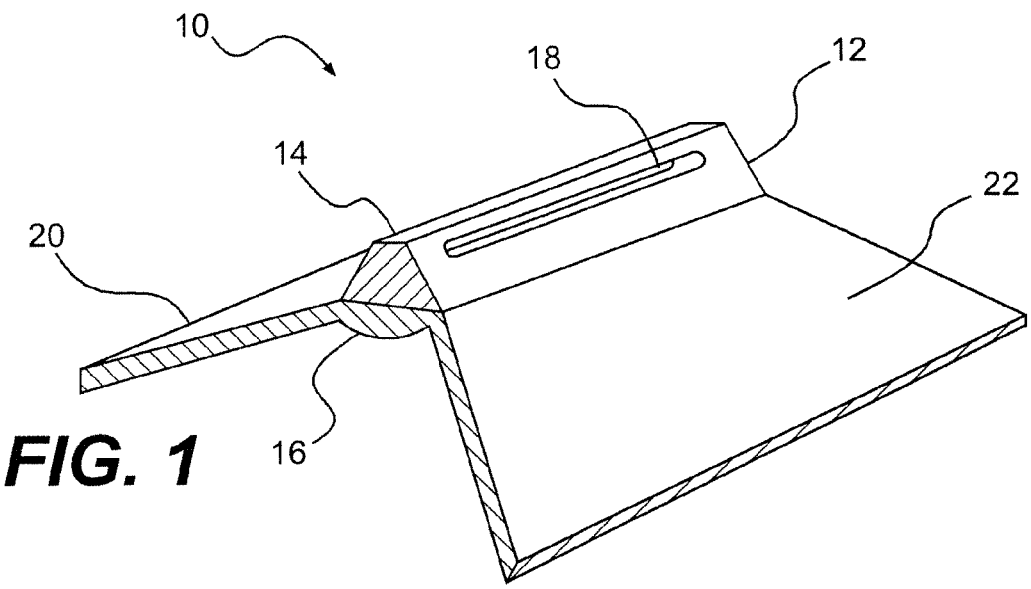
FIG. 1 shows a perspective view of an illustrative embodiment of an annulus stent.
Figure 2:
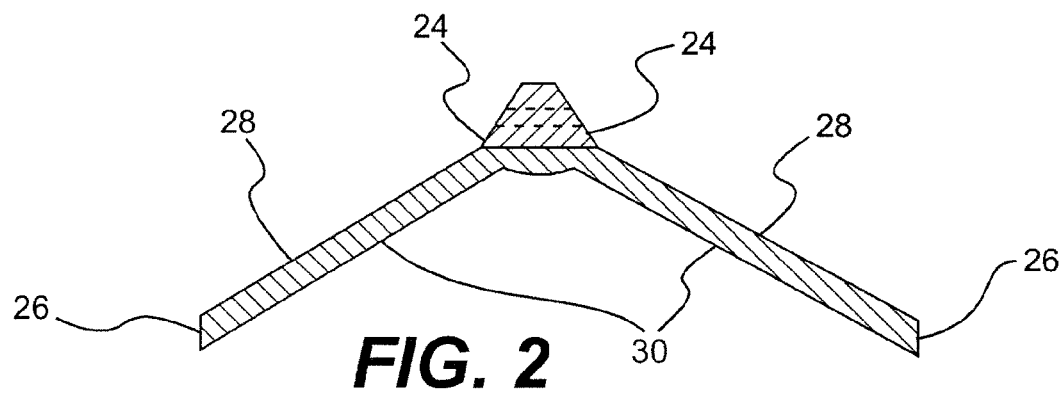
FIG. 2 shows a front view of the annulus stent of FIG. 1.
Figure 3:
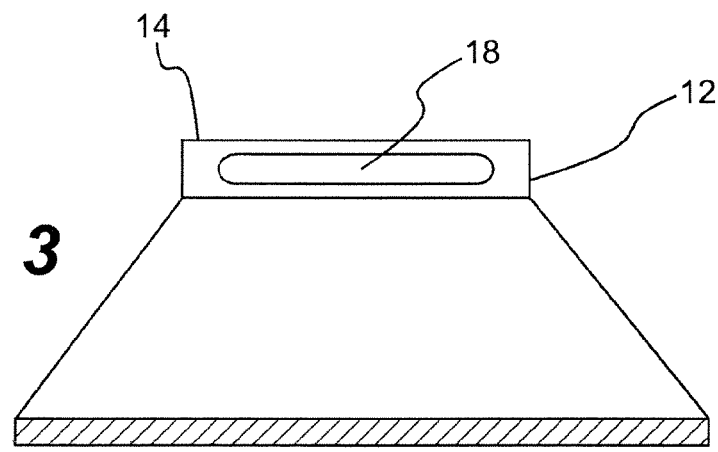
FIG. 3 shows a side view of the annulus stent of FIG. 1.

In an illustrative embodiment, as shown in FIGS. 1-3, the annulus stent 10 comprises a centralized vertical extension 12, with an upper section 14 and a lower section 16. The centralized vertical extension 12 can be trapezoid in shape through the width and may be from about 8 mm-12 mm in length.

Figure 4A:
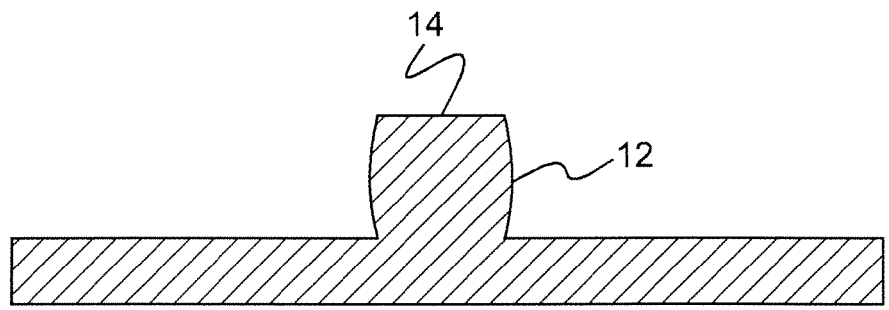
FIGS. 4A-4C show a front view of alternative illustrative embodiments of an annulus stent.
Figure 4B:
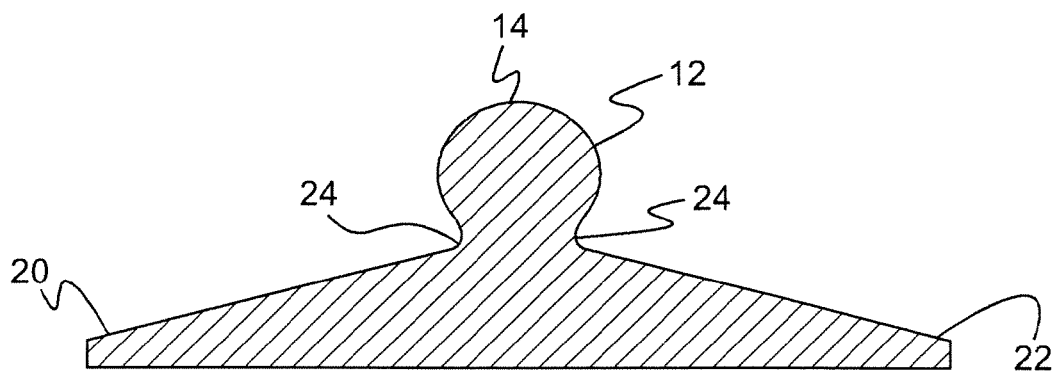
Figure 4C:
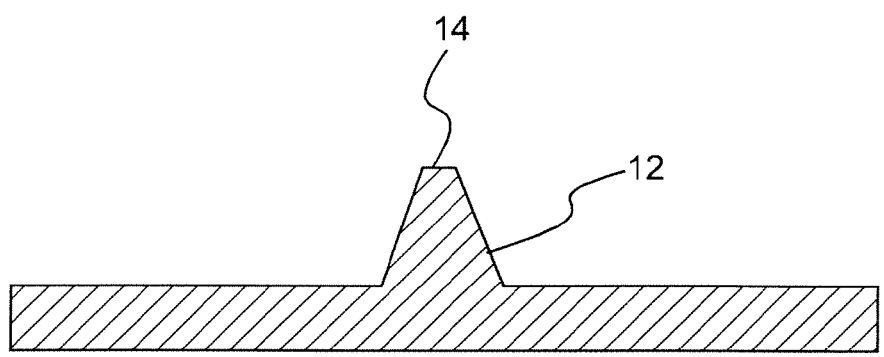

Additionally, the upper section 14 of the centralized vertical extension 12 may be any number of different shapes, as shown in FIGS. 4A through 4C, with the sides of the upper section 14 being curved or with the upper section 14 being circular in shape. Furthermore, the annulus stent 10 may contain a recess between the upper section 14 and the lower section 16, enabling the annulus stent 10 to form a compatible fit with the edges of the aperture 44.

The upper section 14 of the centralized vertical extension 12 can comprise a slot 18, where the slot 18 forms an orifice through the upper section 14. The slot 18 is positioned within the upper section 14 such that it traverses the upper section's 14 longitudinal axis. The slot 18 is of such a size and shape that sutures, tension bands, staples or any other type of fixation device known in the art may be passed through, to affix the annulus stent 10 to the disc annulus 42.

In an alternative embodiment, the upper section 14 of the centralized vertical extension 12 may be perforated. The perforated upper section 14 contains a plurality of holes that traverse the longitudinal axis of upper section 14. The perforations are of such a size and shape that sutures, tension bands, staples or any other type of fixation device known in the art may be passed through, to affix the annulus stent 10 to the disc annulus 42.

The lower section 16 of the centralized vertical extension 12 can comprise a pair of lateral extensions, a left lateral extension 20 and a right lateral extension 22. The lateral extensions 20 and 22 comprise an inside edge 24, an outside edge 26, an upper surface 28, and a lower surface 30. The lateral extensions 20 and 22 can have an essentially constant thickness throughout. The inside edge 24 is attached to and is about the same length as the lower section 16. The outside edge 26 can be about 8 mm-16 mm in length. The inside edge 24 and the lower section 16 meet to form a horizontal plane, essentially perpendicular to the centralized vertical extension 12. The upper surface 28 of the lateral extensions 20 and 22 can form an angle from about 0°-60° below the horizontal plane. The width of the annulus stent 10 may be from about 3 mm-8 mm.

Additionally, the upper surface 28 of the lateral extensions 20 and 22 may be barbed for fixation to the inside surface of the disc annulus 42 and to resist expulsion through the aperture 44.

In an alternative embodiment, as shown in FIG. 4B, the lateral extensions 20 and 22 have a greater thickness at the inside edge 24 than at the outside edge 26.

In an illustrative embodiment, the annulus stent 10 is a solid unit, formed from one or more of the flexible resilient biocompatible or bioresorbable materials well know in the art. The selection of appropriate stent materials may be partially predicated on specific stent construction and the relative properties of the material such that, after fixed placement of the stent, the repair may act to enhance the healing process at the aperture by relatively stabilizing the tissue and reducing movement of the tissue surrounding the aperture.

For example, the annulus stent 10 may be made from:

A porous matrix or mesh of biocompatible and bioresorbable fibers acting as a scaffold to regenerate disc tissue and replace annulus fibrosus as disclosed in, for example, U.S. Pat. No. 5,108,438 (Stone) and U.S. Pat. No. 5,258,043 (Stone), a strong network of inert fibers intermingled with a bioresorbable (or bioabsorbable) material which attracts tissue ingrowth as disclosed in, for example, U.S. Pat. No. 4,904,260 (Ray et al.).

a biodegradable substrate as disclosed in, for example, U.S. Pat. No. 5,964,807 (Gan at al.); or an expandable polytetrafluoroethylene (ePTFE), as used for conventional vascular grafts, such as those sold by W.L. Gore and Associates, Inc. under the trademarks GORE-TEX and PRECLUDE, or by Impra, Inc. under the trademark IMPRA.

Furthermore, the annulus, stent 10, may contain hygroscopic material for a controlled limited expansion of the annulus stent 10 to fill the evacuated disc space cavity.

Additionally, the annulus stent 10 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

Many of the materials disclosed and described above represent embodiments where the device actively promotes the healing process. It is also possible that the selection of alternative materials or treatments may modulate the role in the healing process, and thus promote or prevent healing as may be required. It is also contemplated that these modulating factors could be applied to material substrates of the device as a coating, or similar covering, to evoke a different tissue response than the substrate without the coating.

Figure 5A:
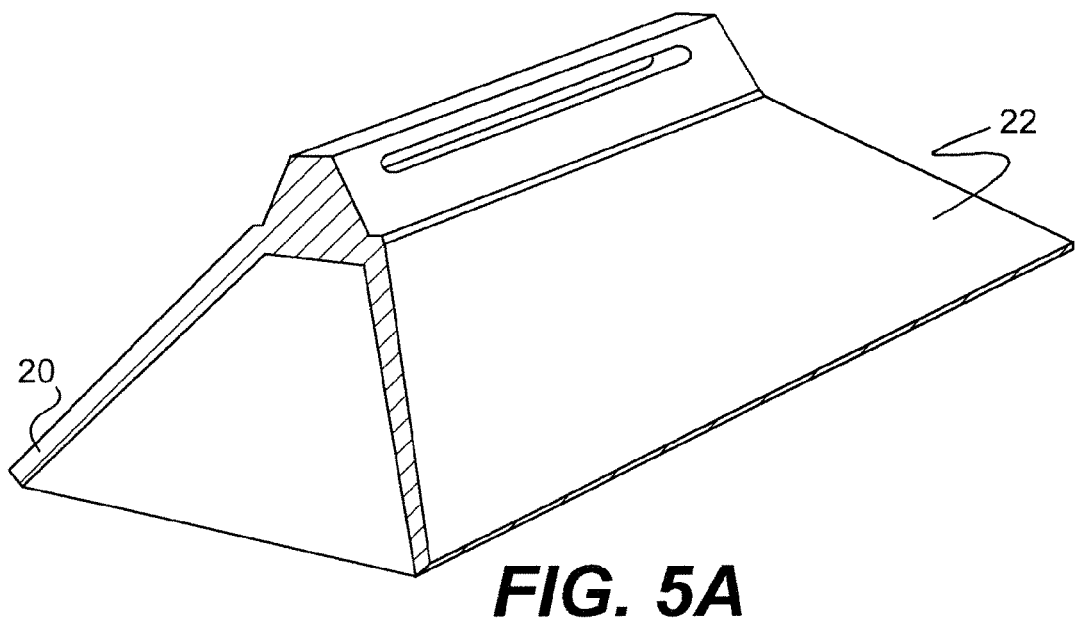
FIGS. 5A-5B show the alternative embodiment of a further illustrative embodiment of an annulus stent.

In further embodiments, as shown in FIGS. 5AB-6AB, the left and right lateral extensions 20 and 22 join to form a solid pyramid or cone. Additionally, the left and right lateral extensions 20 and 22 may form a solid trapezoid, wedge, or bullet shape. The solid formation may be a solid biocompatible or bioresorbable flexible material, allowing the lateral extensions 20 and 22 to be compressed for insertion into aperture 44, then to expand conforming to the shape of the annulus' 42 inner wall.

Alternatively, a compressible core may be attached to the lower surface 30 of the lateral extensions 20 and 22, forming a pyramid, cone, trapezoid, wedge, or bullet shape. The compressible core may be made from one of the biocompatible or bioresorbable resilient foams well known in the art. The core can also comprise a fluid-expandable membrane, e.g., a balloon. The compressible core allows the lateral extensions 20 and 22 to be compressed for insertion into aperture 44, then to expand conforming to the shape of the annulus' 42 inner wall and to the cavity created by pathologic extrusion or surgical removal of the disc fragment.

In an illustrative method of use, as shown in FIGS. 11A-D, the lateral extensions 20 and 22 are compressed together for insertion into the aperture 44 of the disc annulus 42. The annulus stent 10 is then inserted into the aperture 44, where the lateral extensions 20, 22 expand. In an expanded configuration, the upper surface 28 can substantially conform to the contour of the inside surface of the disc annulus 42. The upper section 14 is positioned within the aperture 44 so that the annulus stent 10 may be secured to the disc annulus 42, using means well known in the art.

In an alternative method, where the length of the aperture 44 is less than the length of the outside edge 26 of the annulus stent 10, the annulus stent 10 can be inserted laterally into the aperture 44. The lateral extensions 20 and 22 are compressed, and the annulus stent 10 can then be laterally inserted into the aperture 44. The annulus stent 10 can then be rotated inside the disc annulus 42, such that the upper section 14 can be held back through the aperture 44. The lateral extensions 20 and 22 are then allowed to expand, with the upper surface 28 contouring to the inside surface of the disc annulus 42. The upper section 14 can be positioned within, or proximate to, the aperture 44 in the subannular space such that the annulus stent 10 may be secured to the disc annulus, using means well known in the art.

Figure 9:
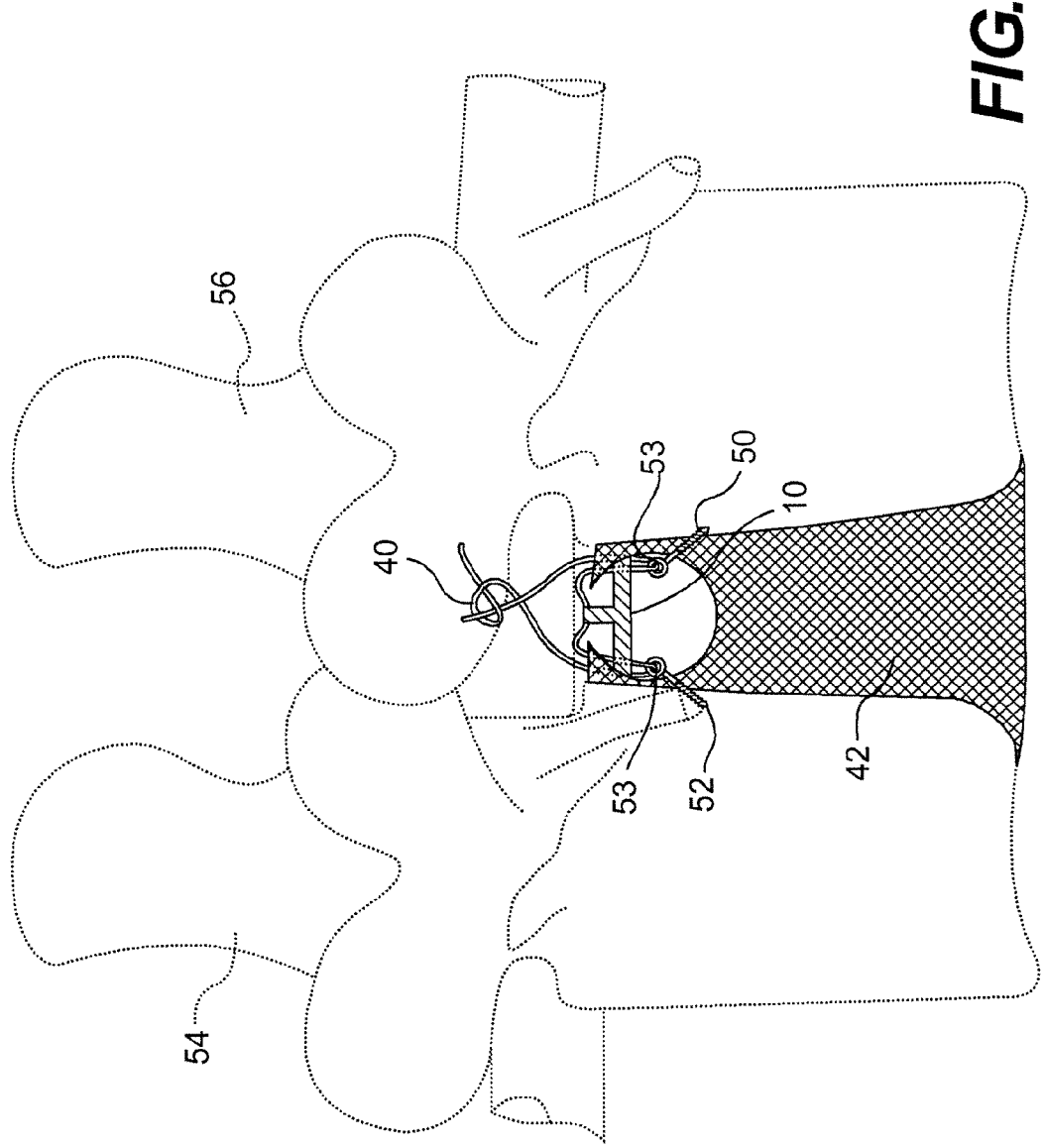
FIG. 9 shows a method of suturing an annulus stent into the disc annulus utilizing fixation points on vertebral bodies.

In an alternative method of securing the annulus stent 10 in the aperture 44, as shown in FIG. 9, a first surgical screw 50 and second surgical screw 52, with eyeholes 53 located at the top of the screws 50 and 52, are inserted into the vertebral bodies, illustratively depicted as adjacent vertebrae 54 and 56. After insertion of the annulus stent 10 into the aperture 44, a suture 40 is passed down though the disc annulus 42, adjacent to the aperture 44, through the eye hole 53 on the first screw 50 then back up through the disc annulus 42 and through the orifice 18 on the annulus stent 10. This is repeated for the second screw 52, after which the suture 40 is secured. One or more surgical sutures 40 are placed at about equal distances along the sides of the aperture 44 in the disc annulus 42. Reapproximation or closure of the aperture 44 is accomplished by tying the sutures 40 in such a fashion that the sides of the aperture 44 are drawn together. The reapproximation or closure of the aperture 44 enhances the natural healing and subsequent reconstruction by the natural tissue crossing the now surgically narrowed gap in the annulus 42. Preferably, the surgical sutures 40 are biodegradable but permanent non-biodegradable forms may be utilized. This method should decrease the strain on the disc annulus 42 adjacent to the aperture 44, precluding the tearing of the sutures through the disc annulus 42.

It is anticipated that fibroblasts will engage the fibers of the polymer or fabric of the intervertebral disc stent 10, forming a strong wall duplicating the currently existing condition of healing seen in the normal reparative process.

Figure 10A:
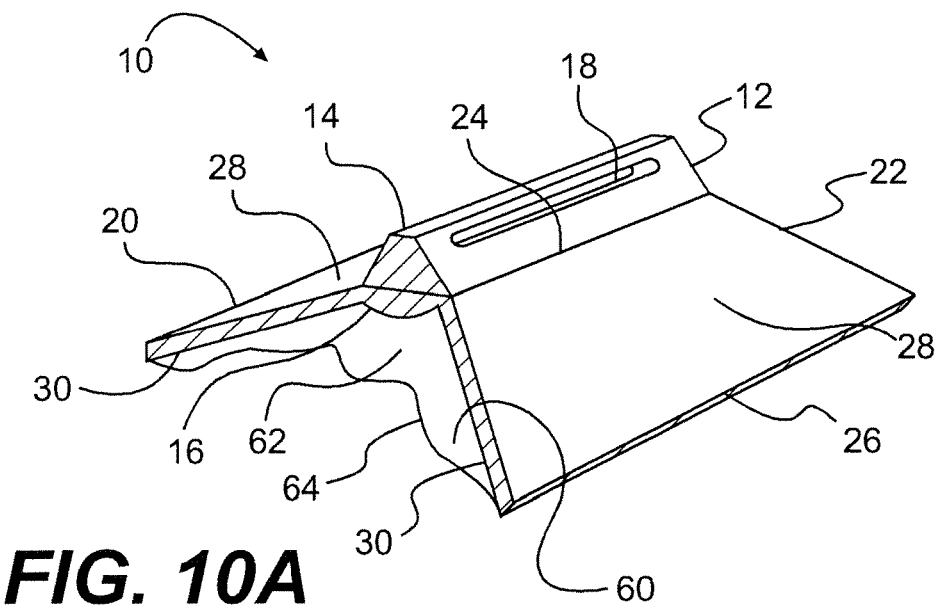
FIGS. 10A-10B show a further illustrative embodiment of an annulus stent with flexible bladder being expanded into the disc annulus.
Figure 10B:
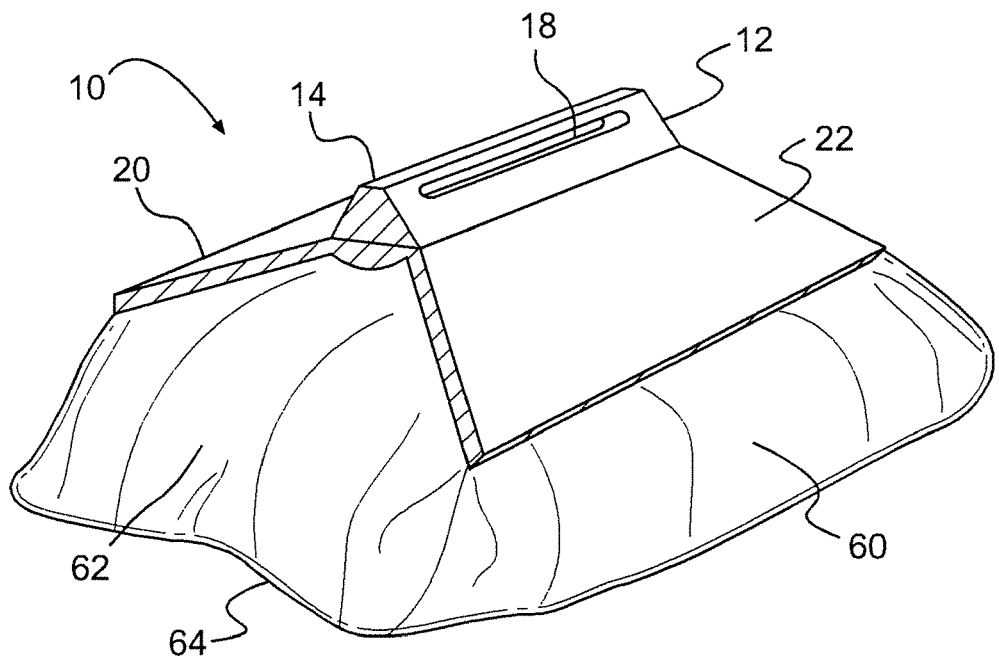

In an additional embodiment, as shown in FIGS. 10A-B, a flexible bladder 60 is attached to the lower surface 30 of the annulus stent 10. The flexible bladder 60 comprises an internal cavity 62 surrounded by a membrane 64, where the membrane 64 is made from a thin flexible biocompatible material. The flexible bladder 60 is attached to the lower surface 30 of the annulus stent 10 in an unexpanded condition. The flexible bladder 60 is expanded by injecting a biocompatible fluid or expansive foam, as known in the art, into the internal cavity 62. The exact size of the flexible bladder 60 can be varied for different individuals. The typical size of an adult nucleus is about 2 cm in the semi-minor axis, 4 cm in the semi-major axis, and 1.2 cm in thickness.

In an alternative embodiment, the membrane 64 is made of a semi-permeable biocompatible material. The mechanical properties of the injectate material may influence the performance of the repair and it is contemplated that materials which are "softer" or more compliant as well as materials that are less soft and less compliant than healthy nucleus are contemplated within the scope of certain embodiments of the invention. It must be understood that in certain embodiments the volume added to the subannular space may be less than equal to or larger than the nucleus volume removed. The volume of the implant may vary over time as well in certain embodiments.

In an illustrative embodiment, a hydrogel is injected into the internal cavity 62 of the flexible bladder 60. A hydrogel is a substance formed when an organic polymer (natural or synthetic) is cross-linked via, covalent, ionic, or hydrogen bonds to create a three-dimensional open-lattice structure, which entraps water molecules to form a gel. The hydrogel may be used in either the hydrated or dehydrated form.

Figure 12A:
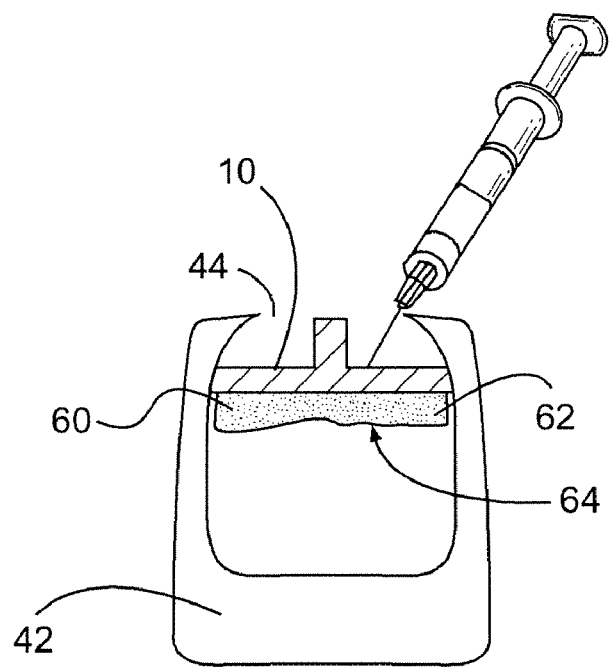
FIGS. 12A-12B show an annulus stent with a flexible bladder being expanded.
Figure 12B:
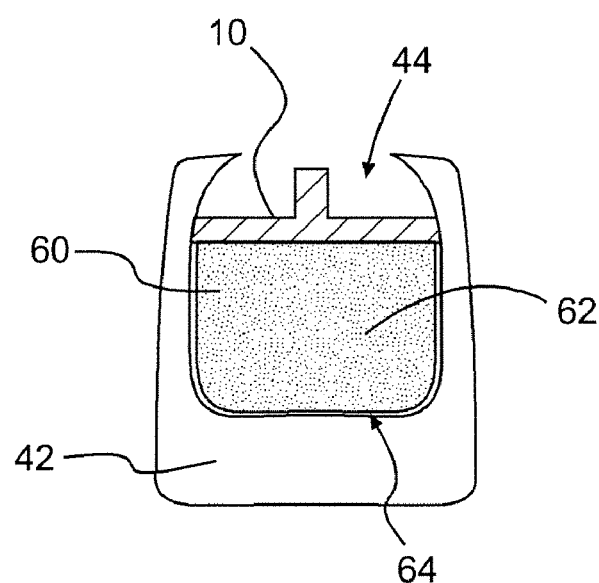

In a method of use, where the annulus stent 10 has been inserted into the aperture 44, as has been previously described and shown in FIGS. 12A-B, an injection instrument, as known in the art, such as a syringe, is used to inject the biocompatible fluid or expansive foam into the internal cavity 62 of the flexible bladder 60. The biocompatible fluid or expansive foam is injected through the annulus stent 10 into the internal cavity 62 of the flexible bladder 60. Sufficient material is injected into the internal cavity 62 to expand the flexible bladder 60 to fill the void in the intervertebral disc cavity. The use of the flexible bladder 60 is particularly useful when it is required to remove all or part of the intervertebral disc nucleus.

The surgical repair of an intervertebral disc may require the removal of the entire disc nucleus, being replaced with an implant, or the removal of a portion of the disc nucleus thereby leaving a void in the intervertebral disc cavity. The flexible bladder 60 allows for the removal of only the damaged section of the disc nucleus, with the expanded flexible bladder 60 filling the resultant void in the intervertebral disc cavity. A major advantage of the annulus stent 10 with the flexible bladder 60 is that the incision area in the annulus 42 can be reduced in size, as there is no need for the insertion of an implant into the intervertebral disc cavity.

In an alternative method of use, a dehydrated hydrogel is injected into the internal cavity 62 of the flexible bladder 60. Fluid, from the disc nucleus, passes through the semipermeable membrane 64 hydrating the dehydrated hydrogel. As the hydrogel absorbs the fluid the flexible bladder 60 expands, filling the void in the intervertebral disc cavity.

Figure 17A:
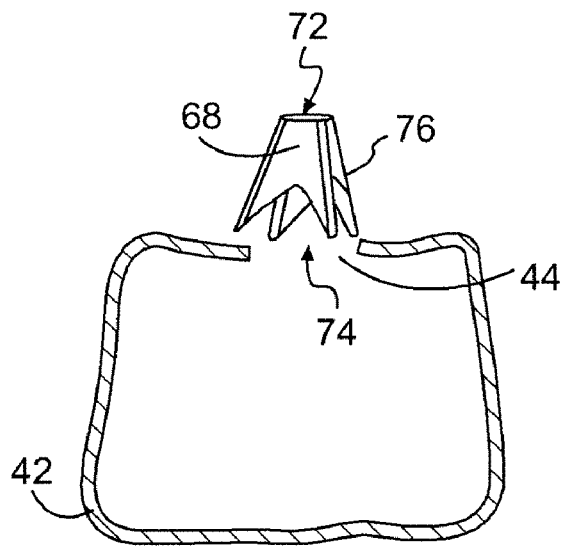
FIGS. 17A-17C show a method of inserting the annulus stent of FIG. 13 into the disc annulus.
Figure 17B:
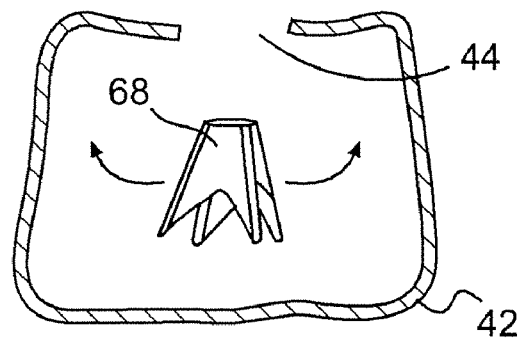
Figure 17C:
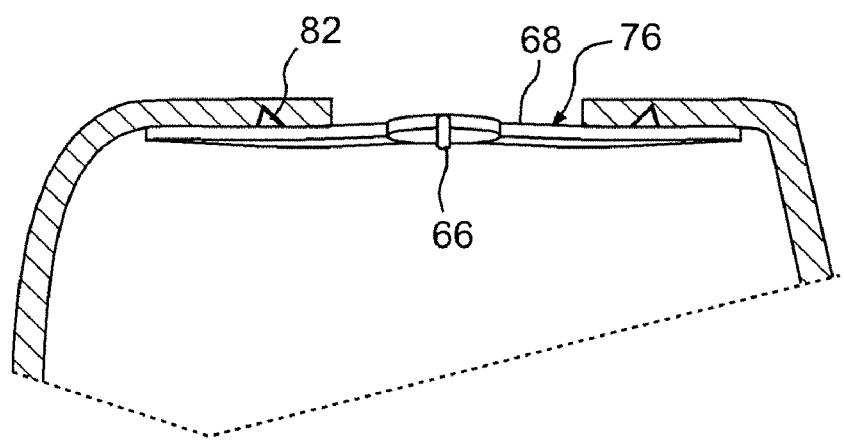

In an alternative embodiment, as shown in FIG. 13, the annulus stent 10 is substantially umbrella shaped, having a central hub 66 with radially extending struts 67. Each of the struts 67 is joined to the adjacent struts 67 by a webbing material 65, forming a radial extension 76 about the central hub 66. The radial extension 76 has an upper surface 68 and a lower surface 70, where the upper surface 68 contours to the shape of the disc annulus' 42 inner wall when inserted as shown in FIG. 17A-C, and where the lower surface 70 contours to the shape of the disc annulus' 42 inner wall when inserted as shown in FIG. 16A-C. The radial extension 76 may be substantially circular, elliptical, or rectangular in plan shape. Additionally, as shown in FIG. 20, the upper surface 68 of the radial extension 76 may be barbed 82 for fixation to the disc annulus' 42 inner wall and to resist expulsion through the aperture 42.

As shown in FIGS. 14 and 15, the struts 67 are formed from flexible material, allowing the radial extension 76 to be collapsed for insertion into aperture 44, then the expand conforming to the shape of the inner wall of disc annulus 42. In the collapsed position, the annulus stent 10 is substantially frustoconical or shuttlecock shaped, and having a first end 72, comprising the central hub 66, and a second end 74.

In an alternative embodiment, the radial extension 76 has a greater thickness at the central hub 66 edge than at the outside edge.

In an embodiment, the annulus stent 10 is a solid unit, formed from one or more of the flexible resilient biocompatible or bioresorbable materials well known in the art.

Additionally, the annulus stent 10 may comprise materials to facilitate regeneration of disc tissue, such as bioactive silica based materials that assist in regeneration of disc tissue as disclosed in U.S. Pat. No. 5,849,331 (Ducheyne, et al.), or other tissue growth factors well known in the art.

Alternatively, as shown in FIG. 21, a compressible core 84 may be attached to the lower surface 70 of the radial extension 76. The compressible core 84 may be made from one of the biocompatible or bioresorbable resilient foams well known in the art. The compressible core 84 allows the radial extension 76 to be compressed for insertion into aperture 44 then to expand conforming to the shape of the disc annulus' 42 inner wall and to the cavity created by pathologic extrusion or surgical removal of the disc fragment.

Figure 18B:
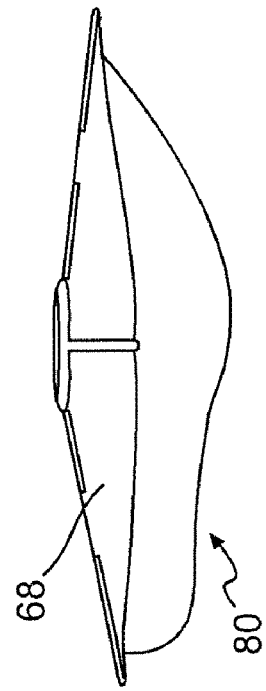
FIGS. 18A-18B show a further illustrative embodiment of an annulus stent with a flexible bladder.
Figure 19B:
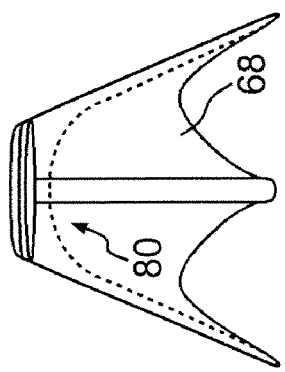
FIGS. 19A-19B show another illustrative embodiment of an annulus stent with a flexible bladder.
Figure 18A:
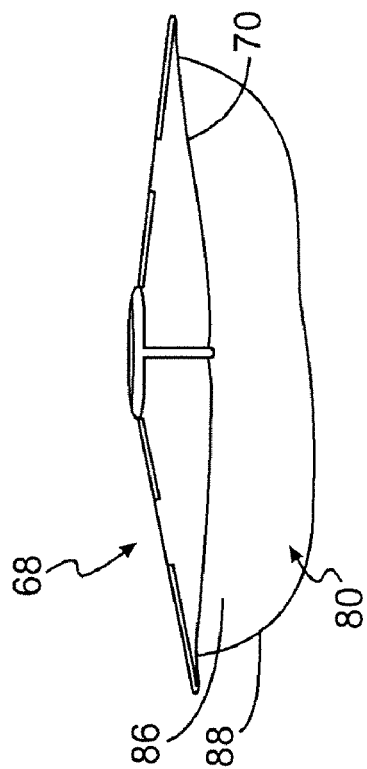
Figure 19A:
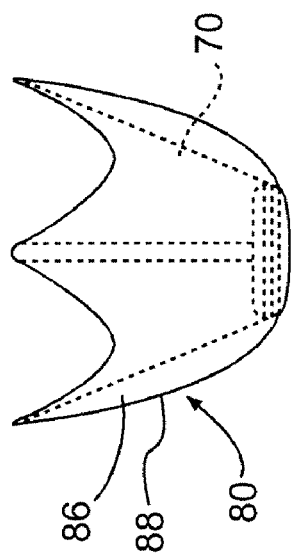

In an additional embodiment, as shown in FIGS. 18A and 18B, a flexible bladder 80 is attached to the lower surface 70 of the annulus stent 10. The flexible bladder 80 comprises an internal cavity 86 surrounded by a membrane 88, where the membrane 88 is made from a thin flexible biocompatible material. The flexible bladder 86 is attached to the lower surface 70 of the annulus stent 10 in an unexpanded condition.

The flexible bladder 80 is expanded by injecting a biocompatible fluid or expansive foam, as known in the art, into the internal cavity 86. The exact size of the flexible bladder 80 can be varied for different individuals. The typical size of an adult nucleus is 2 cm in the semi-minor axis, 4 cm in the semi-major axis and 1.2 cm in thickness.

In an alternative embodiment, the membrane 88 is made of a semi-permeable biocompatible material.

In a method of use, as shown in FIGS. 16A-16C, the radial extension 76 is collapsed together, for insertion into the aperture 44 of the disc annulus 42. The radial extension 76 is folded such the upper surface 68 forms the outer surface of the cylinder. The annulus stent 10 is then inserted into the aperture 44, inserting the leading end 72 though the aperture 44 until the entire annulus stent 10 is within the disc annulus 42. The radial extension 76 is released, expanding within the disc 44. The lower surface 70 of the annulus stent 10 contours to the inner wall of disc annulus 42. The central hub 66 is positioned within the aperture 44 so that the annulus stent 10 may be secured to the disc annulus 42 using means well known in the art.

It is anticipated that fibroblasts will engage the fibers of the polymer of fabric of the annulus stent 10, forming a strong wall duplicating the currently existing condition of healing seen in the normal reparative process.

In an alternative method of use, as shown in FIGS. 17A-17C, the radial extension 76 is collapsed together for insertion into the aperture 44 of the disc annulus 42. The radial extension 76 is folded such that the upper surface 68 forms the outer surface of the stent, for example in a frustoconical configuration as illustrated. The annulus stent 10 is then inserted into the aperture 44, inserting the tail end 74 through the aperture 44 until the entire annulus stent 10 is in the disc. The radial extension 76 is released, expanding within the disc. The upper surface 68 of the annulus stent 10 contours to the disc annulus' 42 inner wall. The central hub 66 is positioned within the aperture 44 so that the annulus stent 10 may be secured to the disc annulus 42, using means well known in the art.

In one illustrative embodiment, the barbs 82 on the upper surface 68 of one or more strut 67 or other feature of the radial extension 76, engage the disc annulus' 42 inner wall, holding the annulus stent 10 in position.

In a method of use, as shown in FIGS. 12A-12B, where the annulus stent 10 has been inserted into the aperture 44, as has been previously described. Similarly, for the stent shown in FIGS. 18 through 21, an injection instrument, as known in the art, such as a syringe, can be used to inject the biocompatible fluid or expansive foam into the internal cavity 86 of the flexible bladder 80. The biocompatible fluid or expansive foam is injected through the annulus stent 10 into the internal cavity 86 of the flexible bladder 80. Sufficient material is injected into the internal cavity 86 to expand the flexible bladder 80 to fill the void in the intervertebral disc cavity. The material can be curable (i.e., glue). The use of the flexible bladder 80 is particularly useful when it is required to remove all or part of the intervertebral disc nucleus.

It should be noted that in any of the "bag" embodiments described herein one wall or barrier can be made stiffer and less resilient than others. This relatively stiff wall member can then be placed proximate the annulus wall and can advantageously promote, in addition to its reparative properties, bag containment within the annulus.

Figure 22:
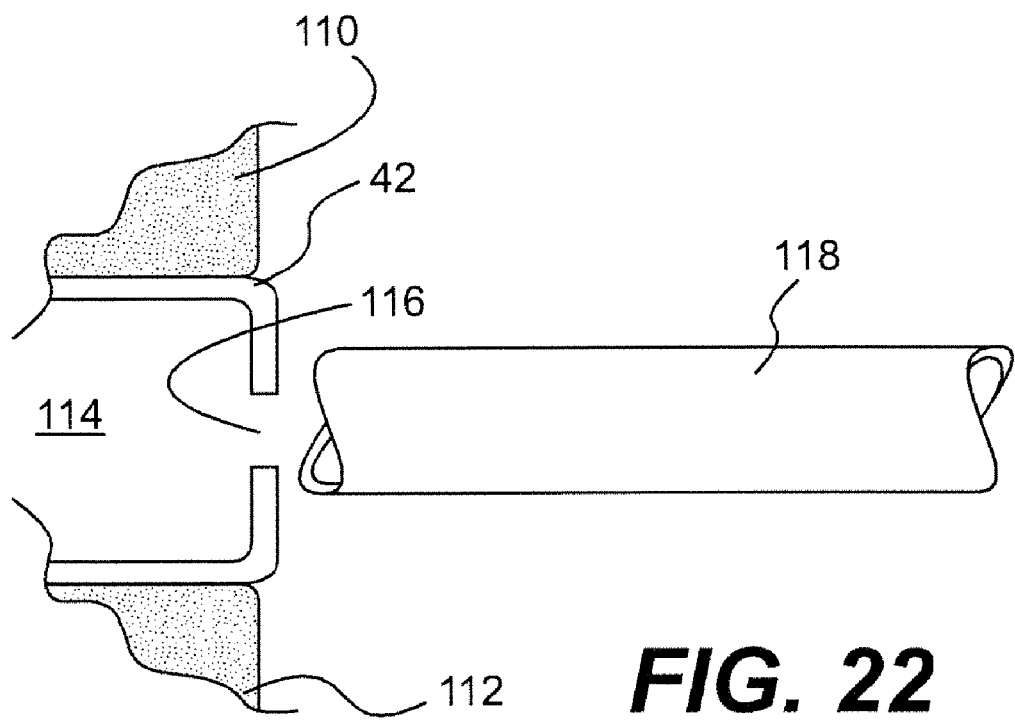
FIG. 22 shows a still further illustrative embodiment of an introduction device for an annulus stent.

FIG. 22 shows a further aspect of the present invention. According to a further illustrative embodiment, a simplified schematic cross section of a vertebral pair is depicted including an upper vertebral body 110, a lower vertebral body 112 and an intervertebral disc 114. An aperture or rent 116 in the annulus fibrosus (AF) is approached by a tube 118, which is used to deliver a device 120 according to a further aspect of the present invention. The device 120 may be captured by a delivery tool 122 through the use of a ring or other fixation feature 124 mounted on the repair device 120.

Figure 23:
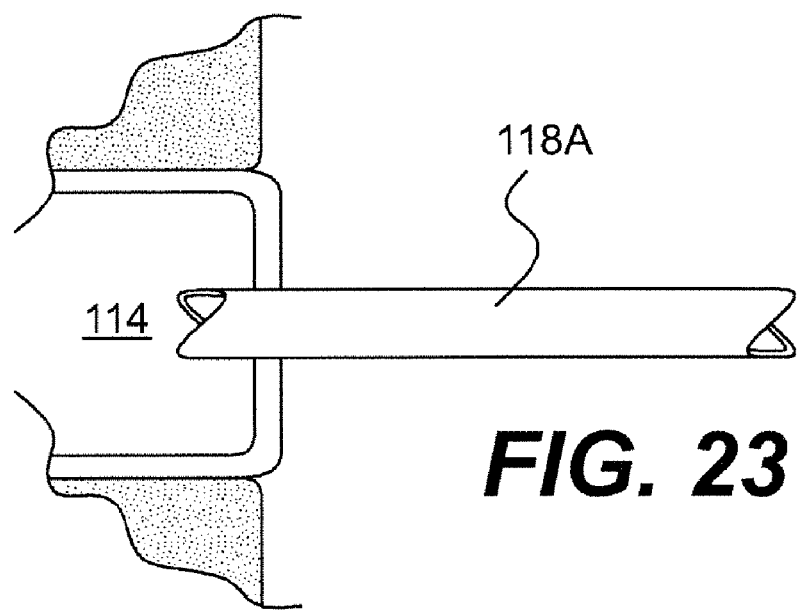
FIG. 23 shows a modification of the device depicted in FIG. 22.

FIG. 23 shows a delivery method similar to that depicted in FIG. 22, with the exception that the tube 118A has a reduced diameter so that it may enter into the sub-annular space of the disc 114 through the aperture or rent.

Figure 24:
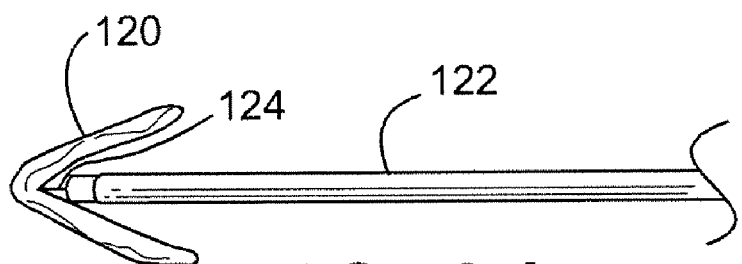
FIG. 24 shows an exemplary introduction tool for use with the devices of FIGS. 22 and 23 with a stent deflected proximally.
Figure 25:
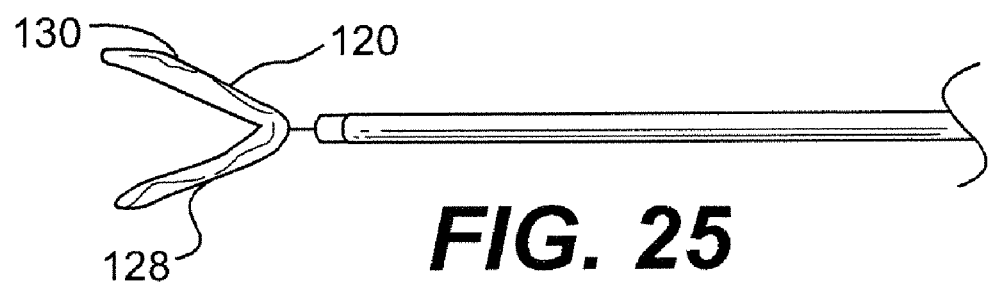
FIG. 25 shows an exemplary introduction tool for use with the devices of FIGS. 22 and 23 with a stent deflected distally.
Figure 26:
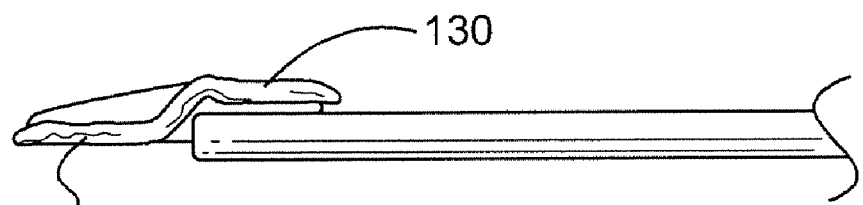
FIG. 26 shows an exemplary introduction tool for use with the devices of FIGS. 22 and 23 with a stent deflected partially distally and partially proximally.

Turning to FIG. 25, according to a further aspect of the present invention, the delivery of the device 120 through the delivery tube 118 or 118A may be facilitated by folding the arms or lateral extensions 128, 130 of the device to fit within the lumen of the tube 118 or 118A so that the stent or device 120 is introduced in a collapsed configuration. The device 120 is moved through the lumen of the tubes 118 or 118A through the use of delivery tool 122. FIG. 25 shows the arms deflected in a distal, or forward direction for insertion into the delivery tube 118 or 118A while FIG. 24 shows the arms 128, 130 deflected into a proximal position. FIG. 26 shows the device 120 curled so that one arm 128 is projecting distally, or in a forward direction, and the other arm 130 is projecting proximally, or in a rearward direction. Because the lateral extent of the device is relatively flexible, whether the device is of natural or synthetic material, other collapsible configurations consistent with the intent of this invention are also possible, including twisting, balling, crushing, etc.

Figure 27:
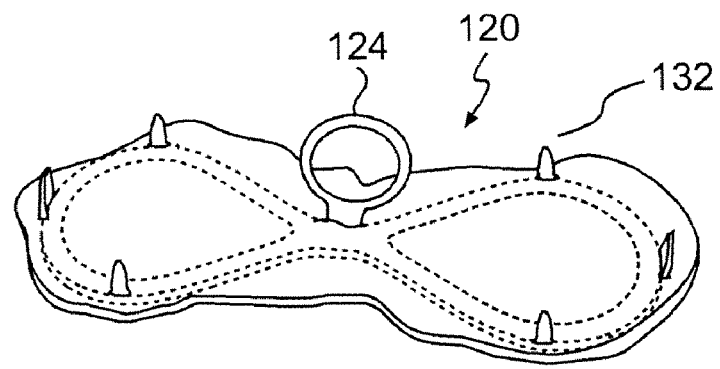
FIG. 27 shows a still further illustrative embodiment of a stent device having a grasping feature and fixation devices in the form of barbs.

FIG. 27 shows the device 120 having a series of peripheral barb structures typified by barb 132 located at the edges. In operation, these barbs may be forced into the annulus fibrosus as seen in connection with FIG. 28. Barb placement can be anywhere on the device 120 provided that at least some number of barbs are likely to find annulus fibrosus tissue to anchor in during placement. For a simple aperture or rent, placement on the periphery of the device body is a reasonable choice, but for complex tears, it may be desirable to place a plurality of barbs on the device not knowing in advance which barbs will find tissue to anchor in during placement.

Figure 29:
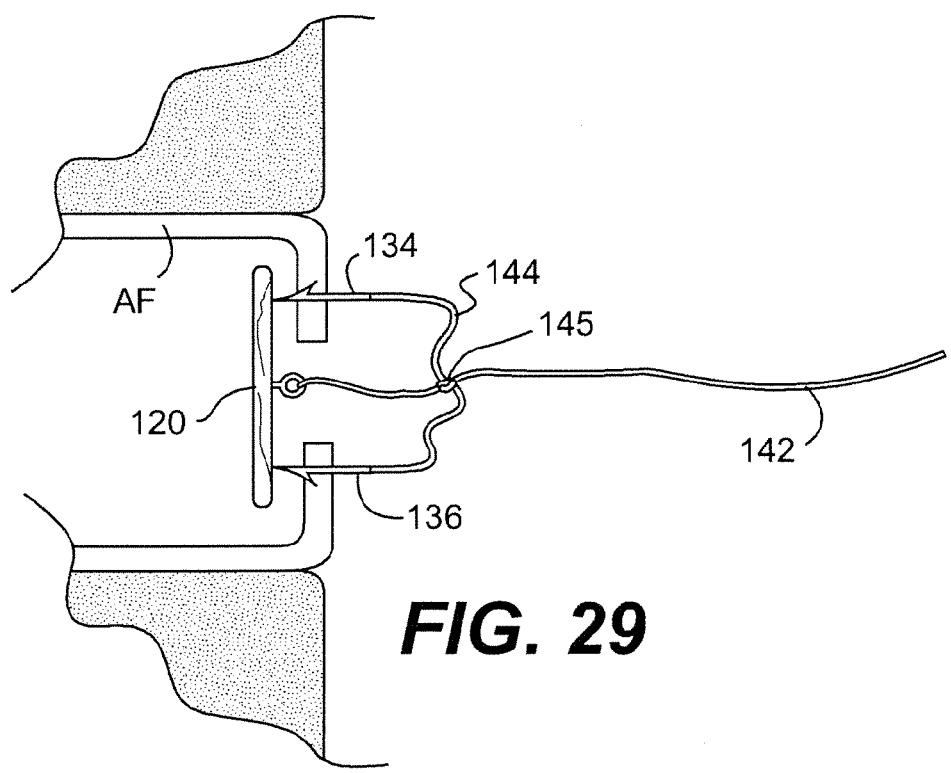
FIG. 29 shows a still further illustrative embodiment of an annulus stent employing a secondary barbed fixation device.

FIG. 29 shows an alternative fixation strategy where a pair of barbs 134 and 136 are plunged into the annulus fibrosus from the exterior of the annulus while the device 120 is retained in the sub-annular space by means of a tether 142. Although there are a wide variety of fixation devices in this particular example, a tether 142 may be knotted 145 with the band 144 holding the barbs 134 and 136 together to fix the device in the sub-annular space. The knot is shown in an uncinched position to clarify the relationship between the tether 142 and the bands 144. Using this approach, the device can be maintained in a subannular position by the barbed bands while the tether knot is cinched, advantageously simultaneously reapproximating the annulus to close the aperture while drawing the device into sealing, bridging engagement with the subannular wall of the annulus fibrosus.

Figure 30:
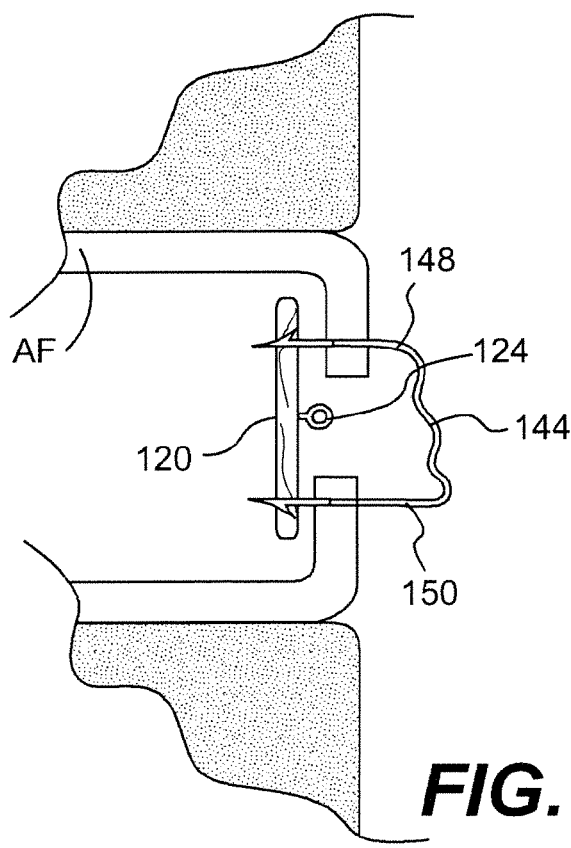
FIG. 30 shows a still further illustrative embodiment of an annulus stent employing another example of a secondary barbed fixation device.

FIG. 30 shows an alternative fixation strategy where the barbs 148 and 150 are sufficiently long that they can pierce the body of the device 120 and extend all the way through the annulus fibrosus into the device 120. In this configuration, the band 144 connecting the barbs 148 and 150 may be tightened to gently restrain and position the device 120 in the sub-annular space, or tightened with greater force to reapproximate the aperture or rent.

Figure 31:
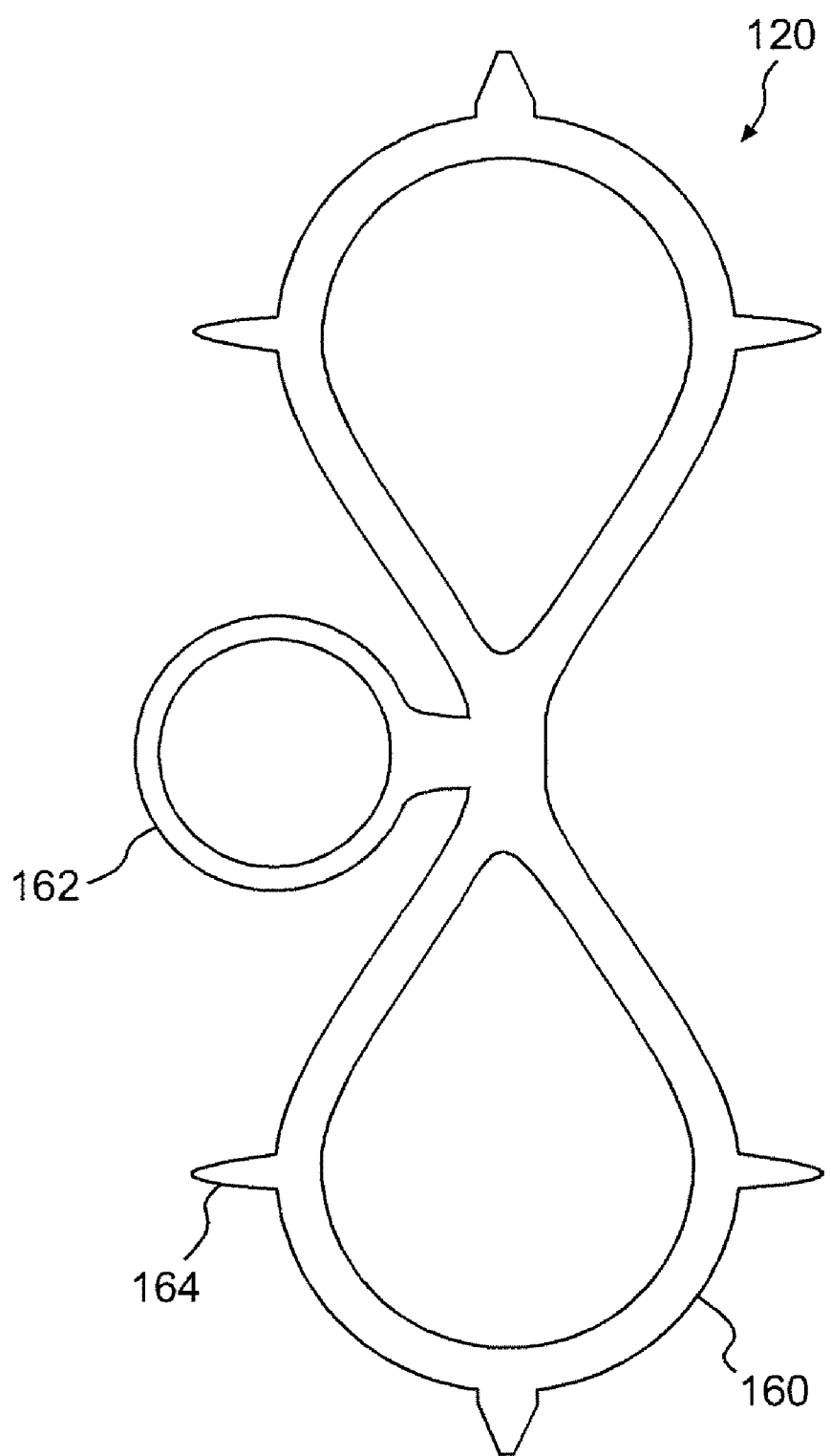
FIG. 31 shows the frame of a still further illustrative embodiment of an annulus stent having a metal substrate being machined from flat stock.
Figure 32A:
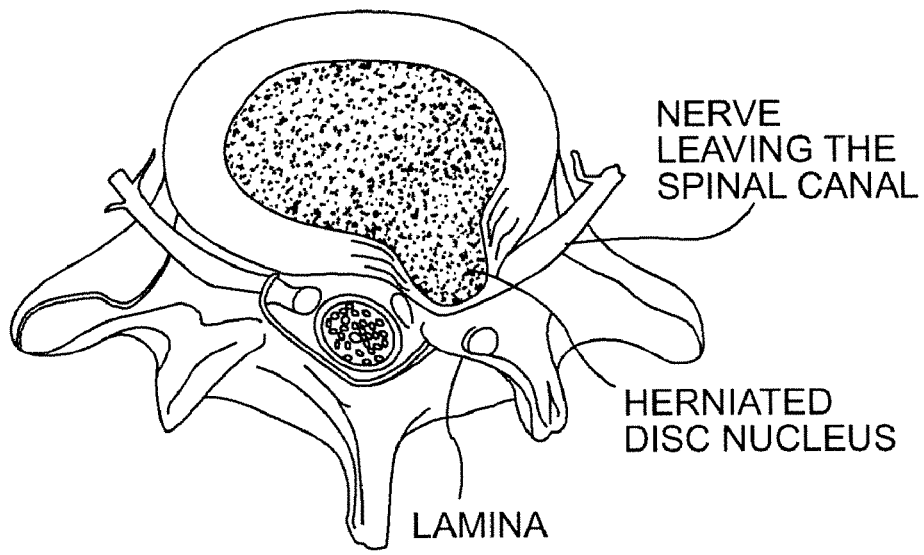
FIG. 32A shows a herniated disc in perspective view.
Figure 32B:
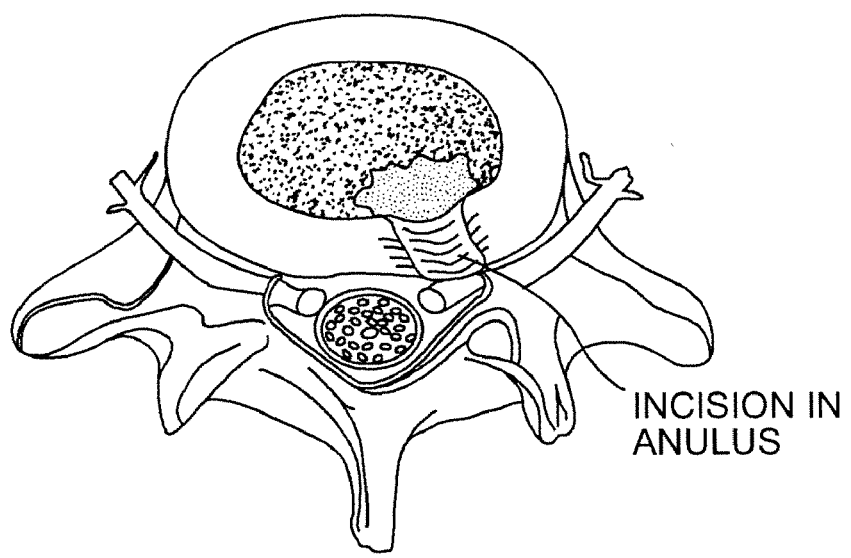
FIG. 32B shows the same disc after discectomy.
Figure 33B:
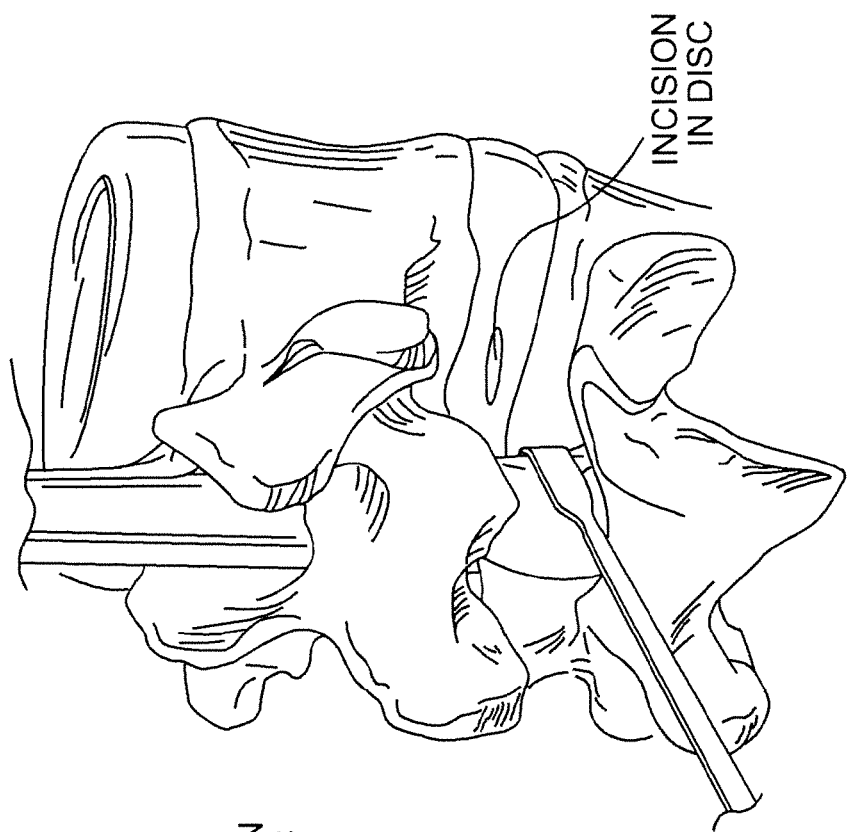
FIG. 33B shows a posteriolateral view of the disk showing an incision.
Figure 33A:
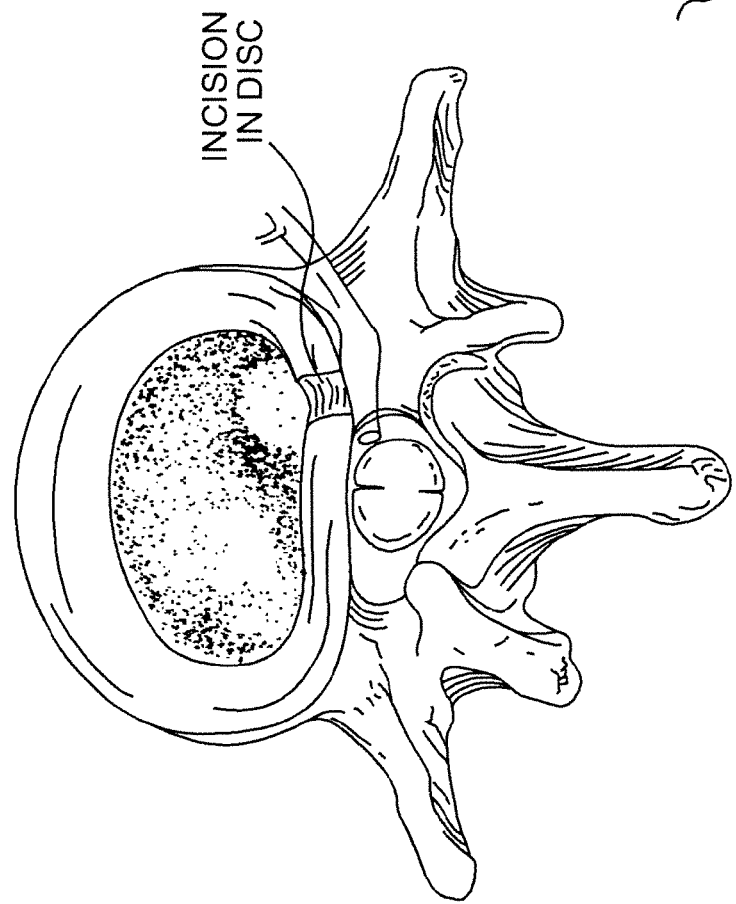
FIG. 33A shows a top view of the disc post-discectomy.

FIG. 31 shows a still further illustrative embodiment according to another aspect of the present invention. In this embodiment, a metal substrate 160 is incorporated into the device 120. This piece can be machined from flat stock and includes the loop 162 as well as barbs typified by barb 164.

Figure 28:
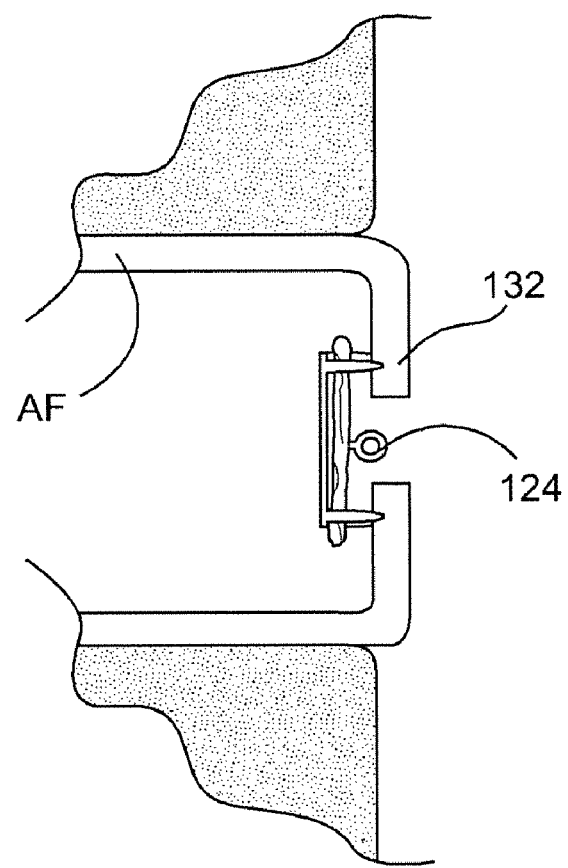
FIG. 28 shows the illustrative embodiment in FIG. 27 deployed subannularly.

When formed in to the device 120 the structure shown in FIG. 31 is used in a manner analogous to FIG. 27 and FIG. 28.

Figure 5B:
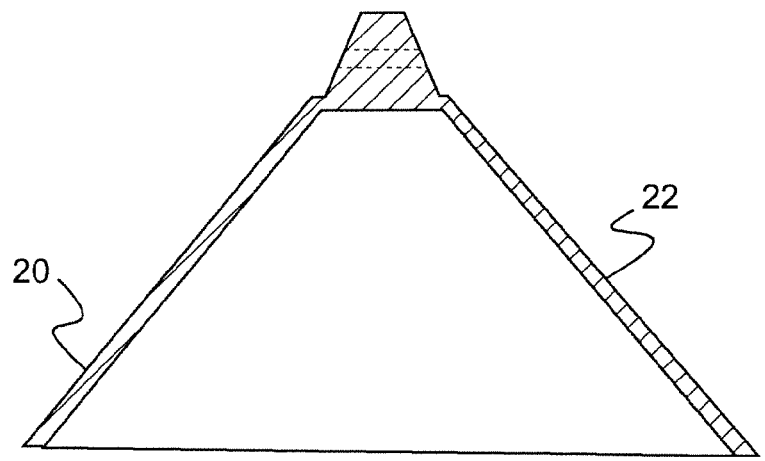
Figure 6A:
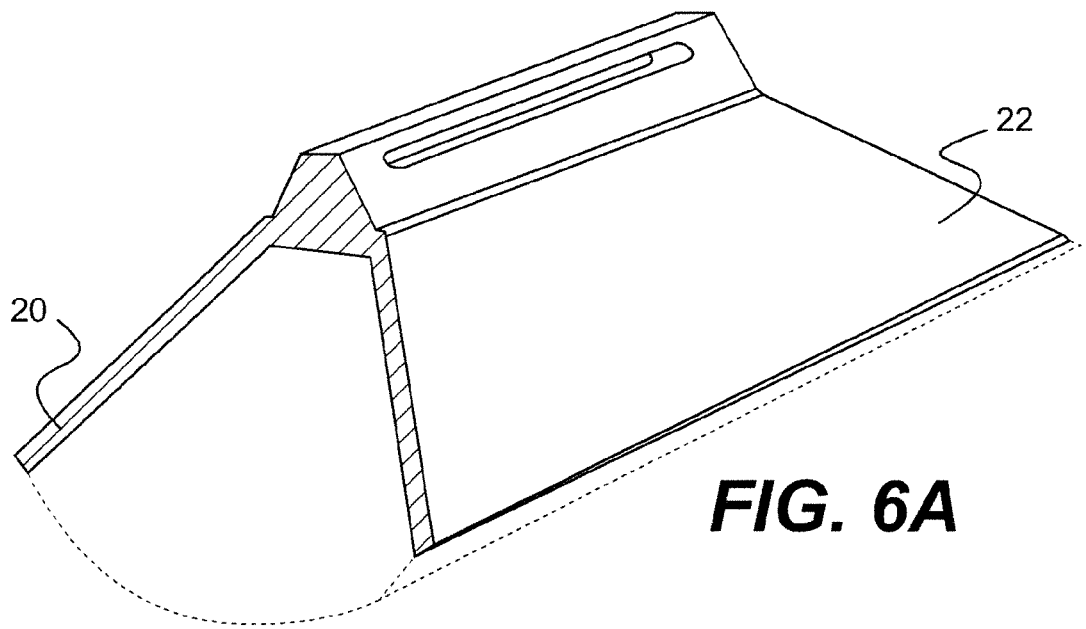
FIGS. 6A-6B show the alternative embodiment of a further illustrative embodiment of an annulus stent.
Figure 6B:
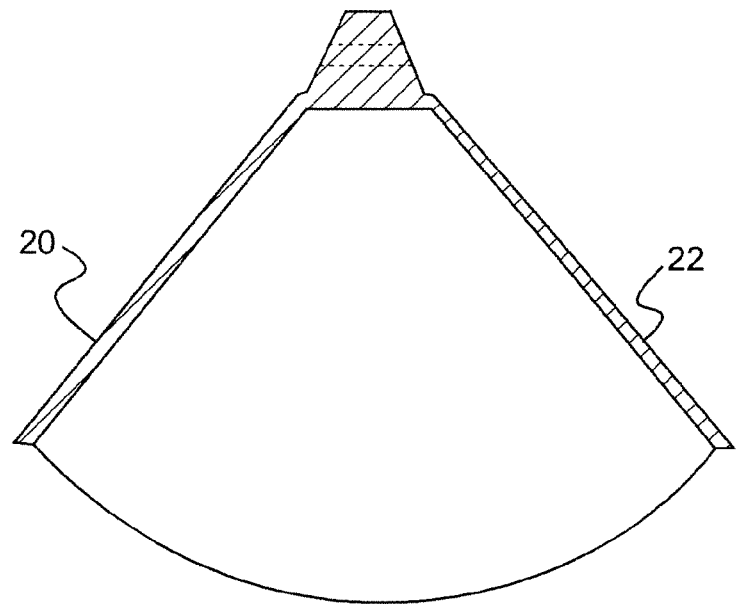
Figure 34:
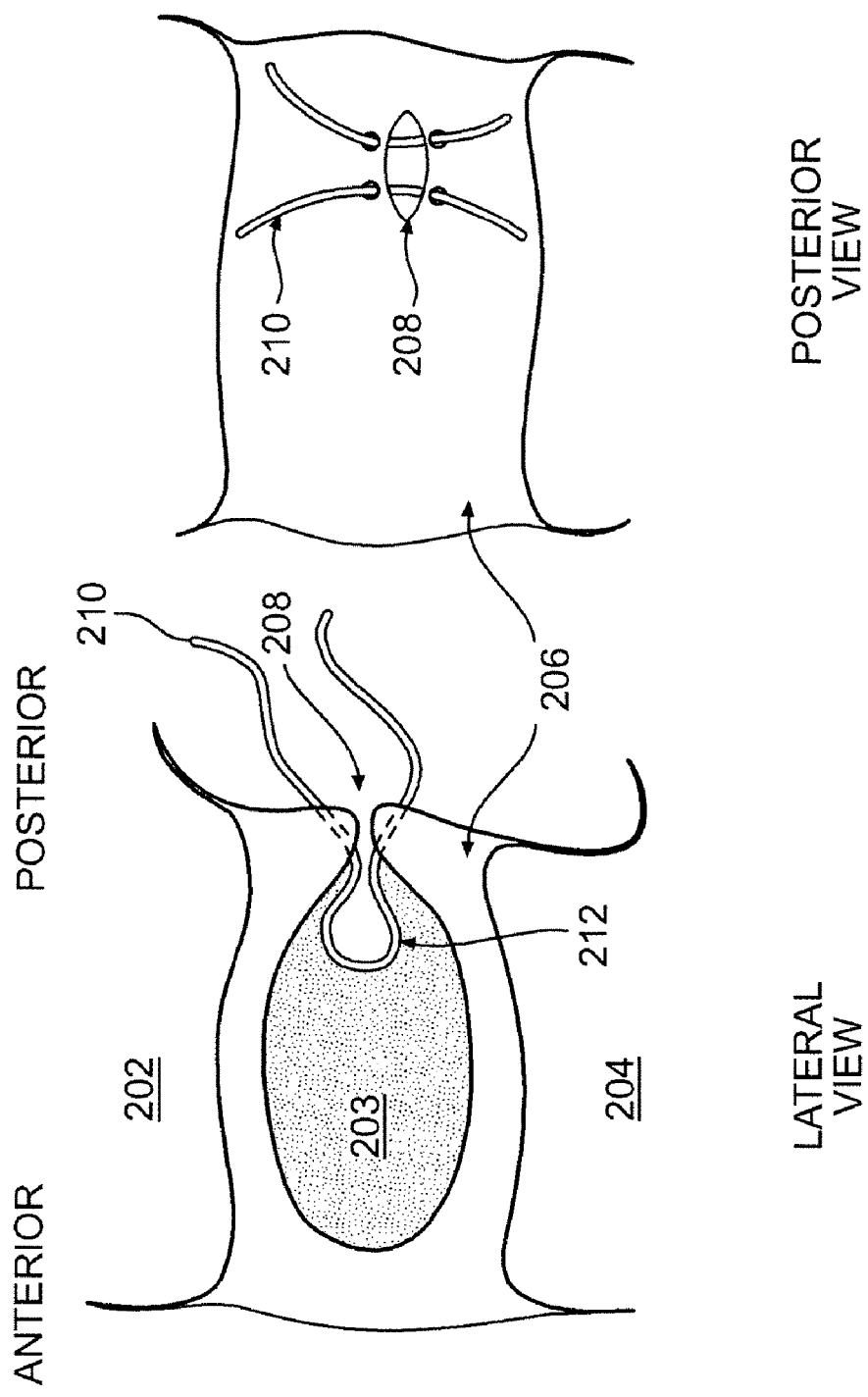
FIG. 34 shows schematically the creation of a subannular sling using sutures.
Figure 35:
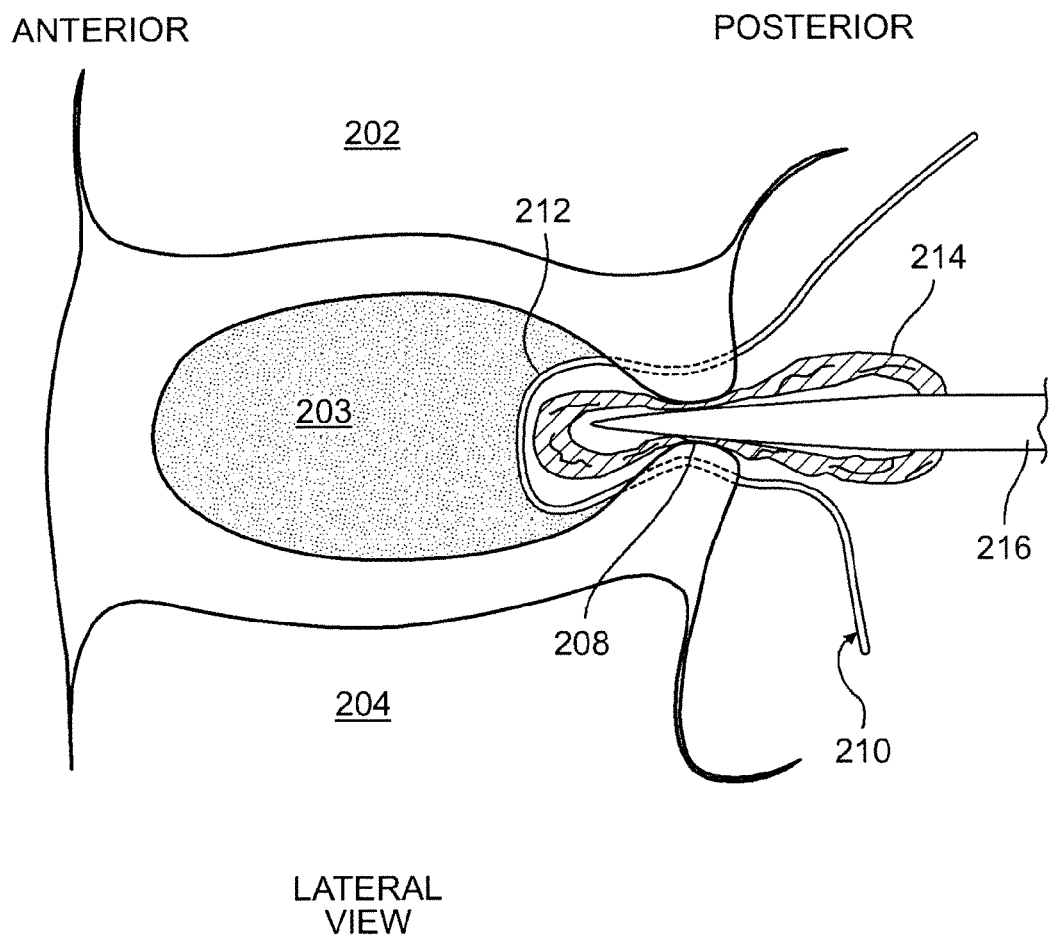
FIG. 35 schematically shows the introduction of a compressed autograft stent/patch into the subannular space.
Figure 36:
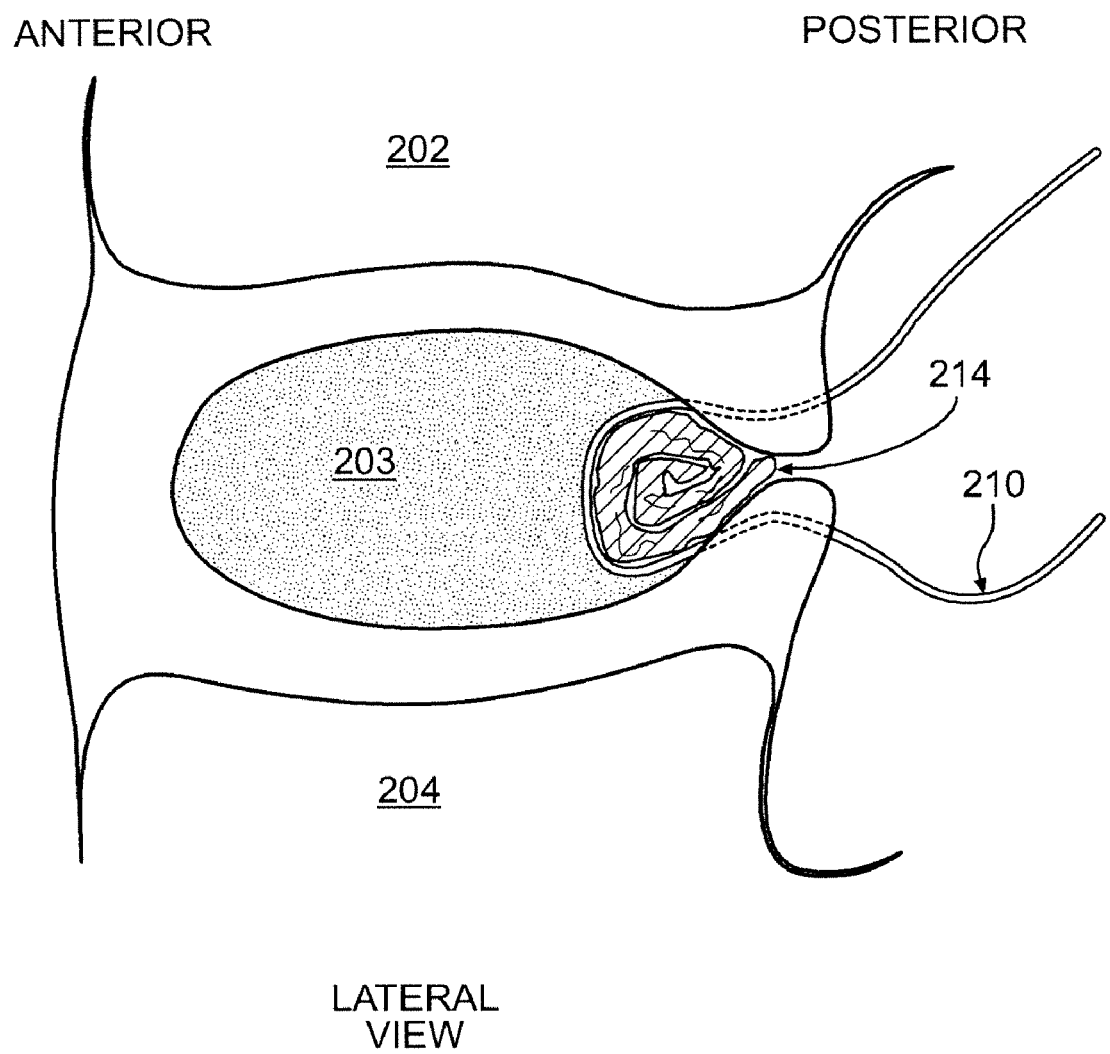
FIG. 36 schematically shows the autograft of FIG. 35 in an expanded shape within the annulus.
Figure 37:
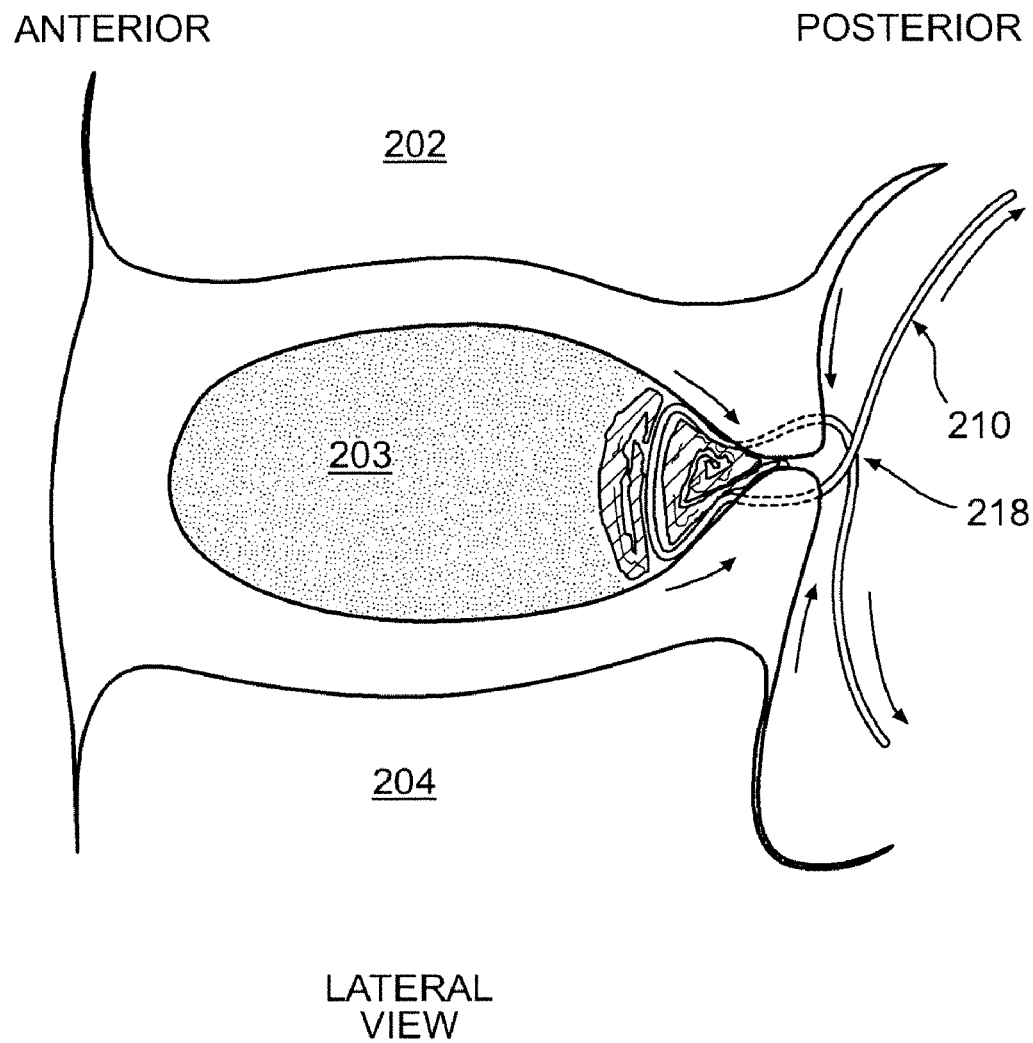
FIG. 37 schematically shows the tightening of the sutures to reapproximate the annulus aperture and draw the stent/patch of FIG. 35 toward the annular wall.

Stents can expand to be planar, for example as shown hereinabove in FIGS. 4, 8, 9, 11 and 12, or they can expand to be three-dimensional as shown hereinabove in FIGS. 5 and 10. FIGS. 34-36 depict a further three dimensional patch/stent using an autograft formed of fascial tissue. FIG. 34 shows the superior vertebral body 202 and the inferior vertebral body 204 surrounding a disc having an annulus fibrosus 206 and nucleus pulposus 203 in the subannular space. According to this illustrative embodiment of the invention, a suture 210 is passed from outside the annulus through the wall of the annulus on one side of an aperture 208 and into the subannular space as shown. The suture is then passed back out through the annular wall on an opposing side of the aperture 208 leaving a loop or sling 212 of suture in the subannular space. As shown in the posterior view on the right side of FIG. 34, more than one suture can be applied. Turning to FIG. 35, a fascial autograft 214 is then inserted through the aperture 208 into the subannular space using, for example, forceps 216. FIG. 36 shows the fascial stent/patch 214 fully inserted into the subannular space within the suture sling 212. The closure of the aperture is accomplished simultaneously with pulling the autograft 214 toward the annular wall as shown in FIG. 37. The suture 210 can be cinched 218 or tied to maintain the closure and the fixation of the patch/stent.

Patches can be folded and expanded in a single plane or in three dimensions. As shown in FIGS. 24-25 and 41 for example, collapsing the patch can be accomplished laterally, whether the device is a single material or composite. Other embodiments, such as that shown in FIG. 1 can collapse vertically, and still others such as that shown in FIG. 26, longitudinally. Others can collapse in three dimensions, such as those shown in FIGS. 13-15 and 36. Devices which expand in three dimensions can be packaged in a restraining jacket, such as a gelatine shell or "gelcap" for example, or a mesh of biosorbable or dissolvable material, that would allow for facile placement and subsequent expansion.

Patches can also be constructed of a single component, as shown for example in FIG. 36, made of autograft or a synthetic material such as Dacron, or for example where the stent is a gelcap. They can be made of multiple components. An exemplary stent (not shown) can be made from a polymeric material, for example silicone rubber, which can be formed to have a natural unstressed shape, for example that of a "Bulb". A stylet or push-rod can, for example, be inserted on the inside of the bulb to stretch the bulb into a second shape which is thinner and elongated. The second shape is sufficient to place within the aperture in the annulus. Upon placement of the device within the sub-annular space, the push-rod is removed and the bulb assumes it natural, unstressed state, assuming a larger dimension within the sub-annular space. Although silicone is used in this example, other metallic constructs could also be envisioned such as a Nitinol braided device that has a natural unstressed shape and assumes a second shape under tension for the delivery of the device. It is also contemplated that the opposite scenario can also accomplish the similar objective. In this alternative embodiment, the device can have a first configuration that is unstressed and elongated and assumes a second, larger configuration (bulb) under stress. In this embodiment, a portion of the stylet or rod that is used to mechanically activate the device would be left behind to hold the expansion element in its stressed configuration.

Multiple components could include a frame to help with expansion of the device and a covering to obtain biocompatibility and tissue ingrowth. Examples of different frame configurations might include an expandable "Butterfly" or "Figure-8" configuration that could be constructed of wire material, such as Nitinol or multiple wires. Exemplary embodiments showing frame members 502 are depicted in FIG. 41A-E. Of course, other configurations such as diamonds or other rounded or polygonal shapes can be used. The diamond frame is a construct that takes a first form that is smaller and expands to a larger frame. The diamond elements could be constructed from a single wire or from multiple wires. Alternatively, the members could be constructed of elements that are moveable fixed at each of the ends to allow expansion. A tether or attachment device 504 is also depicted, which may be a suture, a wire, a screw, or other attachment means known in the art.

The frame could be cut from a single material, such as flat stock Nitinol to accomplish the same objective, as shown for example in FIG. 31. Such shapes can be cut from flat stock using known methods, for example, laser cutting. A heat forming step could also be employed, as known in the art, to form barbs 132 in a shape that passes out of the flat plane of the stock material, as shown in FIG. 27 for example.

Another frame configuration, also not shown, is that of a spiral or coil. The "Coil" design can be, for example, a spring steel or other biocompatible material that is wrapped to a first "wound" smaller configuration and expands to a larger unwrapped, unwound configuration.

Depending on the size of the openings in the frames described above, each of these concepts may or may not have a covering over them in order to assure that the nucleus does not re-extrude from the intervertebral disc space after placement of the device, as well as to serve as substrate for the surrounding tissue to naturally incorporate the device. Coverings might include ePTFE, polyester, silicone, or other biocompatible materials. Coverings could also include natural materials such as collagen, cellulose, autograft, xenograft, allograft or similar materials. The covering could also be biodegradable in nature, such as polyvinyl lactic acid.

Frames that are not covered may be permeable, such as a patch that is porous and allow for normal movement of fluids and nutrients through the patch into and out of the annular ring while maintaining nucleus fragments larger than the porosity of the stent/patch within the subannular space. Depending on the material that the frame is constructed, a surface finish may be added to promote tissue ingrowth into the patch. For example, a titanium sputtering of the device may allow it to be more easily incorporated within the disc space. Alternatively, a NiTi or tantalum foam could be added to the outer surface of the patch to promote tissue ingrowth.

It is understood that there can be a variety of device designs of patches to accomplish the expansion of a device from a first configuration, to a second configuration to occupy the subannular space and reduce re-extrusion of the nucleus. The following device concepts are further discussed for additional embodiments of a device and/or system for the repair of an intervertebral disc annulus.

As mentioned hereinabove, the stent/patch according to the present invention may comprise a mass of fascial autograft, and that autograft may be contained in a covering of material to form what will be referred to herein as a "bag". Of course, this term is used not necessarily to connote a five-sided closed container so much as to denote the notion of flexibly surrounding the volume of a patch/stent material so that it can be manipulated in space.

In the most simplistic form, a prefabricated device of sutures could be used to form the "sling" to hold the fascial implant as discussed above. The advantage of this design over simple placement of sutures to hold the autograft is better containment and control of the autograft during and after implantation. The "sling" or a "bag" surrounds the fascial autograft to hold it in place. It is contemplated that other materials, such as a polyester mesh, could be used instead of the fascial autograft.

Figure 38:
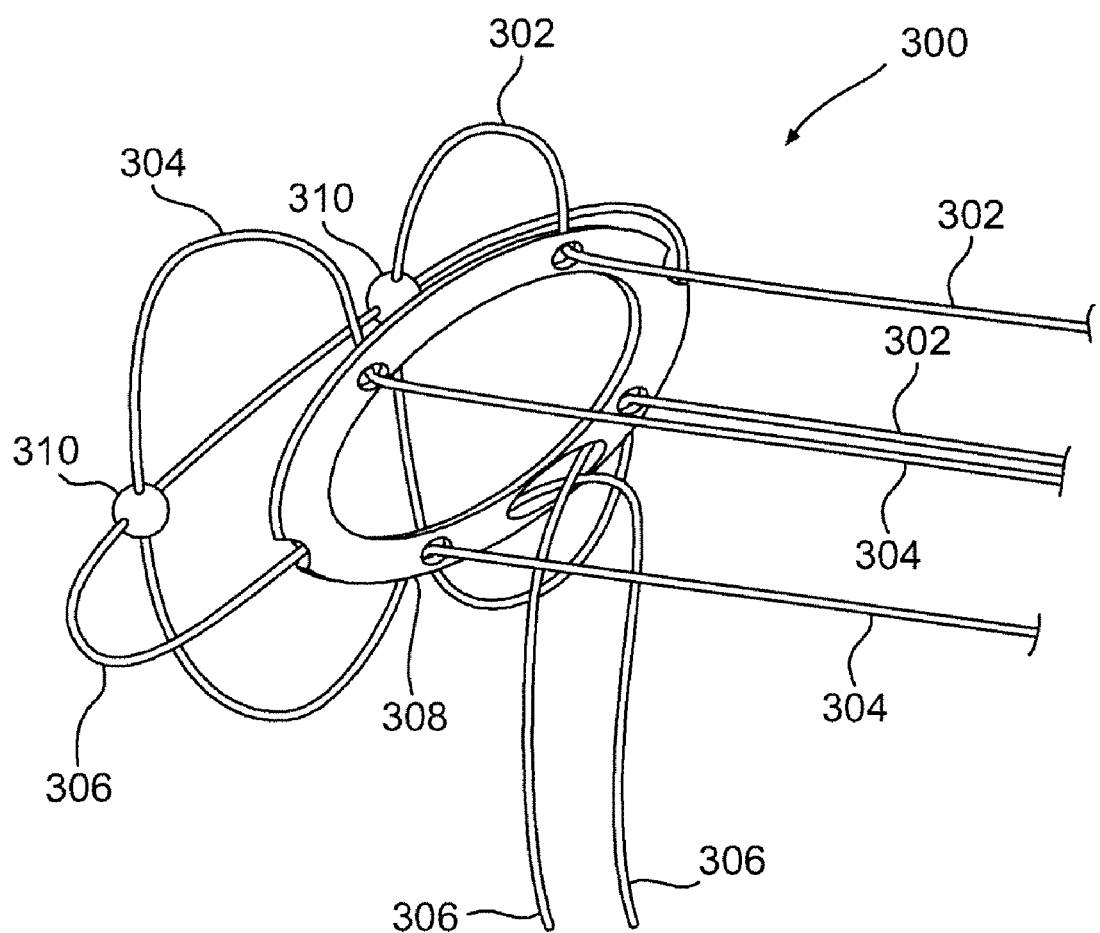
FIG. 38 shows an exemplary collar for use in repairing a disc annulus.
Figure 39:
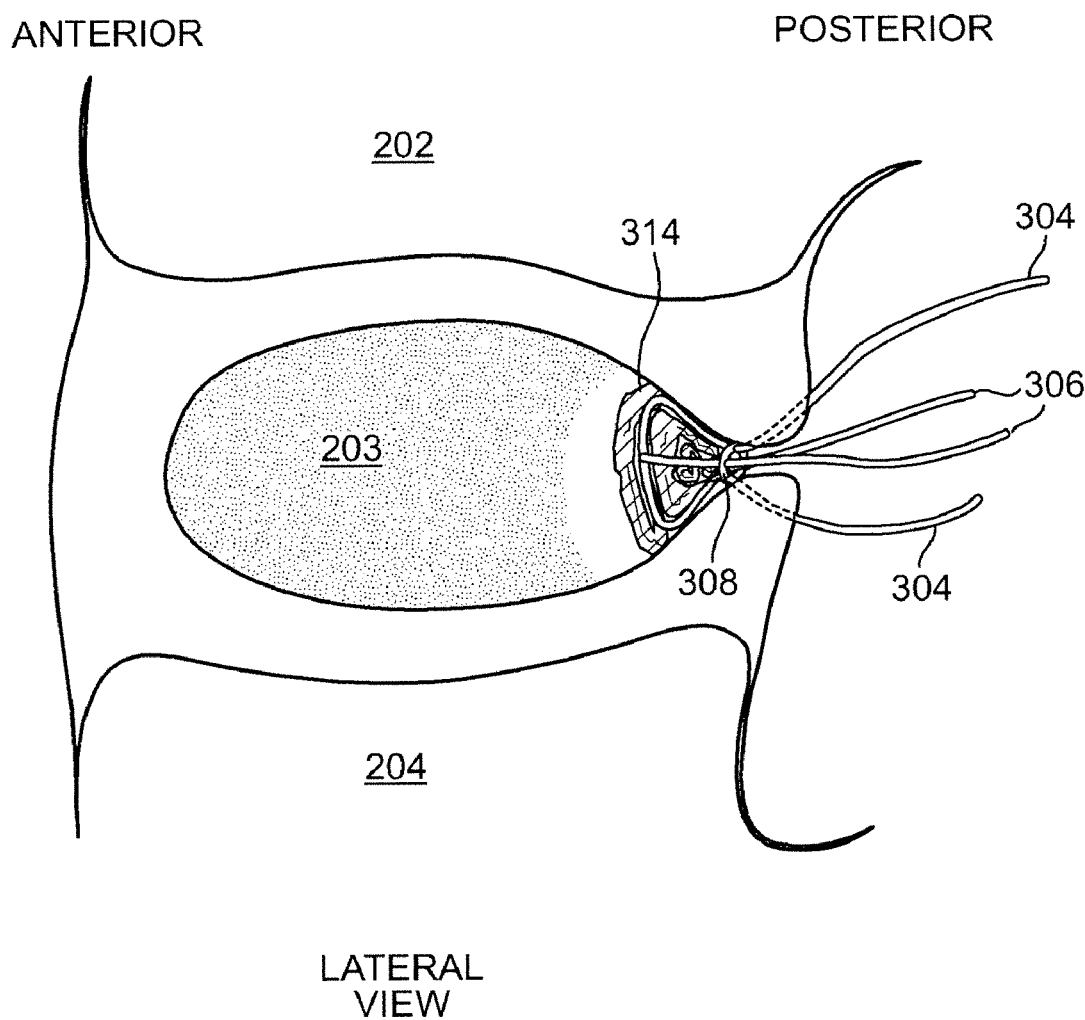
FIG. 39 schematically depicts the collar of FIG. 38 in use for disc annulus repair.

FIG. 38 shows an example of a pre-fabricated sling 300. There are three sutures used in this example, 302, 304, and 306, although there could be more or less sutures as would be understood by one of ordinary skill in the art. A collar member 308 has apertures or other features for attaching to the sutures. In this example, the third suture 306 passes along or within the collar 308 to form a loop extending from the lateral extent of the collar 308. The first and second sutures 302, 304 form loops from the superior and inferior extents of the collar 308. Intersections 310 can secure the loops to each other with small loops or knots in the sutures, small fabric attachment pieces, or by small preformed devices resembling grommets placed on the suture to aid in securement. Other knot tying techniques known in the art can also be employed. Turning to FIG. 39, the collar is depicted within the subannular space where the loops surround a fascial autograft 314 which by pulling proximally the sutures 302, 304, 306 the graft is collapsed into contact with the annular wall in a sealing manner. The sutures can be made of known materials, e.g., biodegradable, bioabsorbable or bioresorbable Vicryl or biocompatible nylon. The collar can be made of a fabric material, e.g., polyester. During placement, one end of some or each suture can be passed through the inferior wall of the annulus and the other end can be passed through the superior wall surrounding the aperture. After the placement of the sling into the wall of the annulus, the fascial autograft is placed within the sling. The sutures are tightened to bring the tissues together and also to help reapproximate the aperture, as the collar size will be selected based on the surgeon's judgment according to the degree of reapproximation desired.

Figure 40:
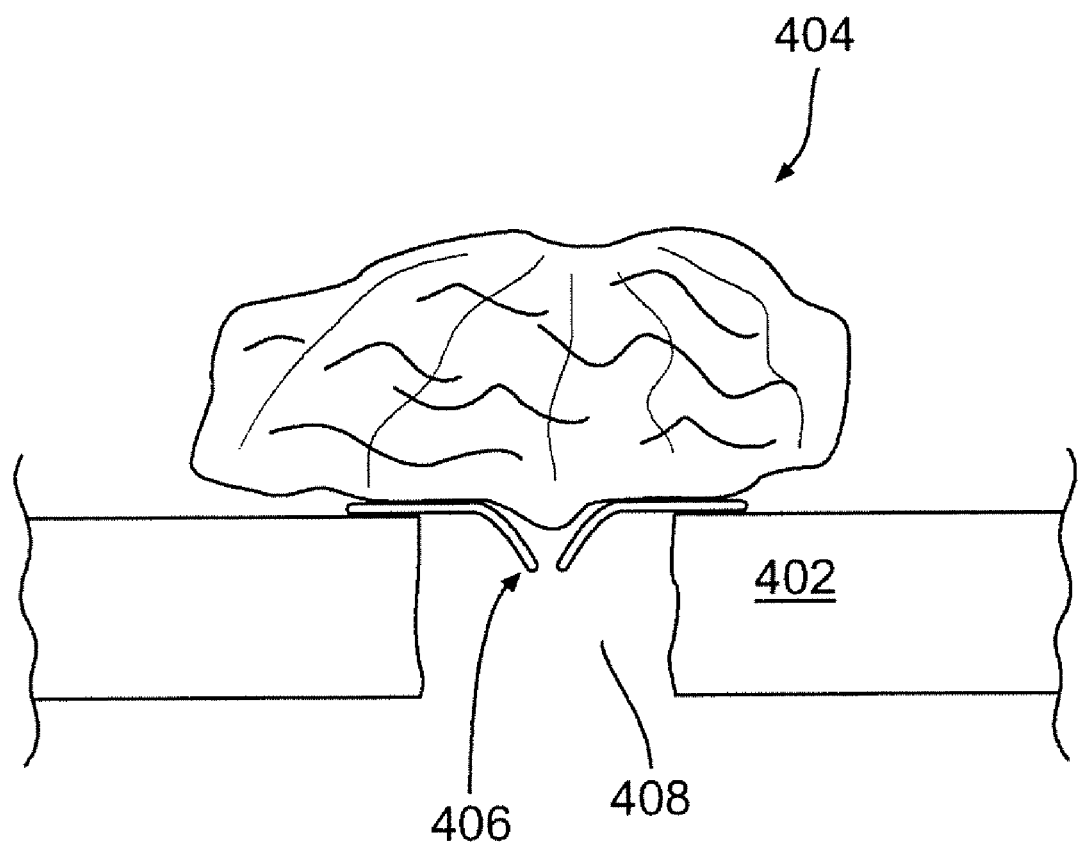
FIG. 40 shows a still further exemplary embodiment of the present invention using a bag to contain the patch/stent.
Figure 41A:
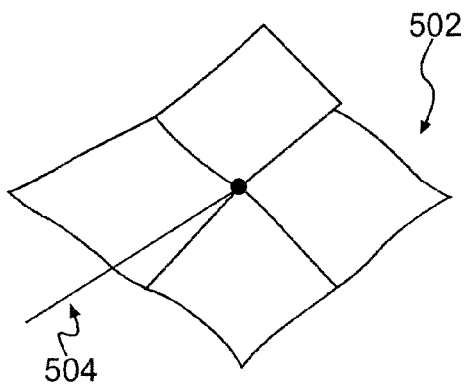
FIG. 41A-E show still further illustrative embodiments of the present invention having frames.
Figure 41B:
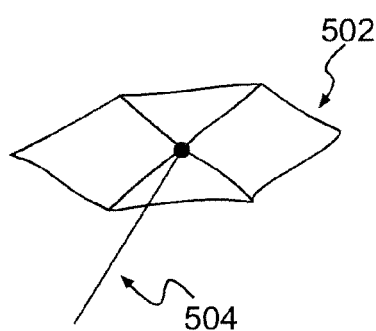
Figure 41C:
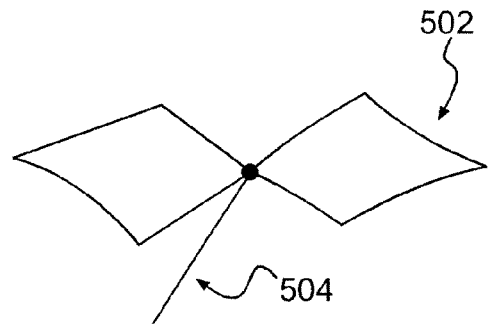
Figure 41D:
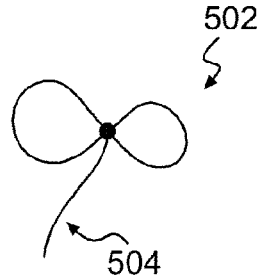
Figure 41E:
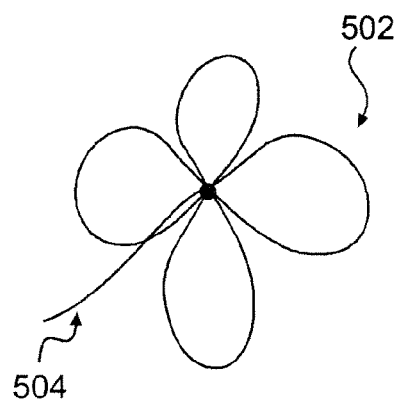

Other constructions can also be used to accomplish the same objective, such as a "bag" 404 formed of expandable PTFE as shown in FIG. 40. The bag is placed through an aperture in the annulus 402. Additionally, a one way seal 406 can be positioned behind the aperture 408. Suturing techniques for introducing cardiac valves could be employed to place the seal. It is understood that there could be multiple constructs to accomplish the same objective and this is only given as an example.

Figure 42:
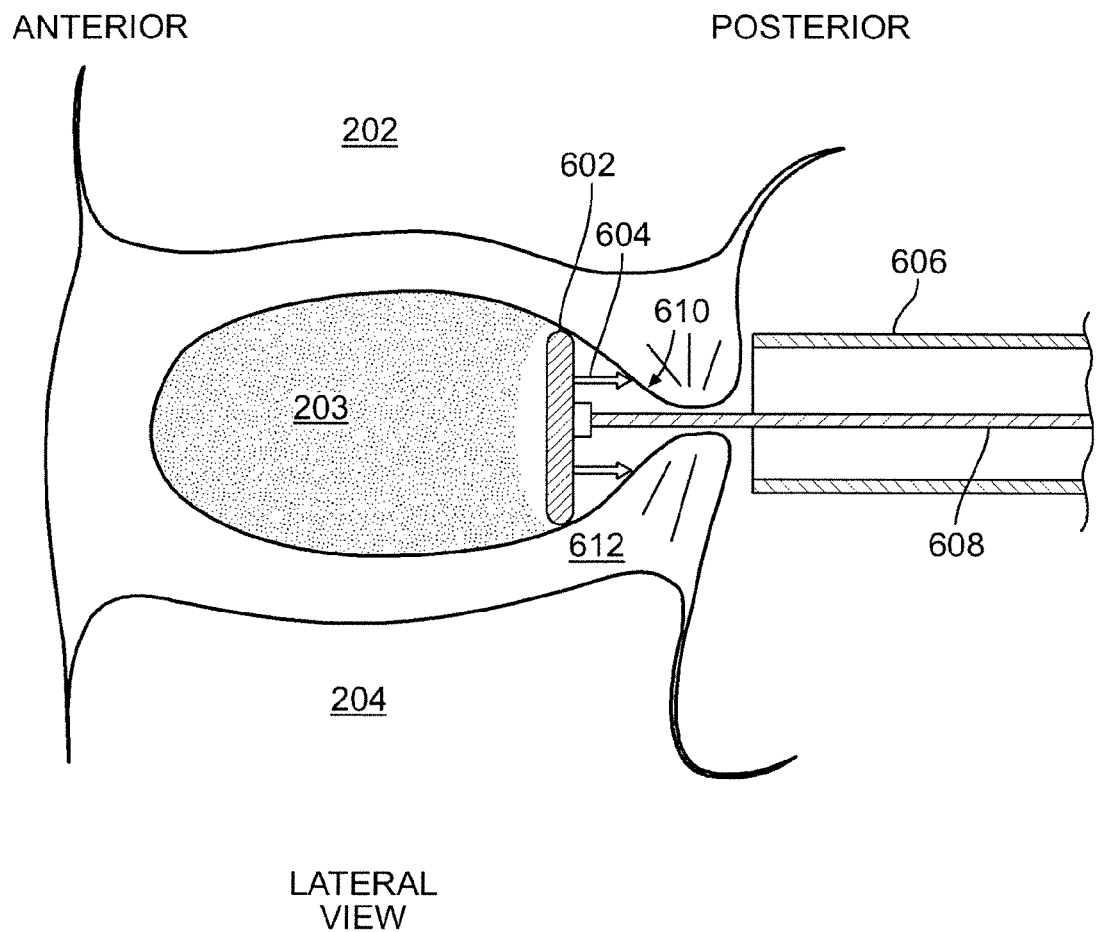
FIG. 42 shows an illustrative method for placing a barbed expandable patch in the subannular disc space.
Figure 43:
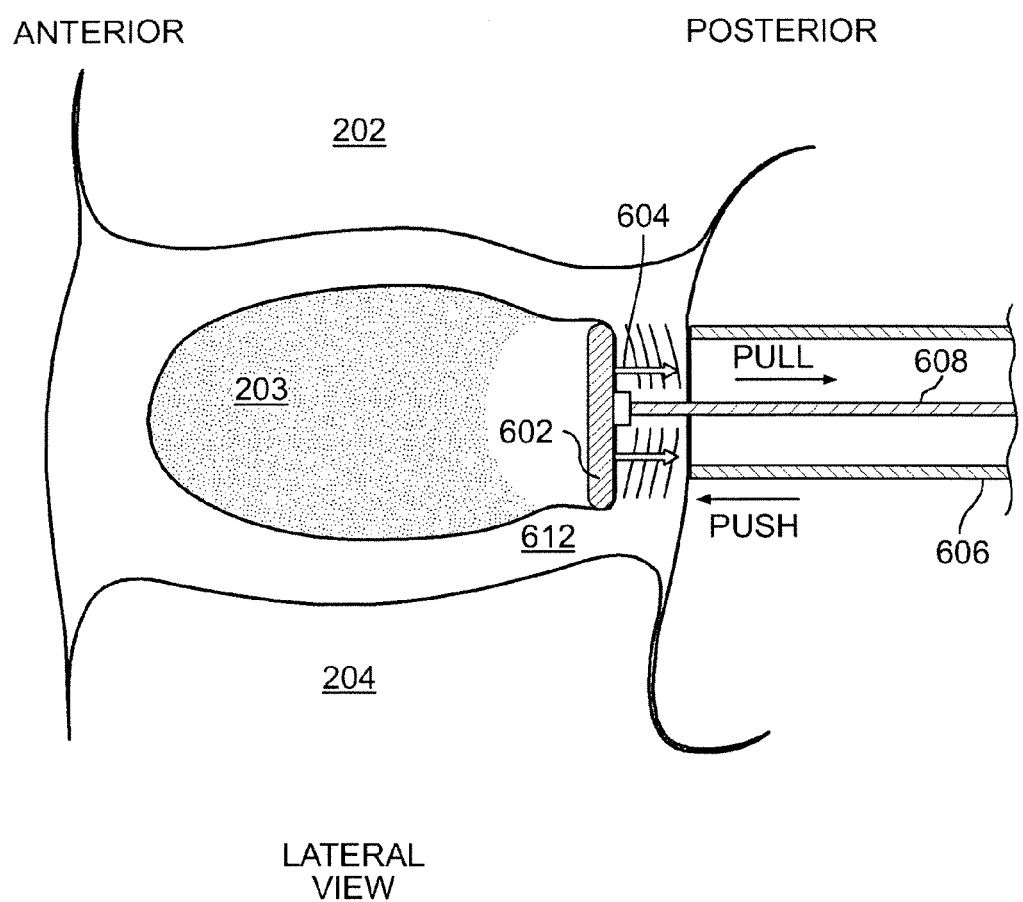
FIG. 43 shows the patch of FIG. 42 being fixed to the inside wall of the annulus fibrosus.

The are a variety of ways to affix the device to the subannular wall of the annulus in addition to those discussed hereinabove. The following exemplary embodiments are introduced here to provide inventive illustrations of the types of techniques that can be employed to reduce the time and skill required to affix the patch to the annulus, versus suturing and tying a knot. Discussed hereinabove is the use of sutures, staples and other fixation devices, such as those passed through slot 18 to affix the patch to the annulus as shown in FIG. 1. FIG. 20 also depicts the use of "barbs" on the surface of the stent to facilitate fixation to the annulus. In a simple example, as shown in FIG. 20, a patch/stent could be compressed, passed through a guide tube such as tubes 18, 18A shown in FIGS. 22 and 23, and expanded within the subannular space. As shown in FIG. 42, the expanded patch 602 is shown having barbs 604, along with detachable delivery tool 608 and guide tube 606. Once expanded, barbs 604 on the outer surface of patch 602 can be used to fix the patch into the inner wall 610 of the annulus 612 by pulling the patch back proximally, into the sub-annular wall 610, and pushing forward distally on the guide tube 606, thus driving the barbs 604 into the annulus and drawing the inner and outer tissues of the annulus together and reapproximating the disc on either side of the aperture, as shown in FIG. 43. After the placement of the patch, the delivery tool and guide tube are removed.

The advantage of this design described above is that it requires very little time and skill to place and secure the patch to the annulus while also drawing the tissues together.

Materials of the patch could be similar to materials discussed hereinabove. Anchoring barbs could be made of a biocompatible material, for example a metallic material (e.g., NiTi alloy, Stainless steel, Titanium), or a polymeric material (e.g., polypropylene, polyethylene, polyurethane). Anchoring barbs could also be a biodegradable/bioabsorbable material, such as a polyglycolic acid (PGA), a polylevolactic acid (PPLA), a polydioxanone (PDA) or for example a racemic polylactic acid (PDLLA). If the barbs included a biodegradable/bioabsorbable material, it is anticipated that the barbs might have sufficient holding strength for a sufficient period of time to allow the patch to be incorporated into the annulus during the healing process. The advantage of having the anchoring barb of FIGS. 42 and 43 being biodegradable/bioabsorbable is that after the incorporation of the patch into the annulus there may be no need for the barbs to provide fixation. However, barbs pointing toward the outer surface of the annulus could pose a long term risk of penetration out of the annulus due to migration, and potentially impinging on the nerve root and spinal canal. Biodegradable/bioabsorbable barbs address and advantageously reduce any long-term risk in this regard.

It is also possible that the barbs could be made of both a biocompatible component and a biodegradable/bioabsorbable component. For example, the very tip of the barb could be made of a biodegradable material. The barb could penetrate the annulus wall with a rather sharp point, but after degradation the point of the barb would become dull. In this embodiment, the point would no longer induce continued scar formation after the patch has been incorporated, nor pose a risk of penetrating out of the annulus onto the nerve root.

Another fixation means includes the passing of "anchoring bands" into the wall of the annulus, vertebral bodies (superior, inferior, or both), or the Sharpey's Fibers (collagenous fibers between the junction of the annular fibers and vertebral bodies). In the following example of anchors, the barbs or bands are affixed to the annulus/vertebral bodies/Sharpey's fibers. Another element, for example a suture, cinch line, or a staple is utilized to attach the anchor bands to the patch, and thus hold the patch in proximity to the inner wall of the annulus. In addition, these bands may re-approximate the tissues at the aperture.

Revisiting one example of using barbs to anchor the device is shown in FIG. 9, described hereinabove. Barbs or bone anchor screws 50 ands 52 are passed into the superior and inferior vertebral bodies 54 and 56, respectively. Superiorly, suture 40 is passed through the outer wall of the annulus, to the sub-annular space. The suture is then passed through the eyelet 53 of bone anchor 52 and then passed through the wall of the annulus from the sub-annular space to the outer wall of the annulus. The inferior end of the suture is similarly passed through the annulus, eyelet of the bone anchor, and back through the wall of the annulus. Both ends of suture 40 are tightened and tied. The advantage of this concept is that it allows for fixation of the device to a surface that is known to be present in all discectomy procedures—the vertebral bodies. Whereas, it is possible, depending on the location and size of a natural rent that there may not be sufficient annulus accessible to fixate the device directly to the annulus. In addition to providing a location for fixation, anchoring into the vertebral bodies may provide a more stable anchor surface.

Another example of fixating the device to inner wall of the annulus is shown in FIG. 29, and is further illustrated by FIGS. 44-47. As discussed hereinabove, with reference to FIGS. 22-30, a patch 120 is placed with a delivery tool 122, through the inner lumen of a guide tube 118, into the sub-annular space and then expanded. This step can also be seen in FIGS. 45 and 46, where a patch 702 is folded and passed through a guide tube 706 and is held by a delivery tool 704. Also shown is a anchor band or staple 709 and an anchor band delivery device 708. Within the guide tube, or within the delivery tool, there is a suture line or cinch line 710 that is attached to the center of the patch 702. This can be seen in FIG. 44a with the guide tube 706 removed. As seen in FIGS. 45C and 46A, the guide tube 706 is retracted after the patch 702 has been expanded and deployed. Next, an anchor band delivery tool 708 is used to deliver one or more "bands" 709 onto the outer surface of the annulus. These are intended to be anchored into the wall of the annulus with barb shapes that do not allow for the barbs to be pulled back through the annulus. The anchor bands resemble a construction of a "staple". The bands could actually be constructed by connecting two barbed elements with, for example, a suture between the two barbed elements. The barbs and the connection band between the barbs could be constructed of the same material or of different materials. For example, the barbed part of the anchor band could be a biodegradable/bioabsorbable material (such as polyglycolic acid) or could be constructed of a metallic or polymeric biocompatible material (e.g., titanium, NiTi alloy, stainless steel, polyurethane, polypropylene). In addition, the band that connects these barbs can be constructed of materials that are similar to the barbs, or different materials. For example, the connection band could be a biodegradable/bioabsorbable suture, such as Vicryl, or a biocompatible material such as polypropylene. In addition, it is possible that these elements are constructed from multiple materials to accomplish the objective of anchoring into the annulus and providing for a fixation site to draw the patch within proximity of the sub-annular wall.

Figure 44A:
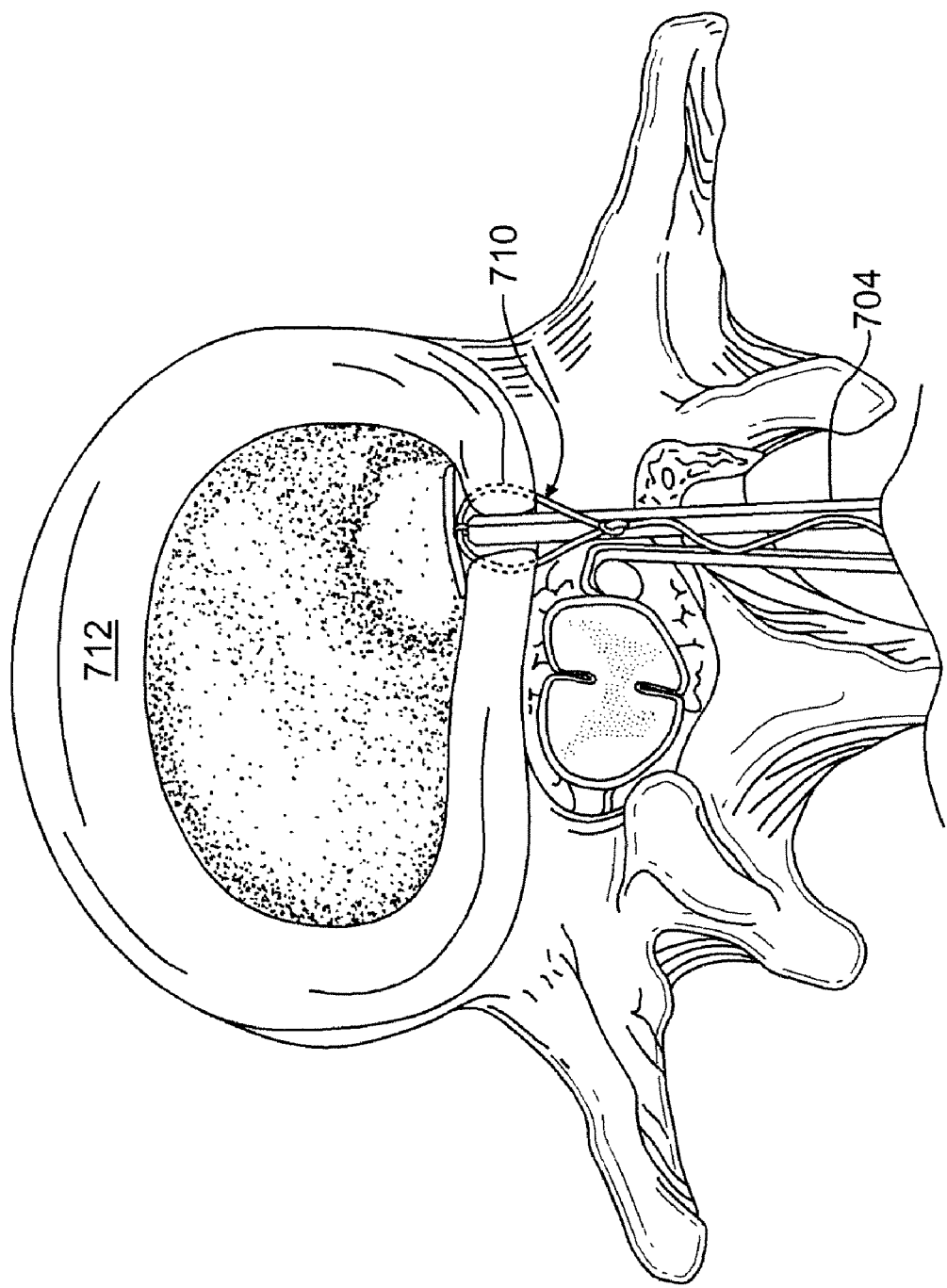
Figure 44B:
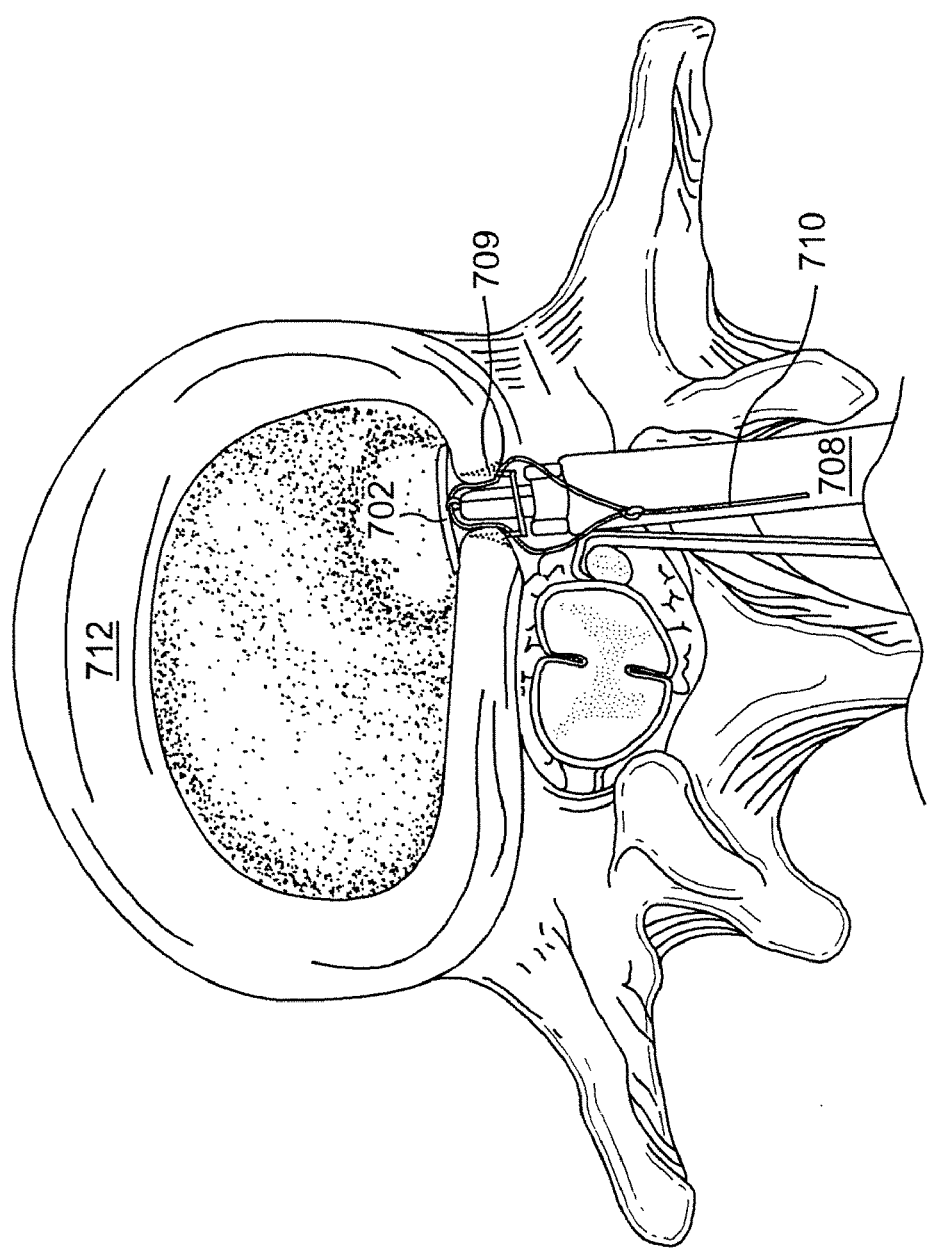
Figure 44E:
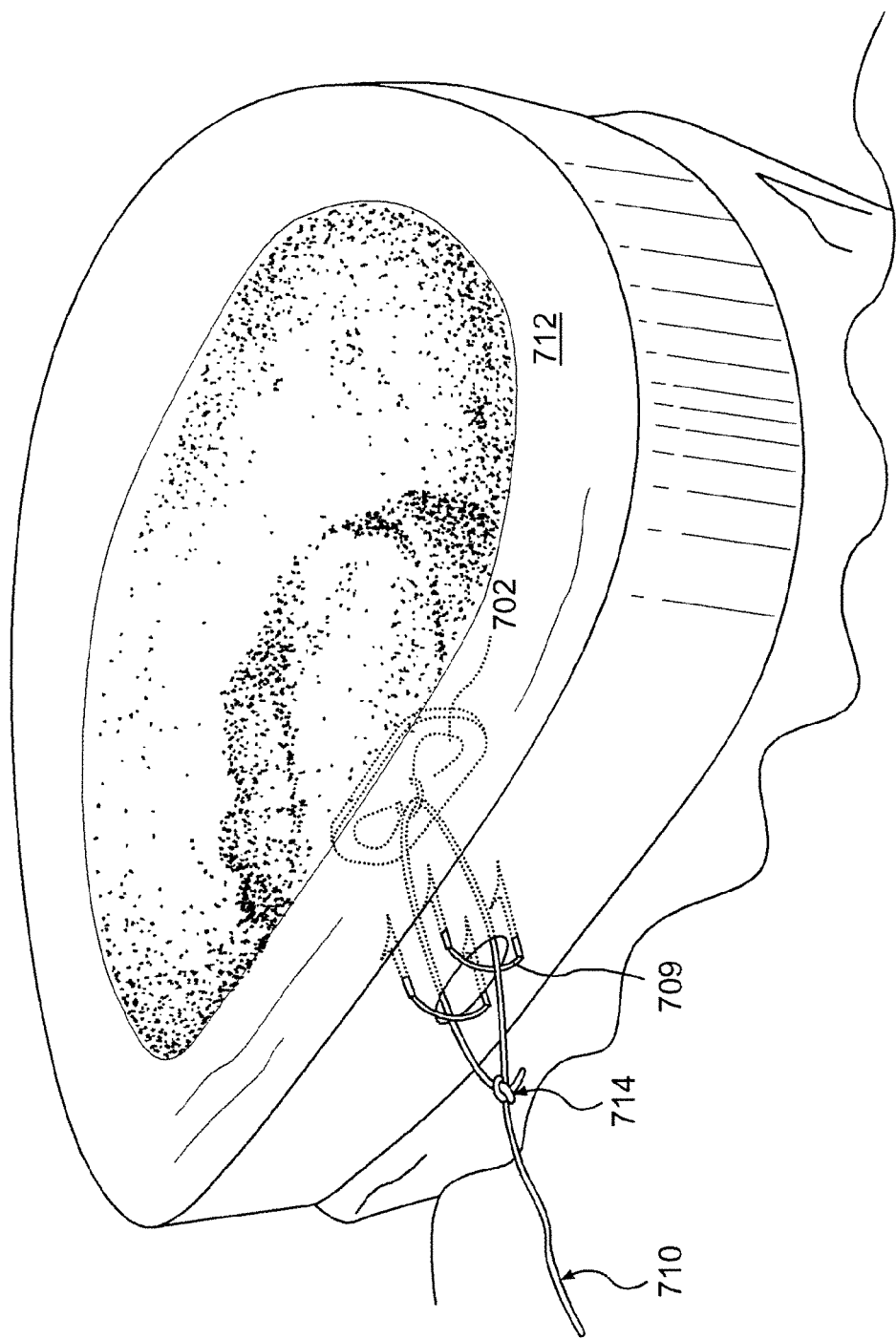
Figure 44F:
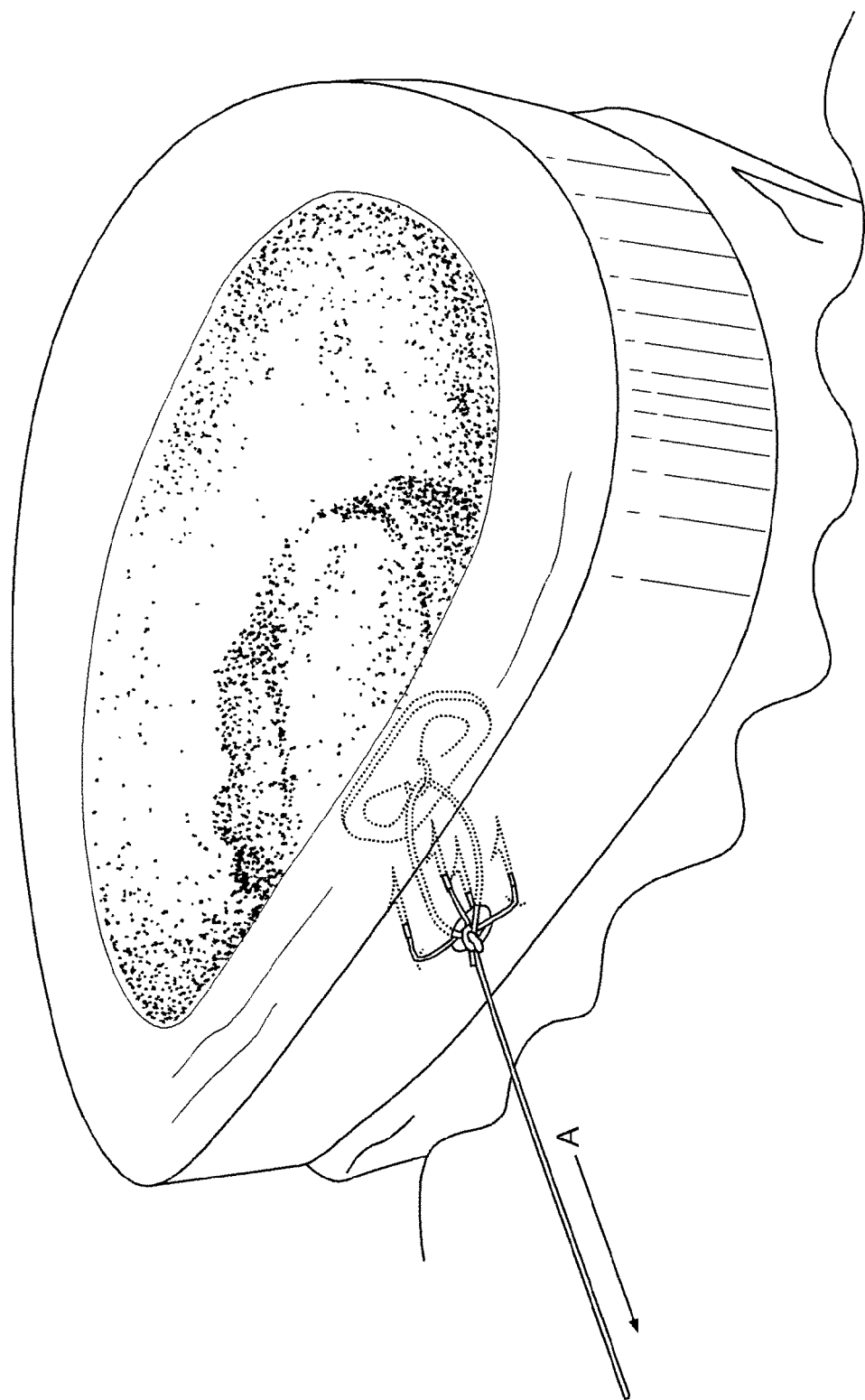
Figure 44G:
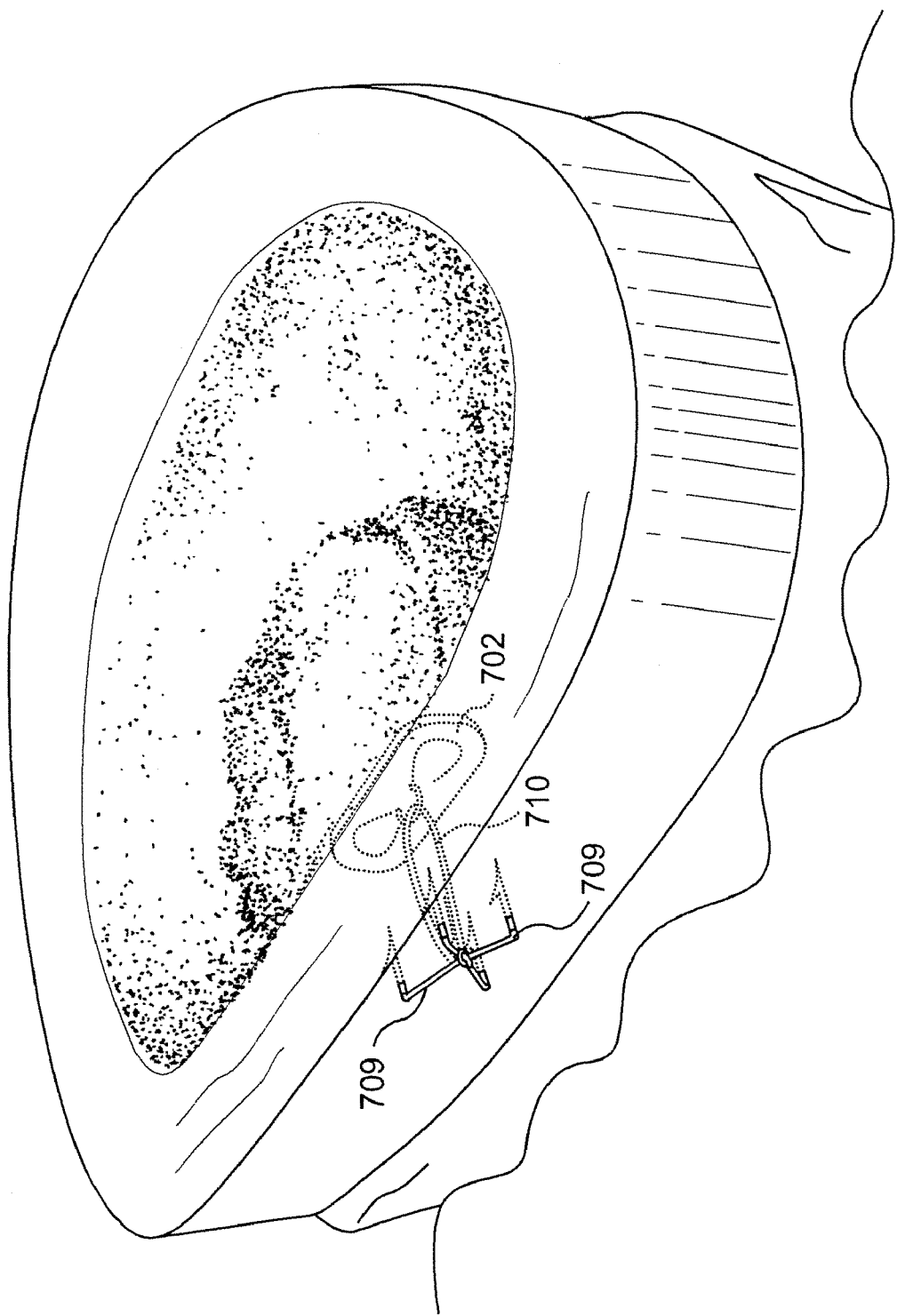
Figure 45A:
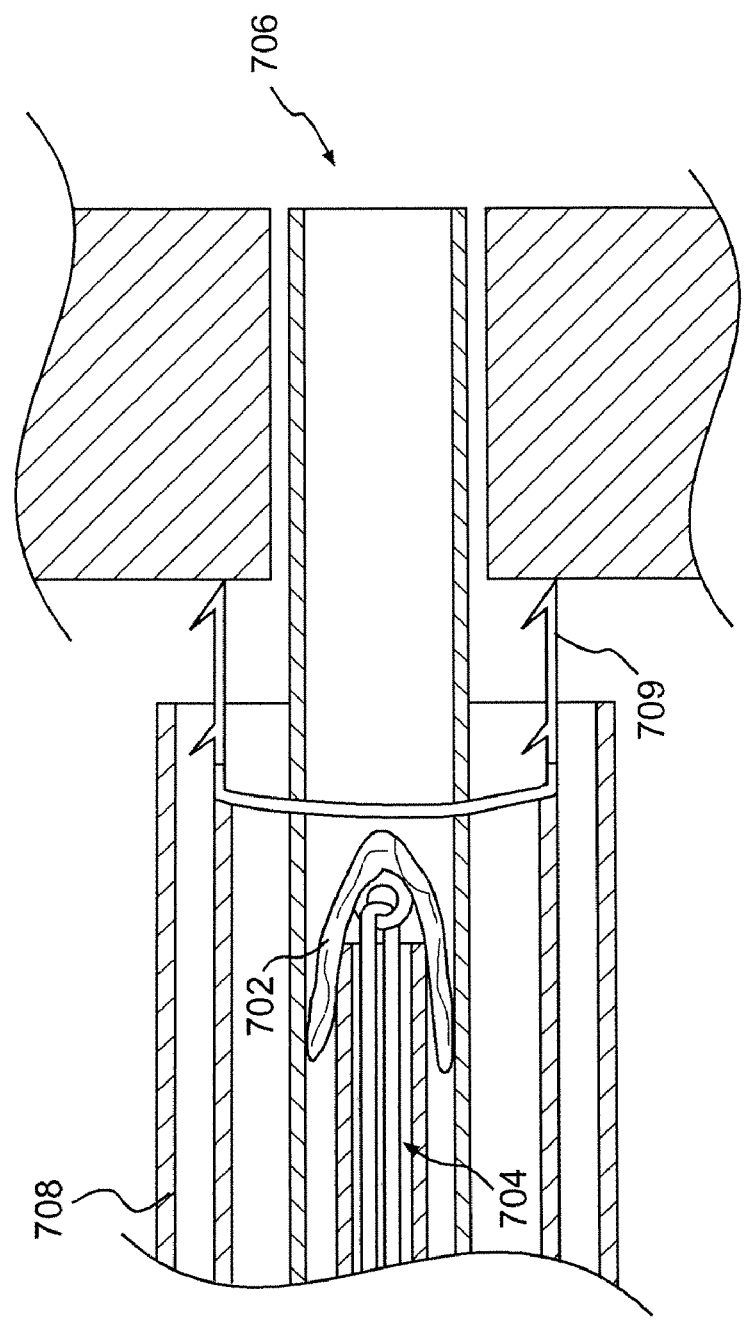
FIGS. 45A-C schematically depict a still further embodiment of the present invention where an expandable stent/patch is tethered in situ using a cinch line.
Figure 45B:
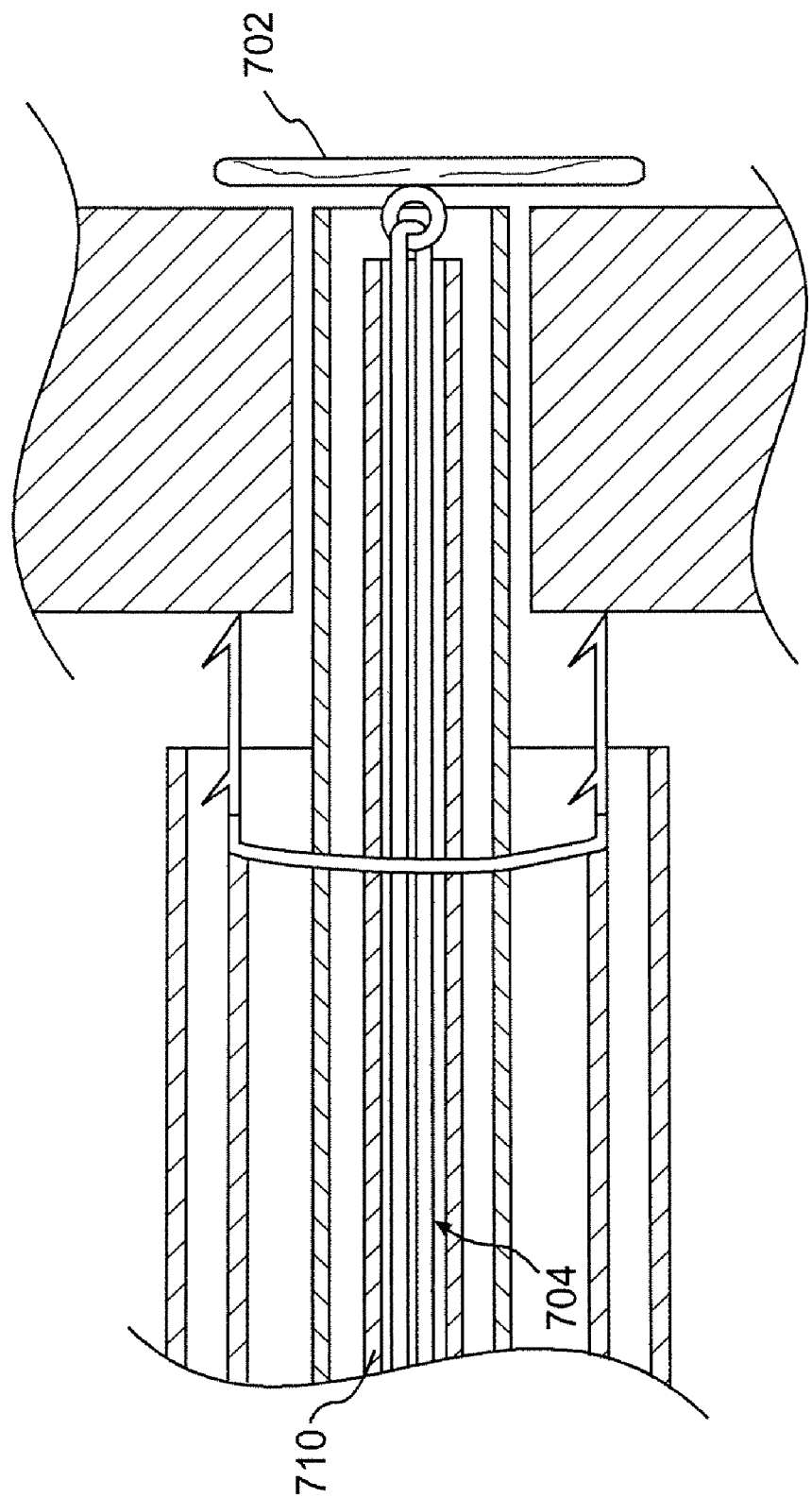
Figure 45C:
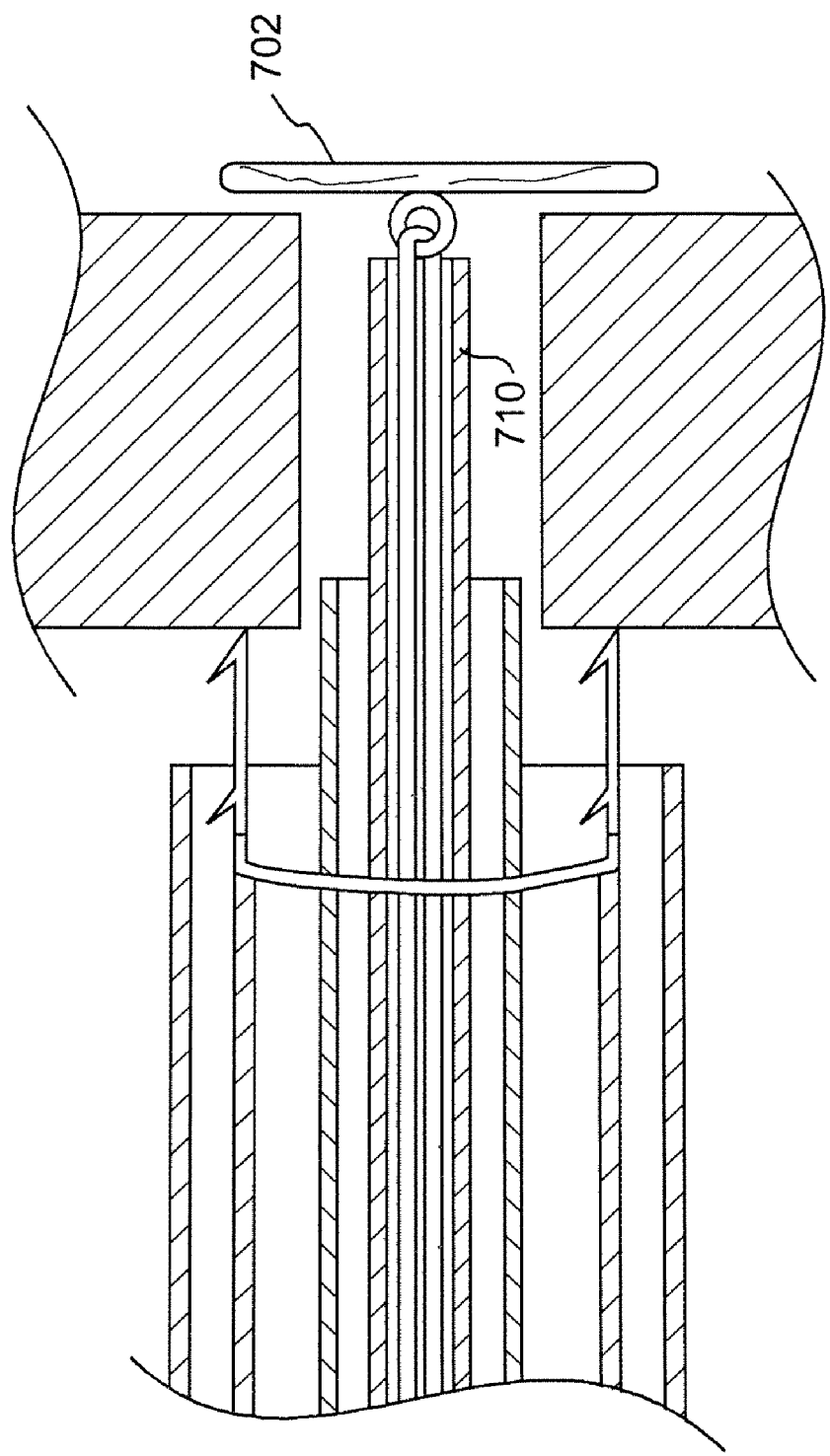
Figure 46A:
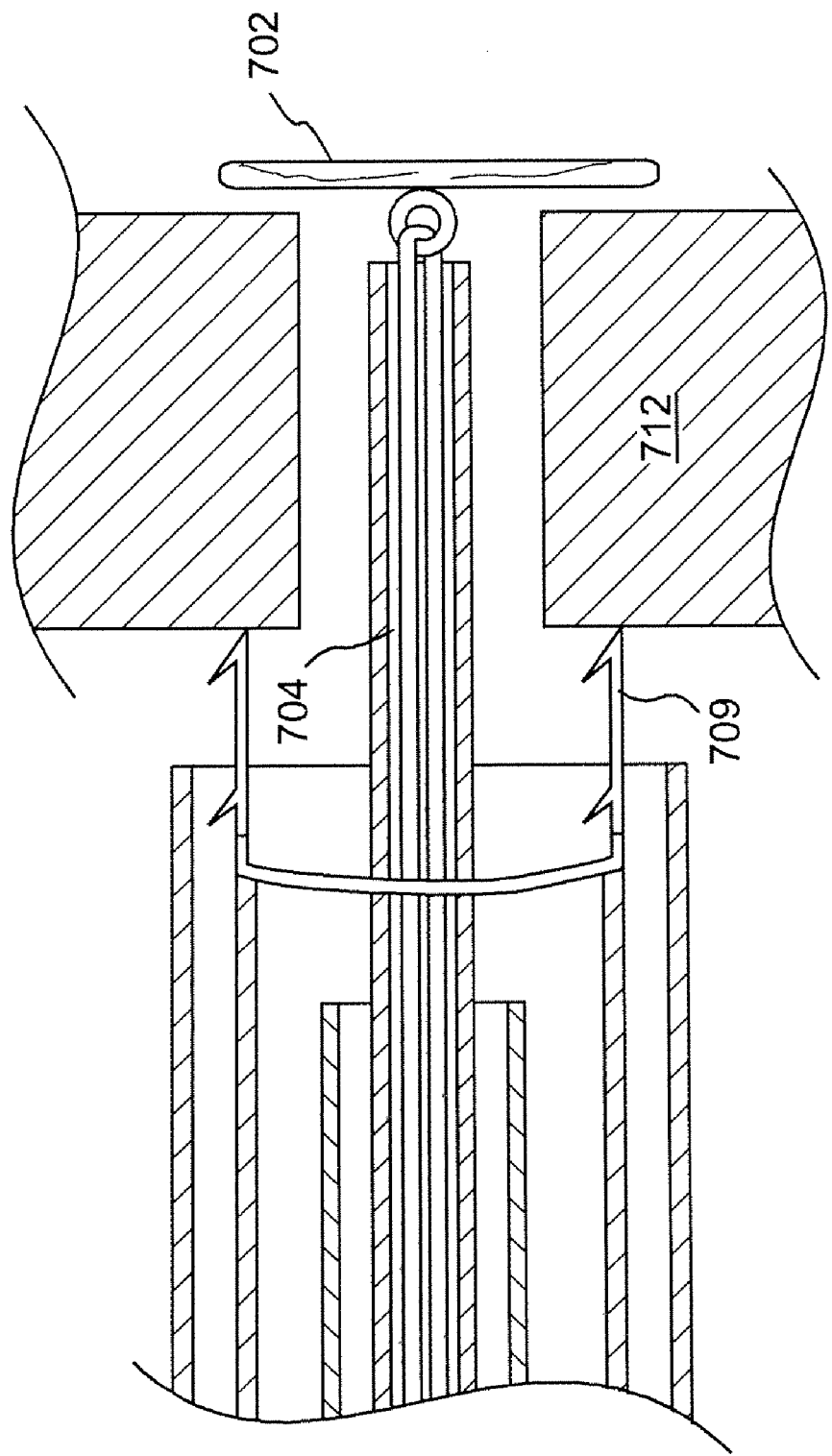
Figure 46B:
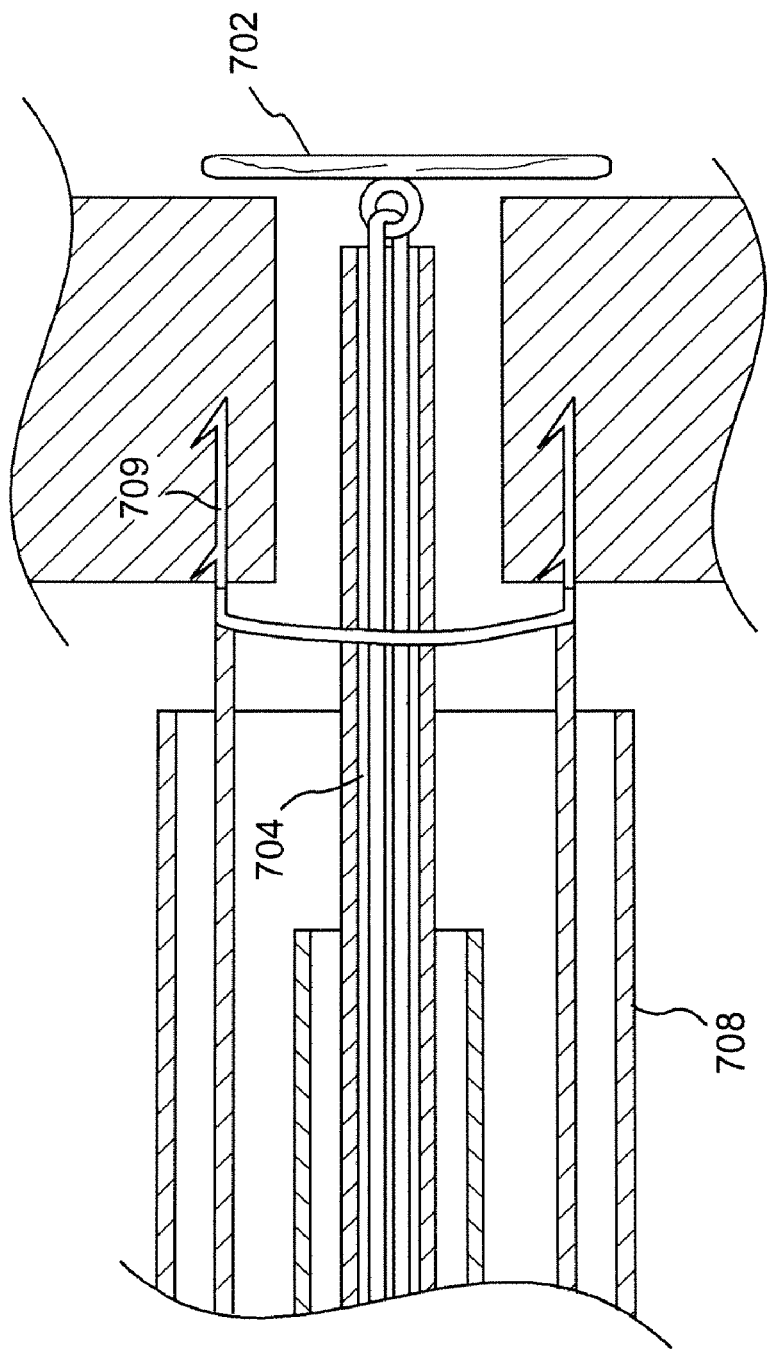
Figure 47A:
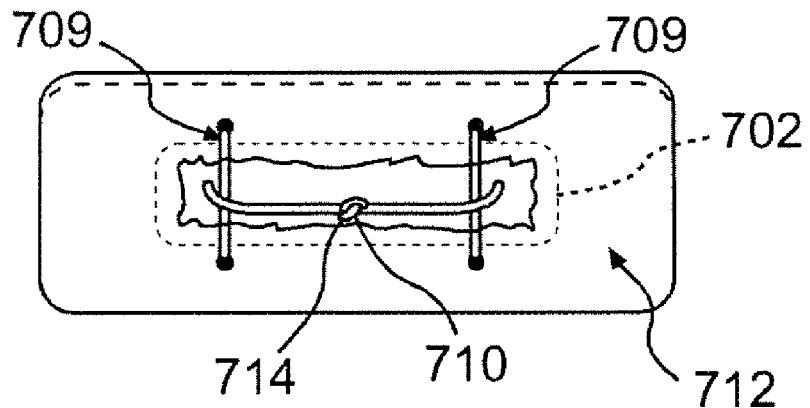
FIGS. 47A-B show an illustrative embodiment of a suturing arrangement for securing a patch/stent in the annulus.
Figure 47B:
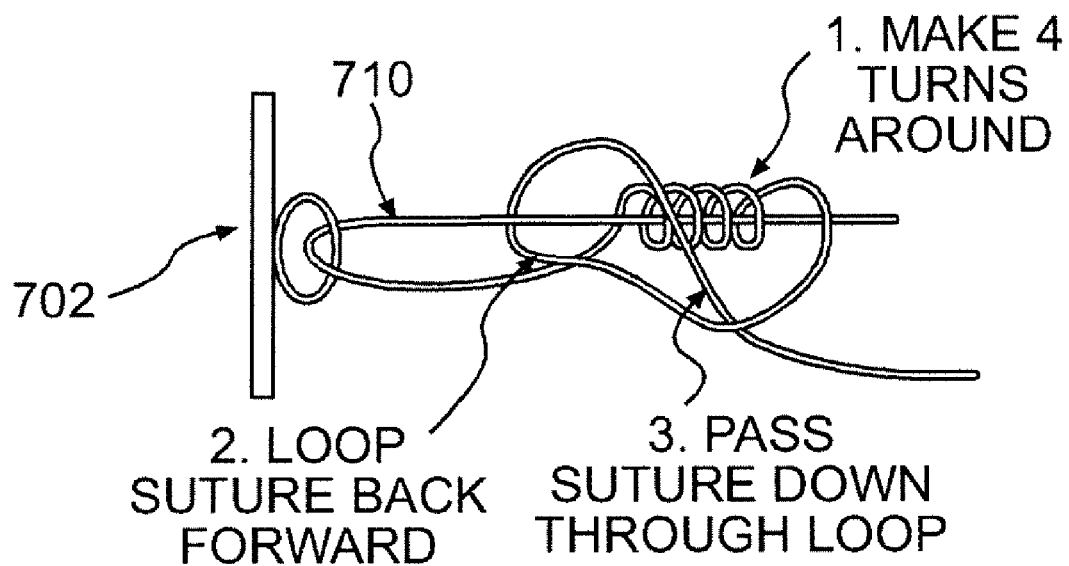

FIGS. 44B and 44C show the placement of the anchor bands 709 into the annulus 712 with the anchor band delivery tool 708. FIGS. 46A and 46B schematically show the placement of the anchor bands 709 into the wall of the annulus 712 and the retraction of the anchor band delivery device 708, with the patch delivery tool 704 still in place. FIG. 44D depicts a representative anchor band 709, having a pair of stainless steel barbs 709" connected by a suture 709'. FIG. 44E shows the patch 702, anchor bands 709, and cinch line or suture 710 with the delivery tools removed, prior to drawing the patch and the tissues of the annulus together. In this embodiment there is a pre-fabricated knot 714 on the cinch line, which is described further in FIG. 47B, although other knots are possible. FIG. 47a also shows a posterior view of the patching of the annulus with this device with knot 714. In this stent/patch 702 a pair of loops of 7 mm suture 709 are shown, which engage the cinch line and slip knot. These suture loops connect to the barbs directly, as in FIG. 44, or loop to surgical staples, or are placed directly into the annulus. The presence of a pre-fabricated knot on the cinch line makes the process of repairing quicker since there is no need to tie a knot. It also facilitates drawing the tissues together. The use of the cinch line and a pre-fabricated knot can be placed by, for example, an external tube such as a knot pusher. FIG. 44E is similar to the FIG. 29 described hereinabove prior to "tying" the knot 145. FIG. 44F shows the drawing of the patch and the annular tissues together by pulling on the suture in the direction "A" indicated by the arrow. In this case, the Knot Pusher has been removed from the cinch line 710. The suture 710 is drawn proximally to draw the patch 702 into engagement with the inner wall of the annulus to seal the aperture from within, as well as draw the walls of the annulus together to reapproximate the annular aperture. FIG. 46C and FIG. 44G show the cinch line suture 710 tied and drawing the annular tissues together, after the excess suture line has been cut. It is also apparent from this device, fixation and delivery system that the outer surfaces of the aperture are also drawn together for re-approximation.

The cinching of the bands and the patch also allows for taking-up the slack that allows for the accommodation of varying sizes. For example, the thickness of the annular wall surrounding the aperture can vary from 1 mm up to 10 mm. Therefore, if the anchor bands have a set length, this design with an cinch line accommodates different dimensions of the thickness of the wall of the annulus by drawing the "slack" of the bands together within the aperture.

Figure 48A:
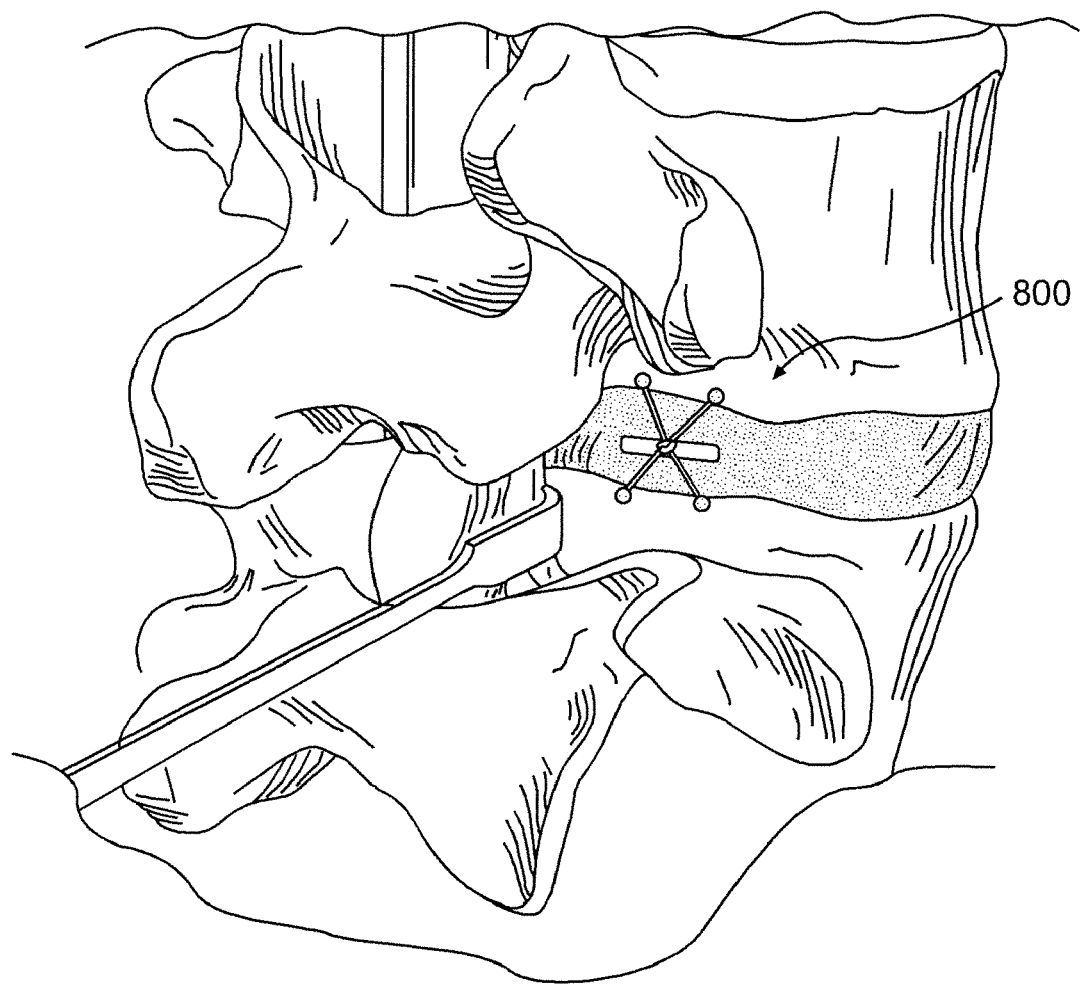
FIG. 48A-B depict a still further illustrative embodiment where fixation sutures are placed into the vertebral body or the Sharpey fibers.
Figure 48B:
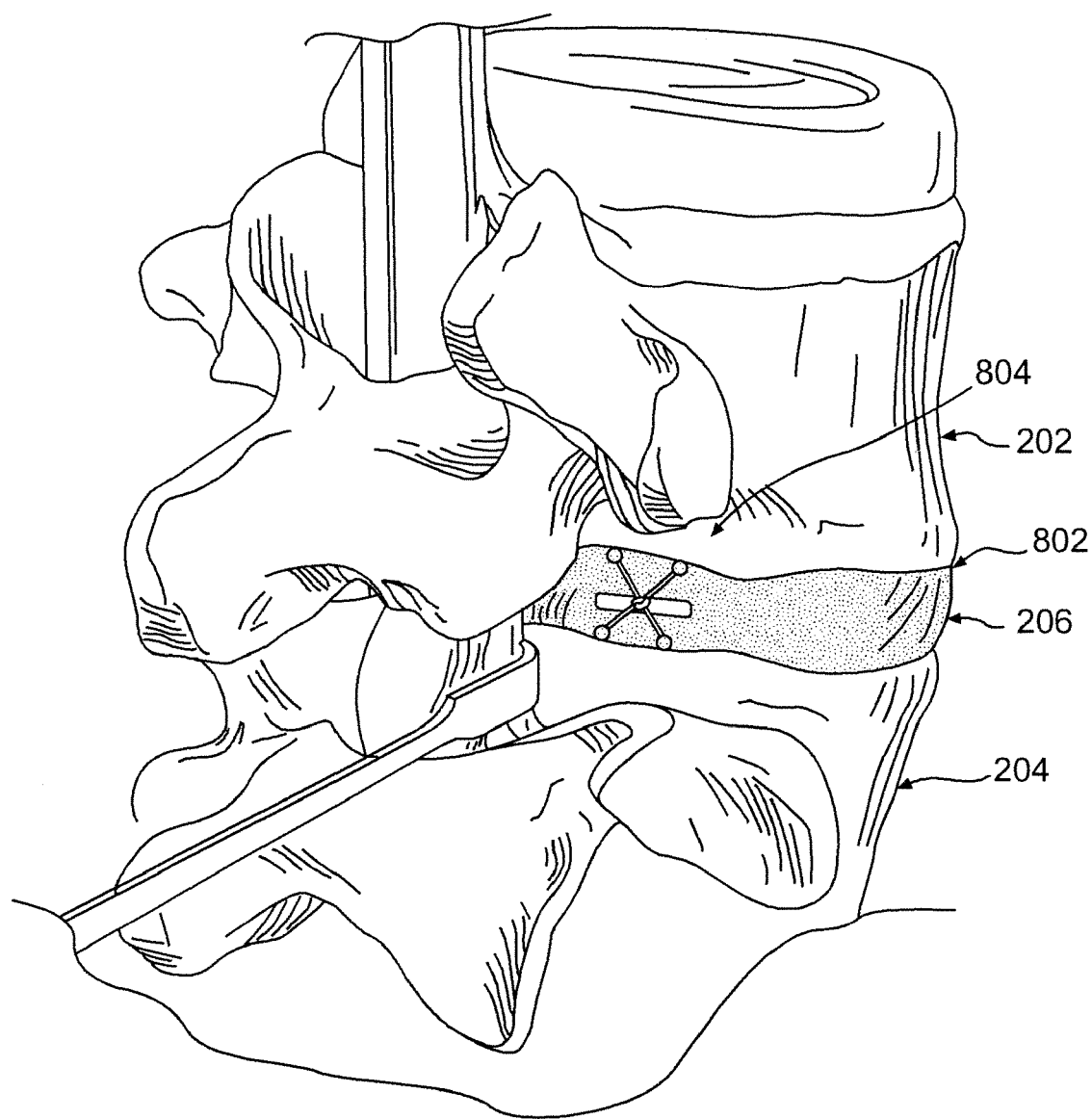

Although it has been described here as patch placement that involves two lateral anchor bands with a suture to draw the patch, bands and tissues together, one or more bands could be used and two bands is only an example. Furthermore, the anchor bands were placed with the barbs in a superior-inferior fashion. One skilled in the art would recognize that these could be placed at different locations surrounding the aperture. Moreover, although it was described that the bands are placed into the annulus, these anchor bands could also be placed in the vertebral bodies as shown in FIG. 48A generally at 800, or the Sharpey's Fibers 802, as shown in FIG. 48B generally at 804.

Although the patch depicted in the example above does not have barbs attached to the patch, it is also possible to have the barbs as described hereinabove to further promote the fixation of the patch to the inner wall of the annulus.

Figure 51:
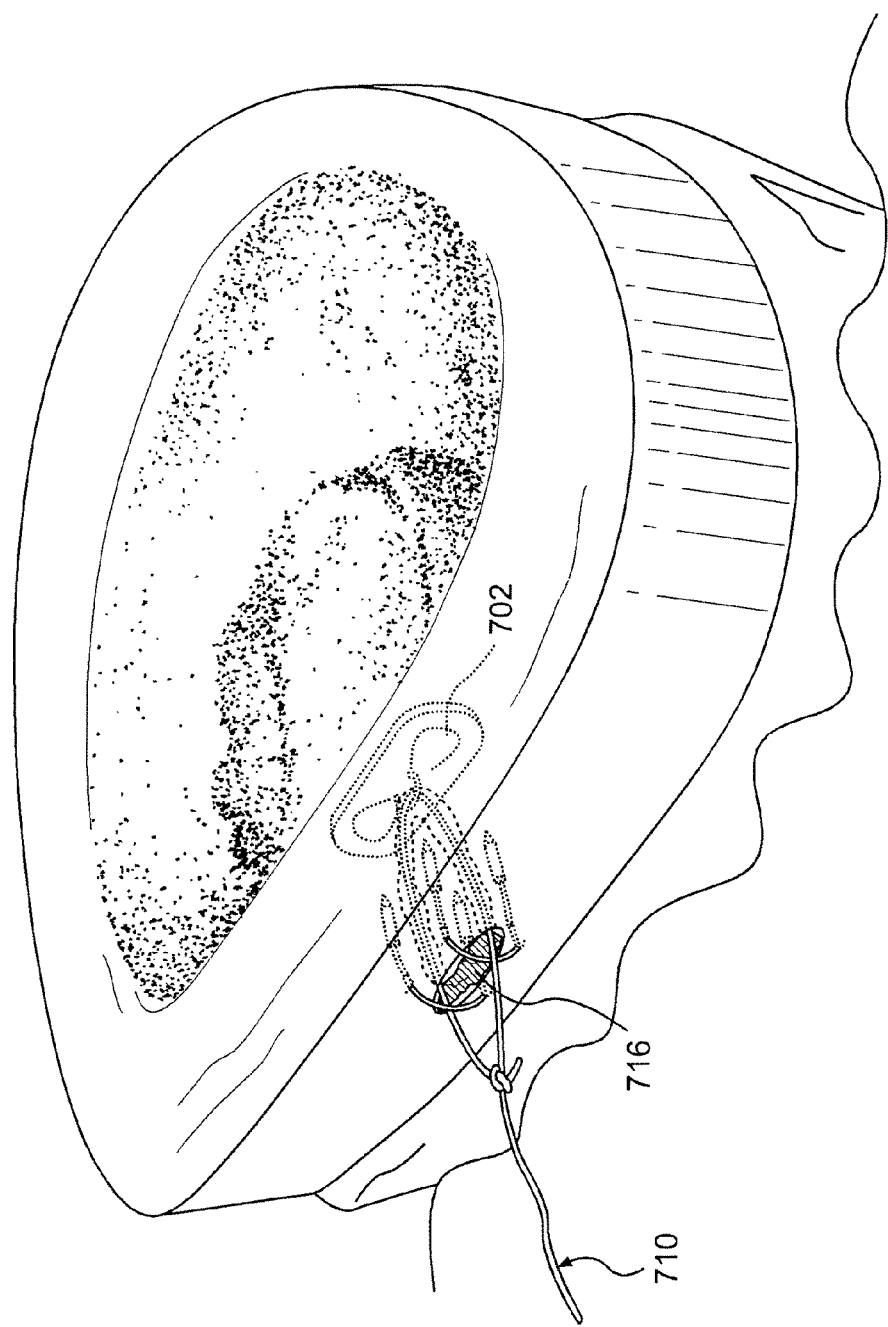
FIG. 51 depicts an exemplary use of filler tissue within the aperture during placement of a patch/stent tethered by a cinch line.

Finally, although the drawings depict an aperture that lends itself to re-approximating the tissues, it is conceivable that some apertures, whether natural or surgically made, may be relatively large and therefore might require the placement of additional material within the aperture to act as a scaffold for tissue in growth, between the patch on the inner wall of the annulus and the anchor bands located on the outer wall. An example of material to fill the aperture might include autograft para-spinal fascial tissue, xenograft, allograft, or other natural collagenous materials. The filler material could also be of a biocompatible material such as a Dacron material. FIG. 51 shows the illustrative filling of an aperture with implant material 716 prior to cinching the suture 710.

Figure 49A:
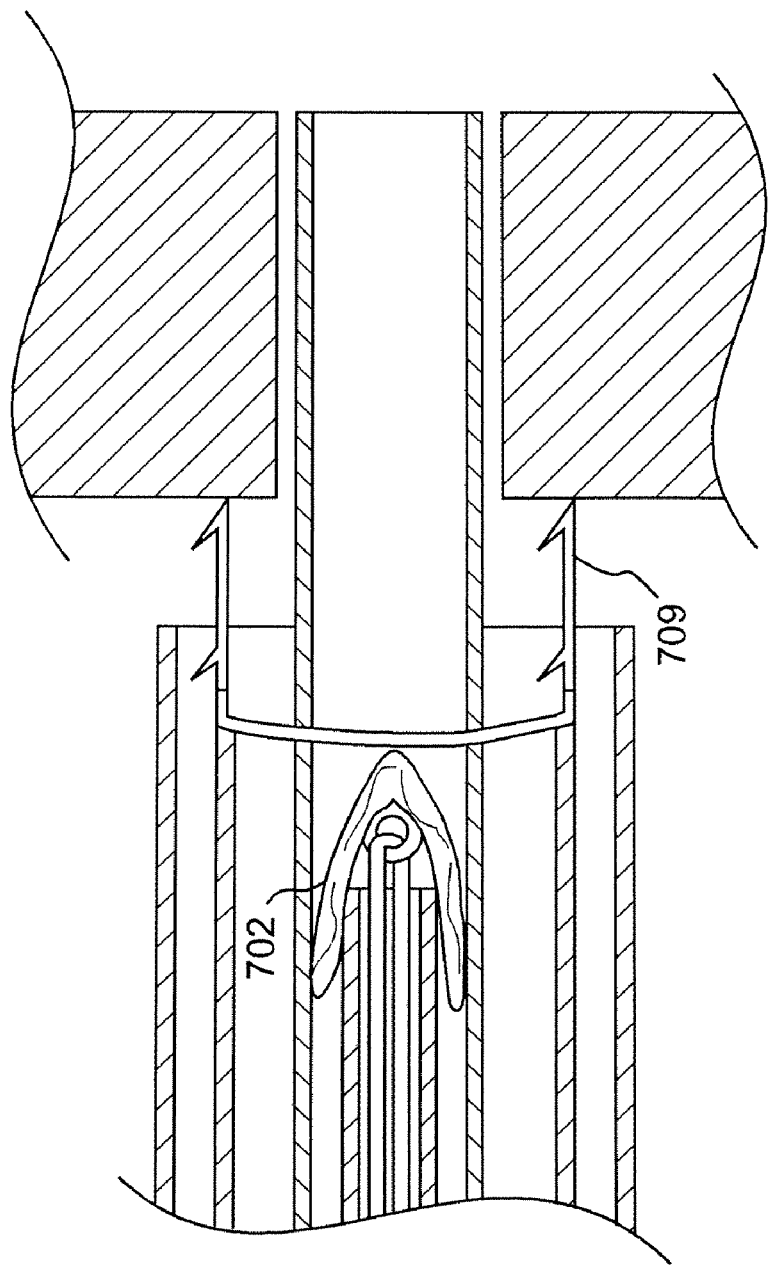
FIGS. 49A-C schematically depict a still further embodiment of the present invention where an expandable stent/patch is tethered in situ using a cinch line.
Figure 49B:
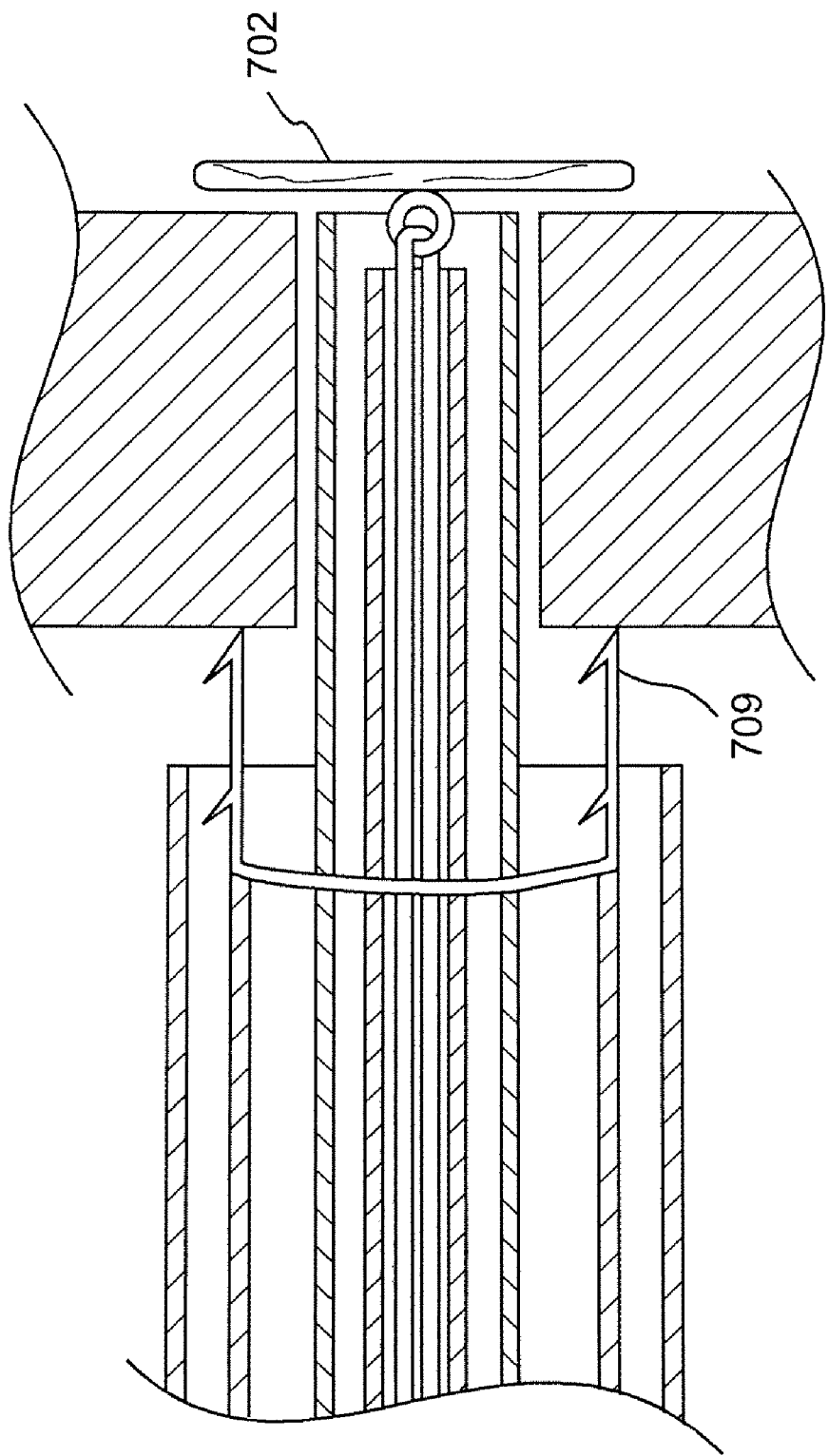
Figure 49C:
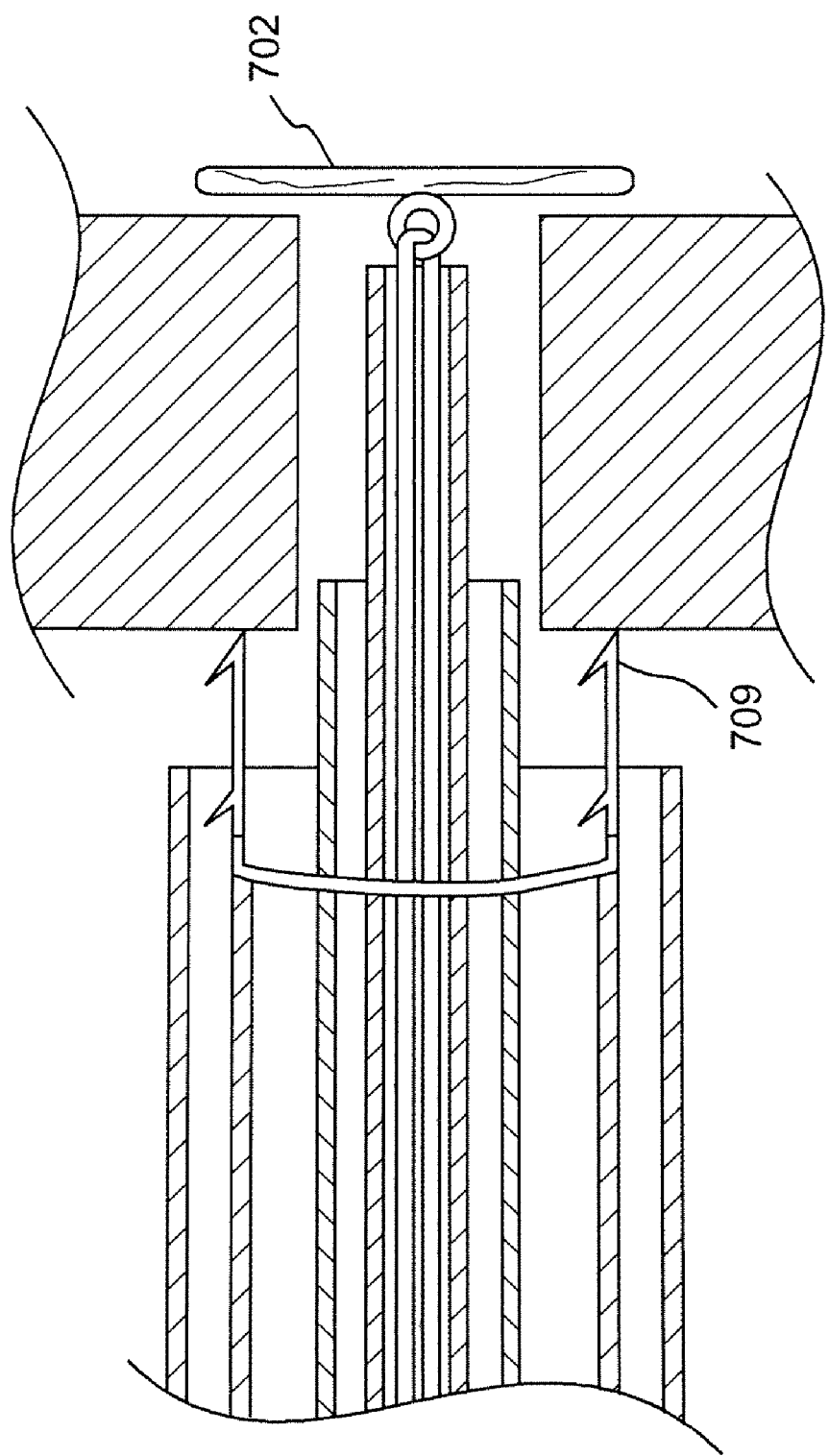
Figure 50A:
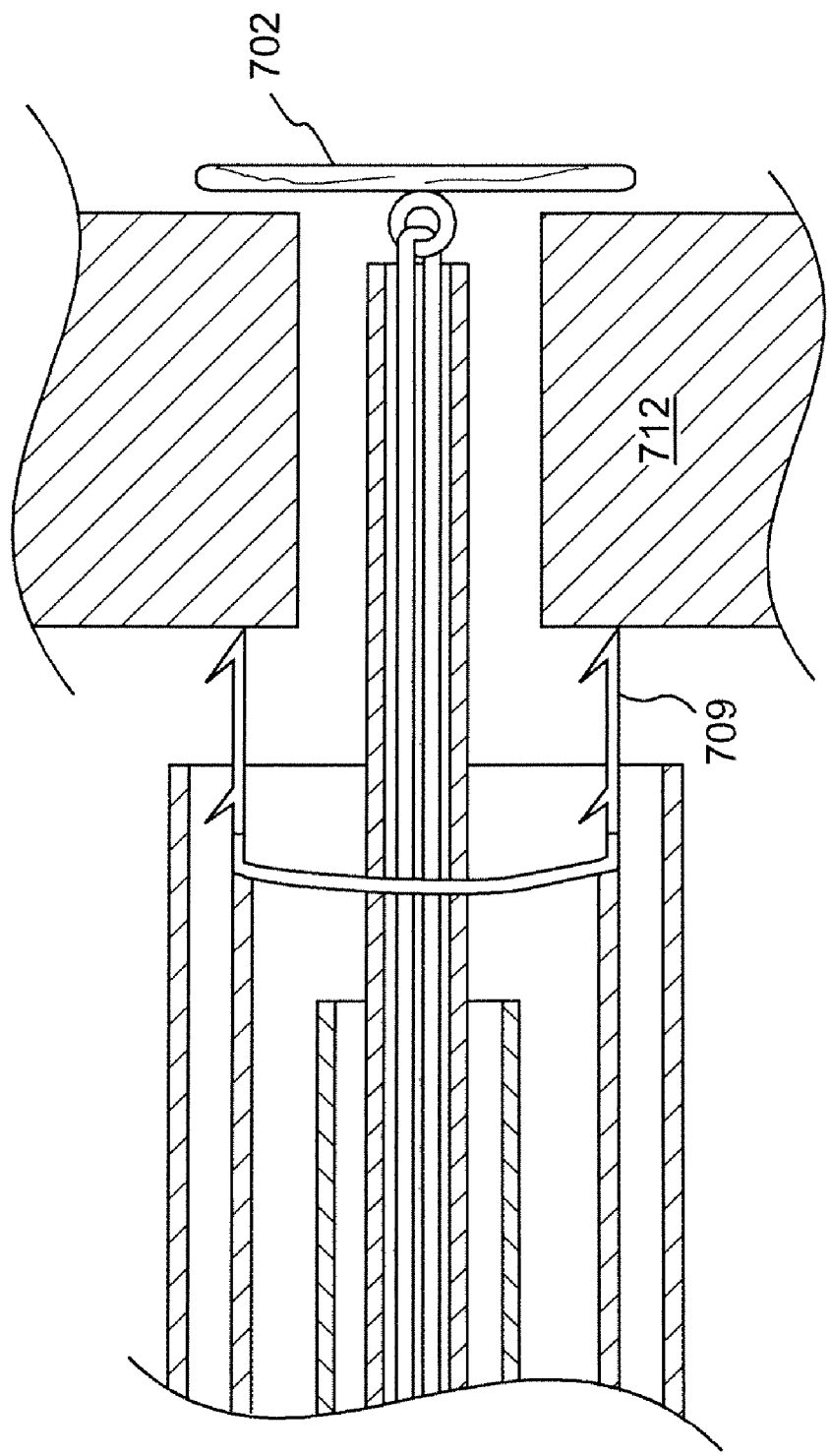
Figure 50B:
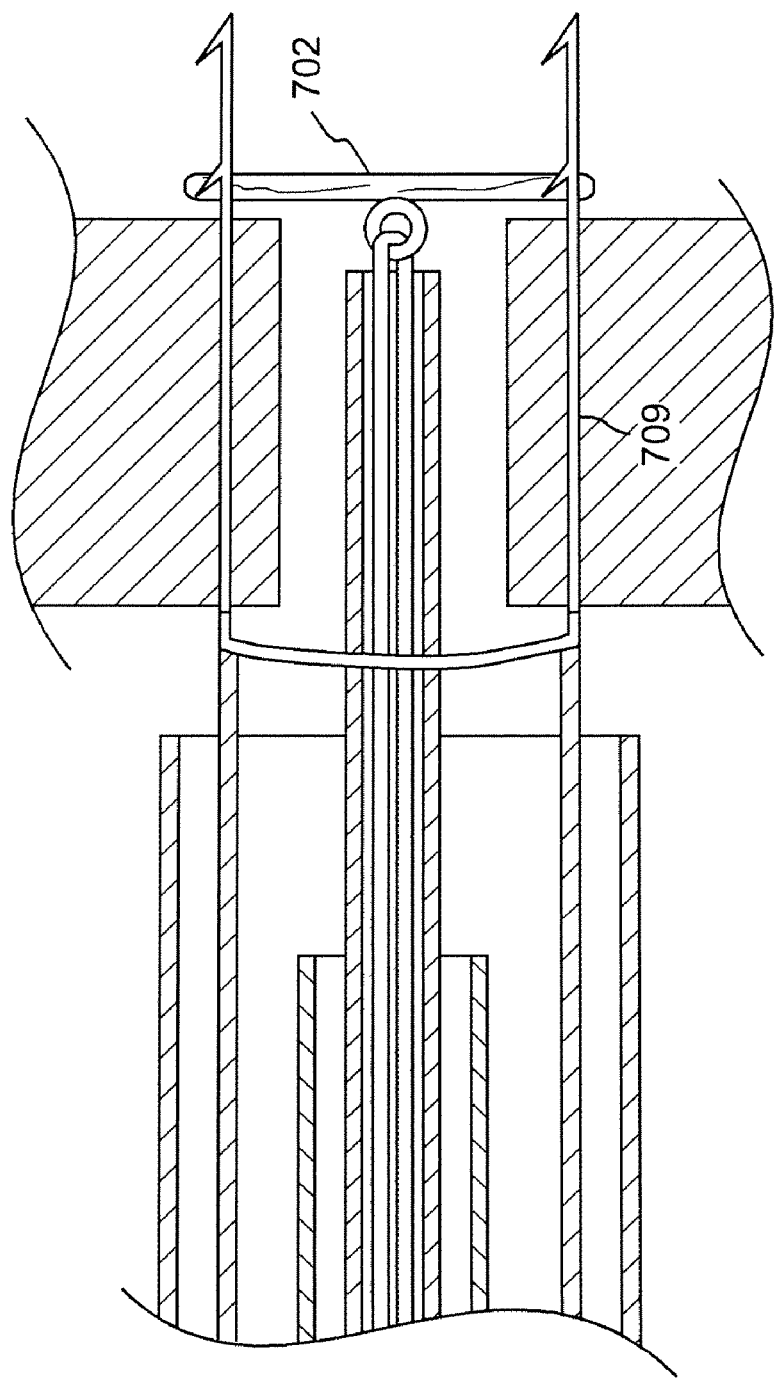

As an alternative embodiment of the present invention, the anchor bands 709 as described previously (anchor bands into annulus) could be sufficiently long enough to pass through the annulus and then through the patch. The barbs in this embodiment have an engaging involvement with the patch. This concept was previously discussed hereinabove in connection with FIG. 30. Further illustration of such a system is schematically shown in FIGS. 49 and 50. Passing the barbs through the patch, in this embodiment, provides additional security and safety of reducing the possibility that the barbs may migrate after implantation. In this application of the invention, the suture cinch line may (FIG. 50) or may not (FIG. 30) be used in addition to the anchor bands to draw the tissues together and reduce tissue movement surrounding the aperture.

Figure 52A:
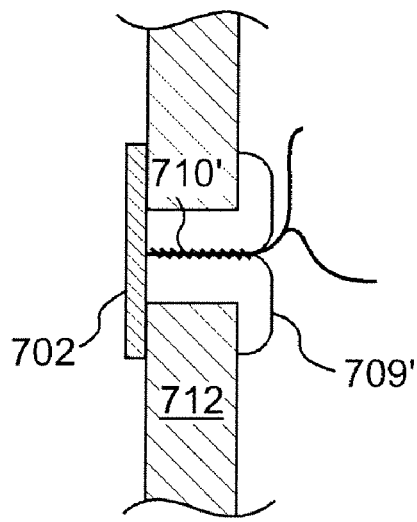
FIGS. 52A-E shows exemplary embodiments of various additional patch/stent fixation techniques.
Figure 52B:
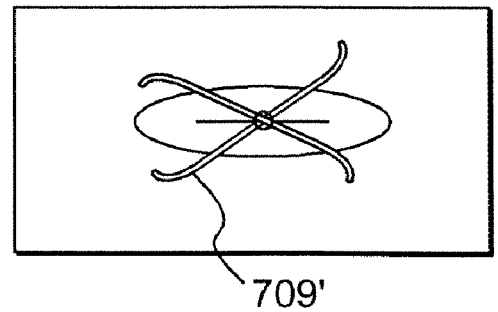
Figure 52C:
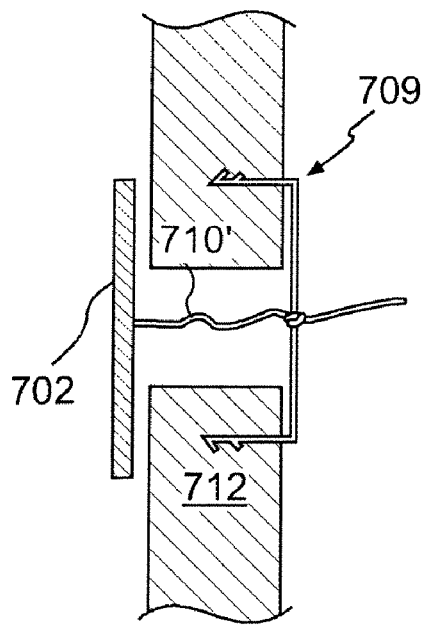
Figure 52D:
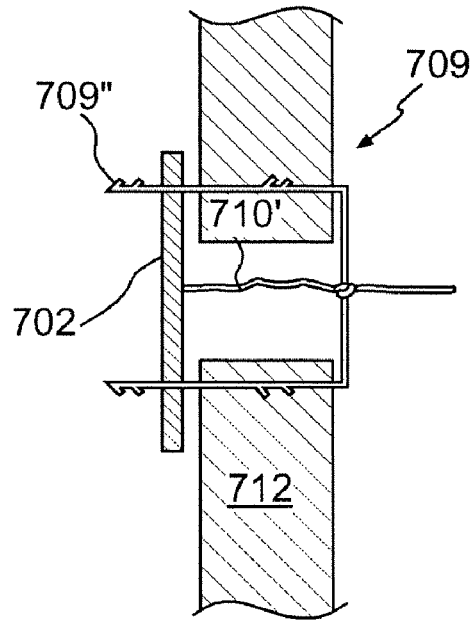
Figure 52E:
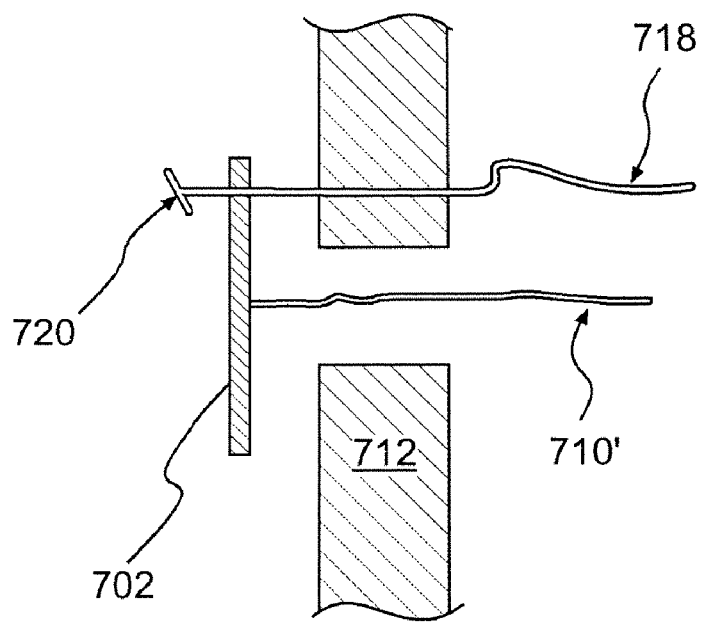

In addition, although the bands shown in FIGS. 49 and 50 take the form of a "barb", they could as easily take a form of a simple T-barb 720, as shown in FIG. 52E, or a C-type element wherein the object is to have irrevocable engagement with the patch device 702 after the penetration through the patch. A T-type attachment, when aligned longitudinally with the suture, passes through the patch. The T section then rotates to prevent the suture anchor from being pulled back through the patch. In another embodiment a "C" retainer made of a superelastic material may be attached to the end of the suture band. The C retainer is loaded into a needle wherein it is held straight. The needle is used to pass the C retainer and suture through the patch and deploy the retainer in a second configuration in the shape of a "C".

It is also foreseen within the scope of the invention that there may be patch designs which will accommodate the placement and securement of the anchor to the fabric that covers the frame of the patch. For example, a frame for a patch that is made out of metal such as Nitinol can provide for "windows". The device, covered with a mesh fabric, for example silicone or Dacron, would therefore allow the anchoring barbs to be passed through the "windows" in the frame of the patch. In this case, the barb can be secured to the patch in the fabric covering the frame.

Alternatively, the patch can be secured by passing barbs that engage the lattice of the patch frame. These embodiments of the invention illustrate designs in which the barbs engage with the vertical, horizontal or crisscrossed structures/members of the frame. In this case, the barbs would pass through the mesh or lattice of the frame and they would be unable to pass back out of the structure.

Although this discussion refers to "anchor bands" that are shown to be two anchors connected by a suture, it is also contemplated that single barbs with sutures are placed and the sutures' ends, at the outer surface of the annulus, are tied after placement through the patch.

Figure 53:
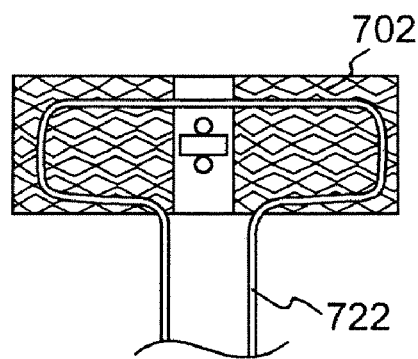
FIG. 53 shows a still further illustrative embodiment of a stent/patch having a frame.
Figure 54A:
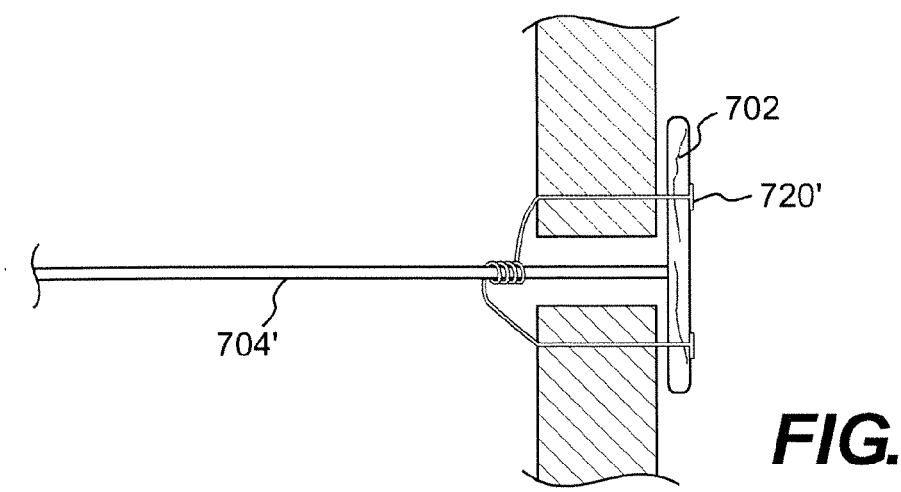
FIG. 54A-F shows a still further illustrative embodiment of an annular stent/patch having a self-contained fixation tightening feature.
Figure 54B:
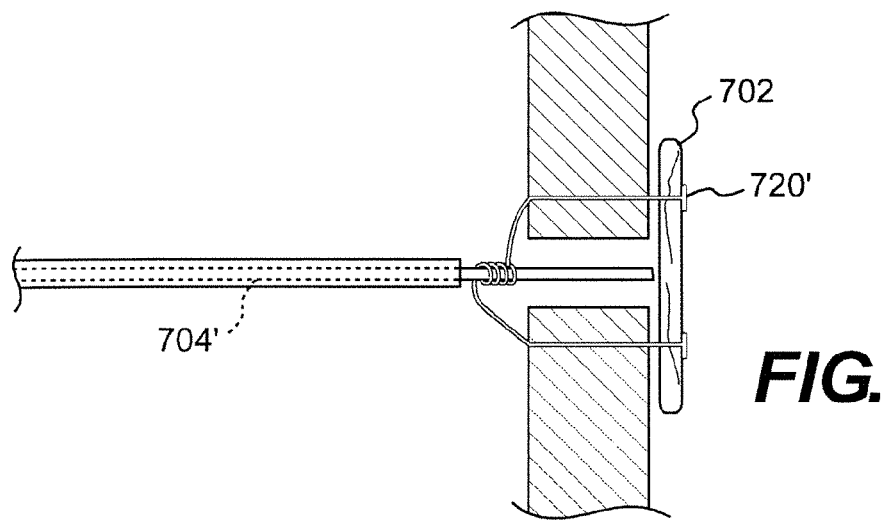
Figure 54C:
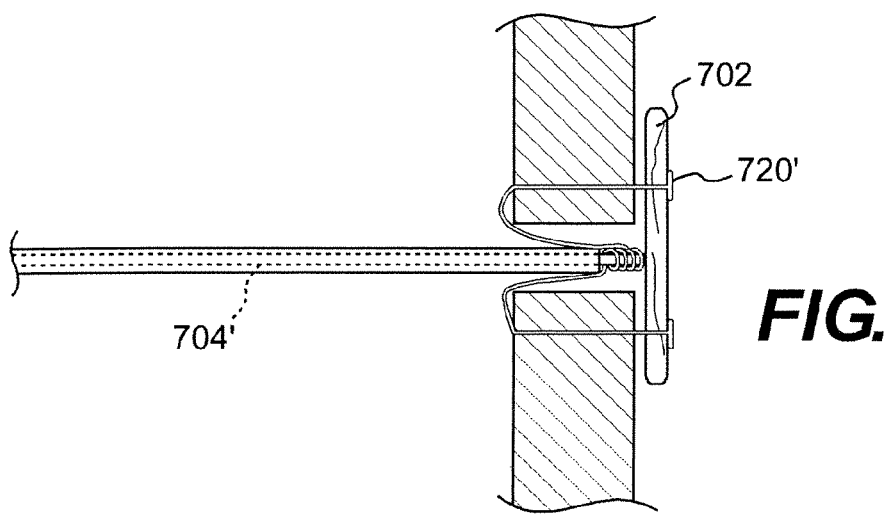
Figure 54D:
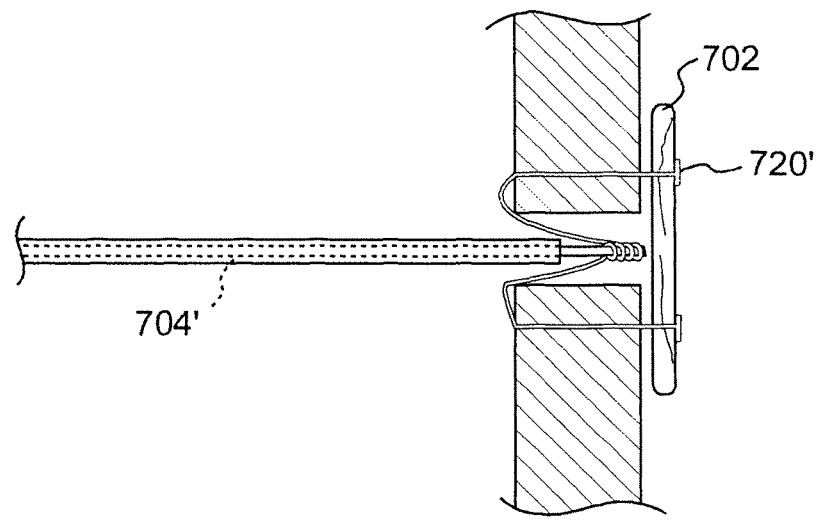
Figure 54E:
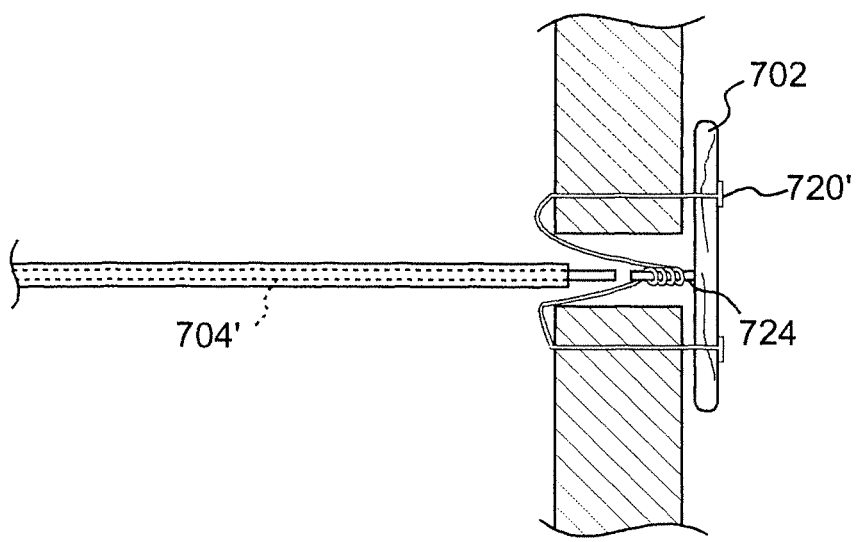
Figure 54F:
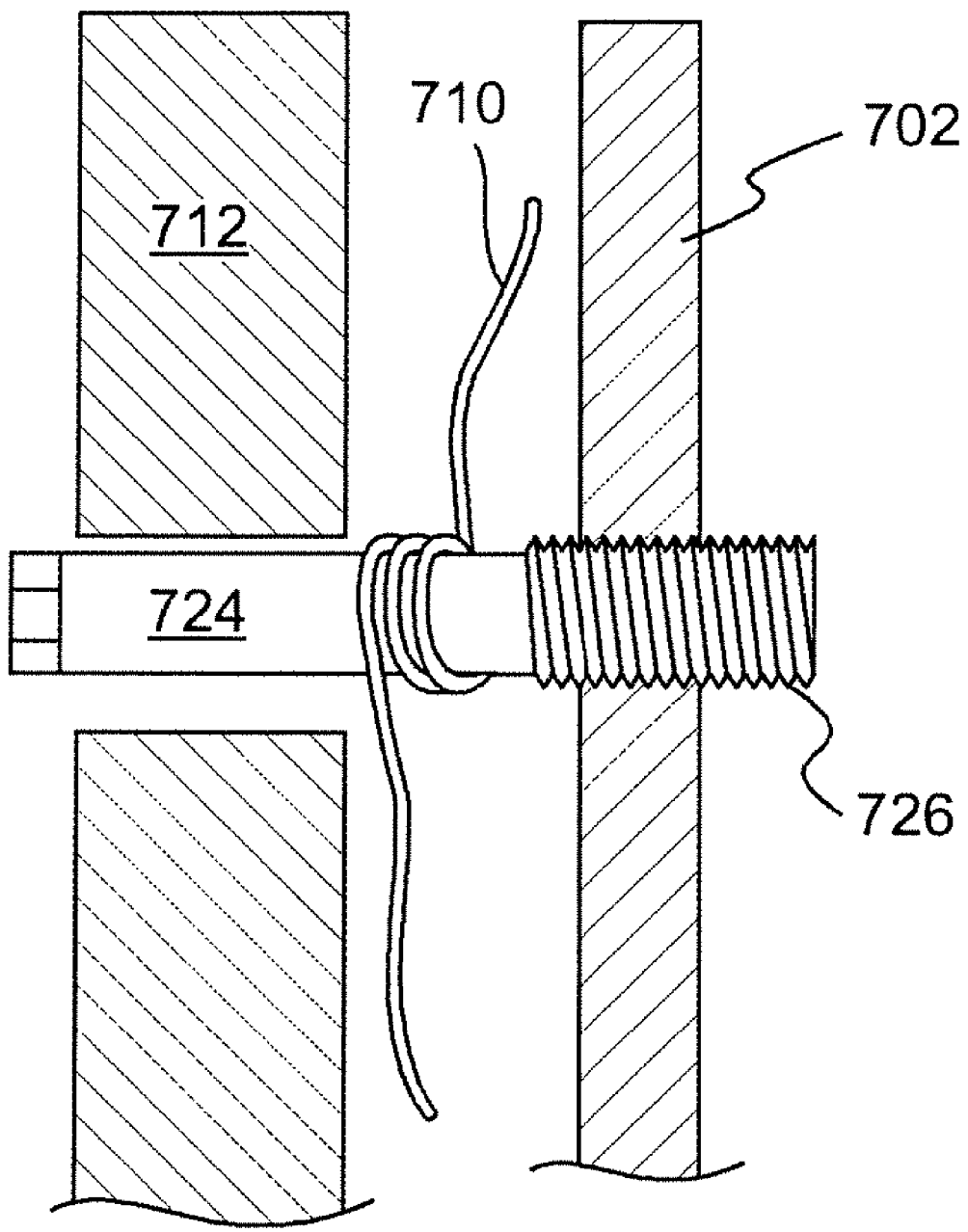

One objective in the designs discussed hereinabove is to provide a way to "pull up the slack" in a system to adjust the length of sutures and for anchor bands. According to the present invention, a technique referred to as the "Lasso Cinch Knot" was developed as a means to draw the anchor bands together with a suture cinch line that is incorporated into the patch design. FIG. 53 gives further description of the use of the Lasso embodiment. In essence, patch and frame constructs are used that incorporate the "barbs through the patch" design. Once the barbs have passed through the patch, an internal lasso 722 is drawn tight around the sutures of the anchor bands and thus draws the extra suture material within the patch. The internal lasso gathers the sutures of the bands, and as the lasso is tightened, it cinches together the sutures of the bands and therefore tightens them and eliminates slack, bringing the patch/stent into closer or tighter engagement with the annulus wall. The patch in FIG. 53 additionally provides for a diamond shape grid pattern, which advantageously provides a grid which will while allowing a probe or similar instrument to pass through with little resistance, provides resistance to a barb or other restraining feature on the instrument. The frame shown can be made from nitinol, and the locking and holding windows shown at the center of the figure would allow for rotation about the z-axis during placement. A slipknot technique using, for example a knot pusher, would aid in the loop pulling process by the lasso. The internal loop (lasso) can be tacked to the outside corners of the patch/stent, in order to hold the loop at the outer edges of the patch frame. When cinching the lasso knot, the loop can be pulled free from some or all of its tacked attachment points to the frame, to prevent deformation of the planar shape of the frame when cinching the lasso. As above, the frame can be a composite structure or sandwich formed with some type of mesh fabric. The proximal mesh fabric can be bonded fully to the patch frame, for example through the use of an adhesive, for instance a silicone. Adhesive, advantageously, can fill the interstices of the grid pattern while allowing for easy probe penetration and protection of the suture lines. Protection of the suture lines is advantageous when the lasso is used to pull and bunch a group of band sutures together.

Figure 55:
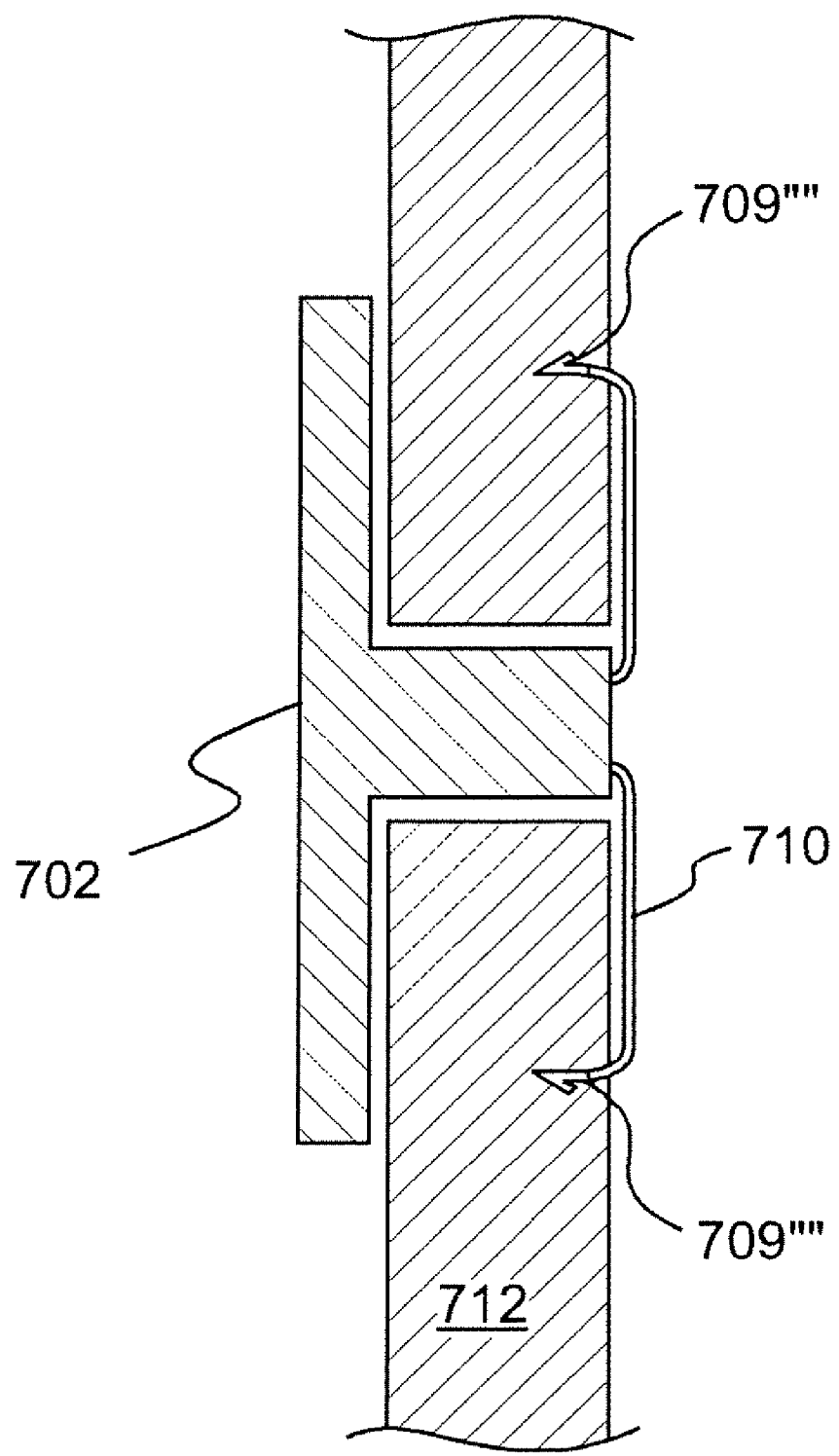
FIG. 55 shows a still further exemplary embodiment of the present invention having external fixation anchors.

It is also contemplated within the scope of the present invention that sutures 710' can be preattached directly to a stent/patch. As shown in FIG. 52A several separate barbs 709''' into the annulus 712 can be directly attached to the patch 702. Each "barb" of FIG. 52A can be independently placed into the annulus after the patch is deployed. This can be seen to be similar to the embodiment including barbs 709'''' of FIG. 55.

Figure 56A:
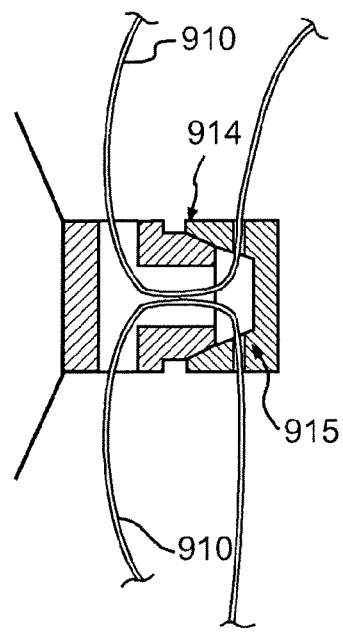
FIG. 56A-C shows a still further exemplary embodiment of the present invention having external fixation anchors.
Figure 56B:
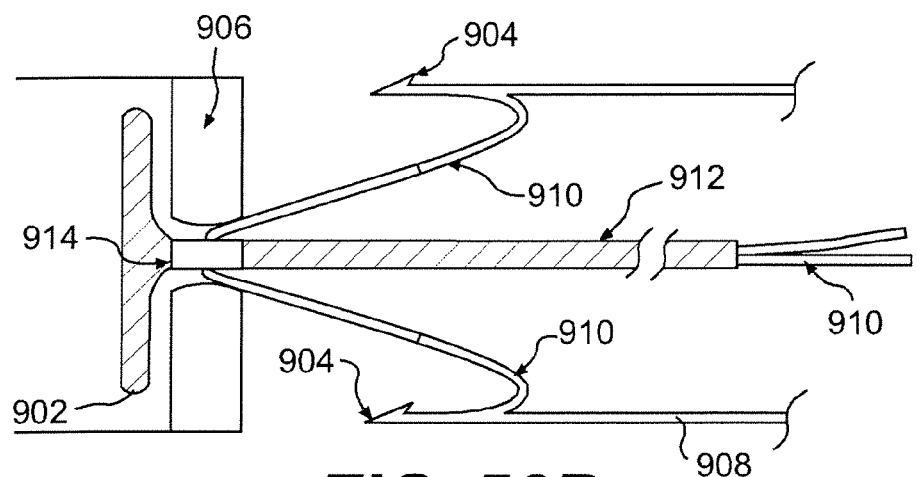
Figure 56C:
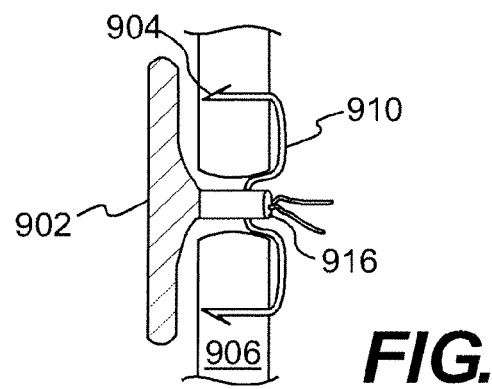

An alternative embodiment for securing a patch 902 and reapproximating a rent is providing each of the separate barbs with sutures having variable lengths as shown in FIG. 56. Each independent suture barb 904 is placed into the annulus 906 or into the patch 902 with the barb delivery tool 908. After the placement, all of the suture lines 910 are drawn taught, by drawing on the free ends that exit the patch delivery tool 912. A locking element 914 that uses a gasket 916 and threading mechanism is attached to the patch 902 and is used to tighten the gasket 916 around the distal ends of the sutures 910. The patch delivery tool 912 is removed and the extra suture length is cut. It is also possible that the gasket mechanism could be a press-fit to accommodate the tightening of the sutures to the patch.

Figure 57A:
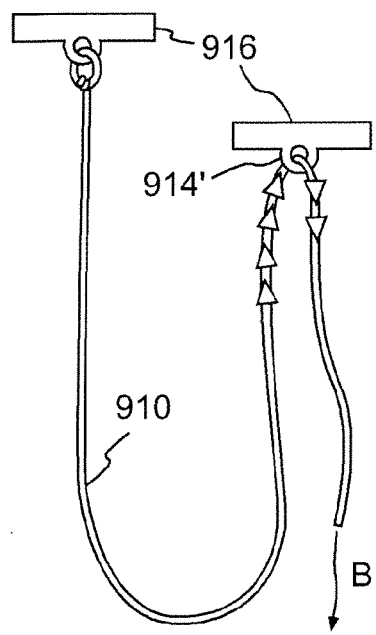
FIG. 57A-C shows a still further exemplary embodiment of the present invention having external fixation anchors.
Figure 57B:
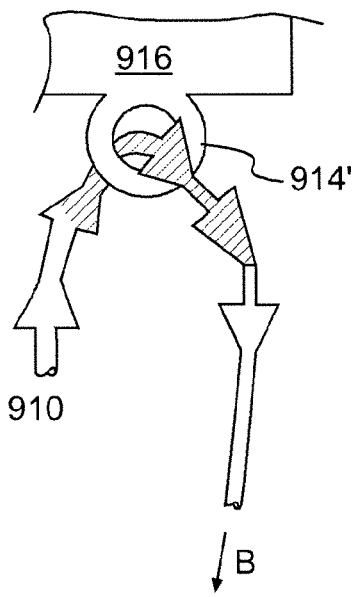
Figure 57C:
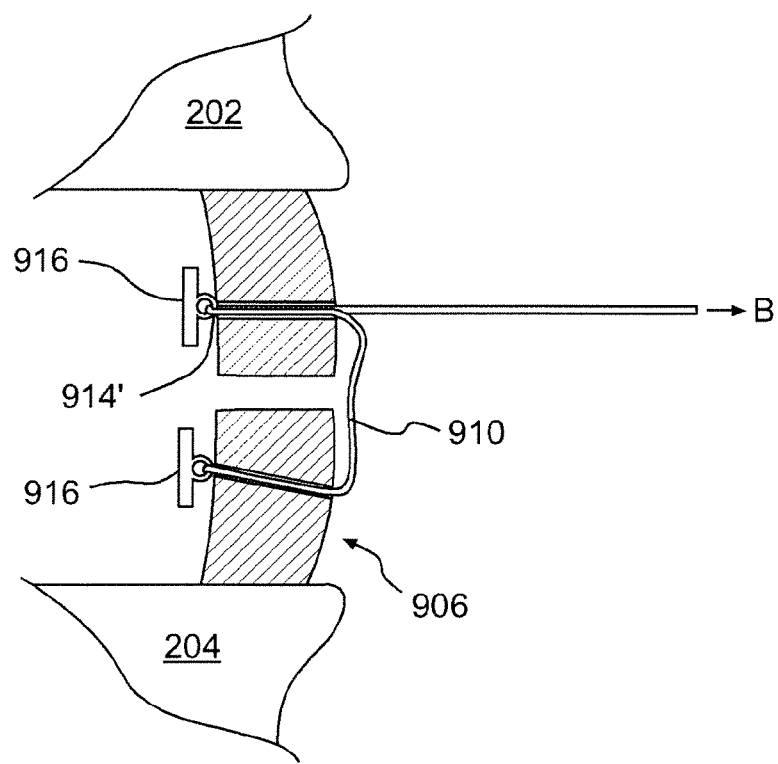

Alternatively, the locking mechanism can be as shown in FIG. 57, although in this case the engagement of the locking element 914' takes part on the patch. Pulling the suture 910 in the direction of arrow B will tighten and lockingly hold in tension to aid in securement and reapproximation. The adjustable length suture band between the two anchors allows slack to be taken up between the anchors 916. Two T-type anchors are illustratively shown in this example, but multiple anchors of differing configurations could be used. The locking features can be included on the feature band, as depicted here, and allow for substantially one-way locking engagement with the anchor members. This adjustability advantageously promotes for the accommodation of varying thickness of the annulus from patient to patient. The suture slack in this embodiment may be taken up to close the defect in the annulus and/or to shorten the band between anchors for a secondary cinching of multiple tensioned suture bands as described hereinabove.

The cinch line and the Lasso concepts in essence try to facilitate the re-approximation and drawing of tissues together in a fast and simple way. Other contemplated embodiments for "tension" elements include using an elastic coupler as a part of the anchor band used to fixate the device. The elastic coupler can be expanded for placement, and upon release, can draw tension to pull the tissues together. The coupler could be made of a biocompatible metal or polymer, or could be constructed of a biodegradable/bioabsorbable material.

Similarly, an alternative embodiment to cause tension within the device and draw the tissues together after placement of the anchor bands might include an elastic band or band with a spring which one end can be attached to the anchor bands and the other end attached to the patch. Alternatively, the anchor bands might, in and of themselves may be made of an elastic band between the barbs, or may contain a spring element between the barbs. Such an embodiment can be made to resemble a so-called "Bobber Spring." Again, it is contemplated that the elastic or resilient element could be made from a wide variety of metals, polymeric, or biodegradable/bioabsorbable material.

Figure 59:
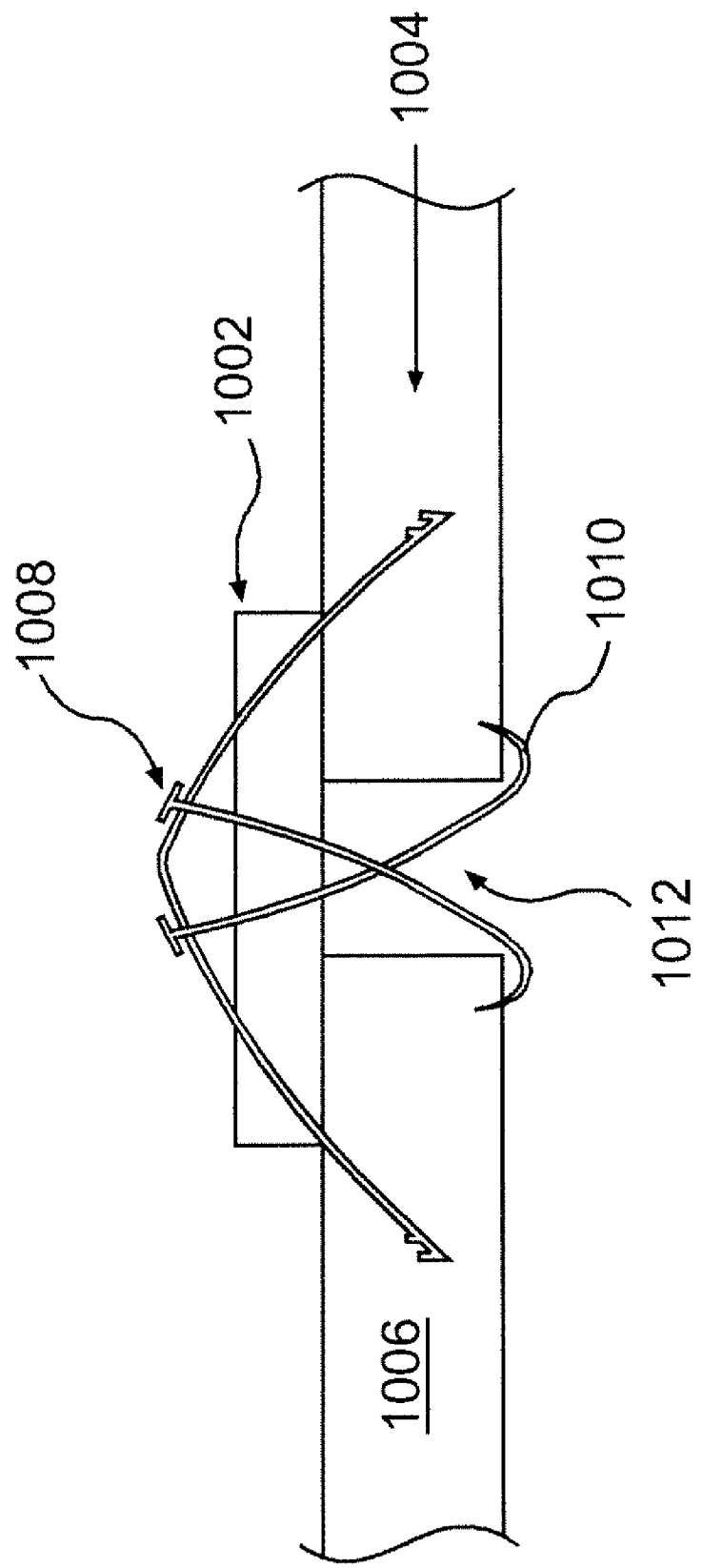
FIG. 59 shows a still further exemplary embodiment of the present invention having a springing arrangement.

FIG. 59 describes an embodiment where the patch element 1002 takes the form of a mesh seal. The securement is effected by a hook having a barb element 1004 that penetrates the inner surface of the annulus 1006, while the inner connection of the hook (barb) 1004 is attached to the patch in such a fashion as to add tension between the outer surface of the annulus and the inner surface in proximity to the patch, thus drawing the annular tissues together. The patch/stent 1002 contains a spring ribbon element 1008 which can be formed from nitinol or other spring material. Hooks 1010 are then deployed to "grab" the annulus, either through penetration or through grasping into the aperture 1012 as shown.

FIGS. 54*a-f* shows another embodiment of a means to draw the suture lines together to cause tension between the inner and outer tissues of the annulus. Anchor bands, for example T-barbs 720' are placed through the annulus and the patch, and they are secured to the patch 702. "Slack" in the suture of the anchor band is "rotated" around a detachable portion of the delivery tool 704' and a locking element, for example a screw configuration 724 as shown in the drawing, is used to lock the extra suture line in place affixed to threads 726 with the patch 702. The delivery tool 704' is then removed.

Figure 58A:
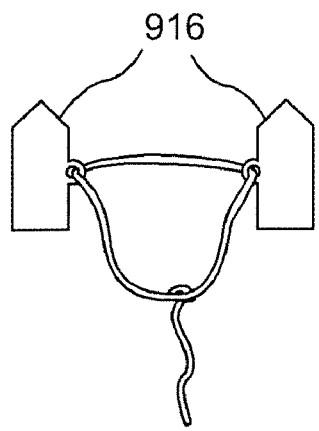
FIG. 58A-C shows a still further exemplary embodiment of the present invention having external fixation anchors.
Figure 58B:
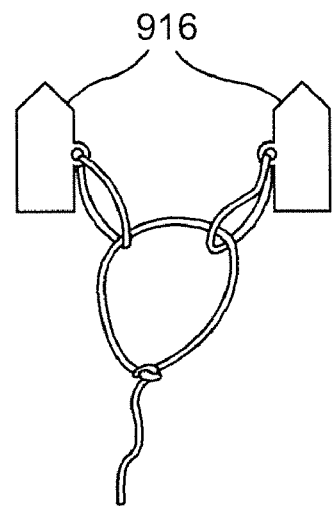
Figure 58C:
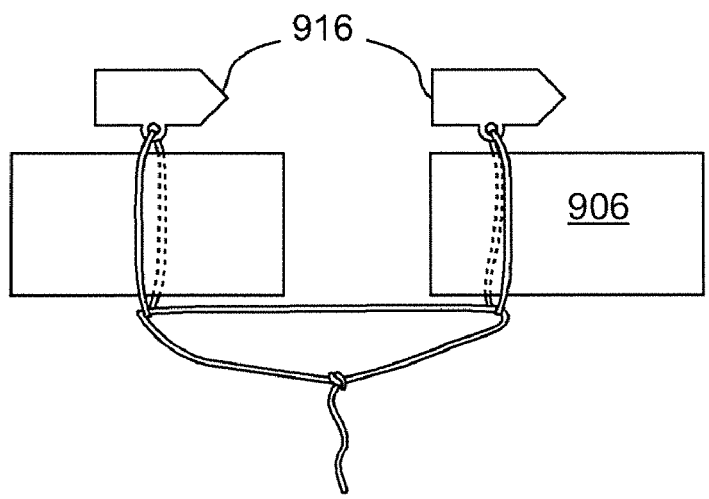

FIG. 58 shows alternative embodiments for tightening "anchoring barbs" with different configurations of sutures and cinch lines. For example in FIG. 58B each independent barb has a looped suture attached to it. Through each of these loops is passed a cinch line, which contains a knot. After placement of the barbs within the annulus, and possibly through the patch, the cinch line draws the loops of the barbs together. The advantage of this embodiment is that it allows for the independent placement of multiple barbs and the ability to draw all of them together.

Although cinch lines have been described as using a knot to "lock" the length of the suture, other mechanisms could also lock the length, as shown in FIG. 57. The locking of the suture length is accomplished through a mechanical element located on the barb which engages with three dimensional elements attached to the suture line which mechanically press fit through the engagement element on the barb, thus locking the length of the suture line into place.

Although the embodiments of FIG. 57 and FIG. 58 depict the use of a single locking mechanism (e.g., knot on cinch line), it is conceivable that various designs could use more than one locking element to achieve the re-approximation and drawing together the tissue surrounding an aperture.

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Ducheyne et al.), U.S. Pat. No. 5,122,154 (Rhodes), U.S. Pat. No. 5,204,106 (Schepers at al.), U.S. Pat. No. 5,888,220 (Felt et al.) and U.S. Pat. No. 5,376,120 (Sarver et al.).

Various materials know to those skilled in the art can be employed in practicing the present invention. By means of example only, the body portions of the stent could be made of NiTi alloy, plastics including polypropylene and polyethylene, stainless steel and other biocompatible metals, chromium cobalt alloy, or collagen. Webbing materials can include silicone, collagen, ePTFE, DACRON, polyester, polypropylene, polyethylene, and other biocompatible materials and can be woven or non-woven. Membranes might be fashioned of silicone, propylene, polyester, SURLYN, PEBAX, polyurethane or other biocompatible materials. Inflation fluids for membranes can include gases, liquids, foams, emulsions, and can be or contain bioactive materials and can also be for mechanical, biochemical and medicinal purposes. The stent body, webbing and/or membrane can be drug eluting or bioabsorbable, as known in the medical implant arts.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating a defect of an intervertebral disc, comprising:
    inserting a patch member into the intervertebral disc below a surface of an outer annular wall with an elongate patch delivery tool;
    inserting a first anchor into annular tissue and the patch member with an elongate anchor delivery tool;
    inserting a second anchor into the annular tissue and the patch member with the elongate anchor delivery tool, wherein the first and second anchors are connected to each other by an elongate element;
    adjusting a length and tensioning the elongate element; and
    securing the tensioned elongate element with a locking element.

2. The method of claim 1 wherein inserting the patch member includes inserting a patch member into the intervertebral disc to a location adjacent to the defect to be treated.

3. The method of claim 2 wherein inserting the patch member includes inserting the patch member through the defect to be treated.

4. The method of claim 3 wherein:
    inserting the first anchor includes inserting the first anchor into annular tissue on a first side of the defect to be treated;
    inserting the second anchor includes inserting the second anchor into annular tissue on a second side of the defect to be treated; and
    securing the tensioned elongate element includes securing the elongate element across the defect to reapproximate the defect.

5. The method of claim 4 wherein:
    the patch member can have a first configuration and a second larger configuration;
    inserting the patch member includes inserting the patch member into the intervertebral disc when the patch member is in the first configuration; and
    the method further includes causing the patch member to have the second larger configuration and at least partially span the defect after the patch member is inserted into the intervertebral disc.

6. The method of claim 1 wherein:
    inserting the first anchor includes inserting the first anchor into annular tissue on a first side of the defect to be treated;
    inserting the second anchor includes inserting the second anchor into annular tissue on a second side of the defect to be treated; and
    securing the tensioned elongate element includes securing the elongate element across the defect to reapproximate the defect.

7. A method for treating a defect of an intervertebral disc, comprising:
    inserting a patching element into the intervertebral disc below a surface of an outer annular wall through the defect with an elongated patch delivery tool;

inserting a first anchoring element into tissue on a first side of the defect to be treated with an elongate anchor delivery tool;

inserting a second anchoring element into tissue on a second side of the defect to be treated with an elongate anchor delivery tool, wherein the first and second anchoring elements are connected to each other by an elongate connecting element;

adjusting a length and tensioning the connecting element across the defect to reapproximate the defect; and securing the tensioned connecting element with a locking element.

8. The method of claim 7 wherein:

the patching element can have a first configuration and a second larger configuration;

inserting the patching element includes inserting the patching element into the intervertebral disc when the patching element is in the first configuration; and the method further includes causing the patching element to have the second larger configuration and at least partially span the defect after the patching element is inserted into the intervertebral disc.

9. The method of claim 7, wherein said locking element is selected from the group consisting of a knot, clip, fastener and retainer.

10. The method of claim 7, wherein the first anchoring element resides on an outside aspect of an annulus, and wherein the second anchoring element resides on an inside aspect of said annulus.

11. The method of claim 7, wherein said connecting element comprises a suture, band, tether, wire, filament, line or tension band.

12. The method of claim 7, wherein at least one of said first and second anchoring elements, said connecting element and said patching element comprises biocompatible, biodegradeable, or bioabsorbable material.

13. The method of claim 12, wherein at least one of said first and second anchoring elements, said connecting element and said patching element comprises collagenous material.

14. The method device of claim 7, wherein at least one of said first and second anchoring elements, said connecting element and said patching element comprises bioactive material or material to facilitate regeneration of tissue.

15. The method of claim 7, wherein said patching element is configured as a sealing construct from the set including a stent, scaffold, barrier, and membrane.

16. The method of claim 7, wherein said patching element comprises a sealing construct from the set including a scaffold, barrier, stent, and membrane to at least partially span the annular defect.

* * * * *